US010927414B2

(12) United States Patent
Skorecki et al.

(10) Patent No.: US 10,927,414 B2
(45) Date of Patent: Feb. 23, 2021

(54) METHODS AND KITS FOR DETERMINING PREDISPOSITION TO DEVELOP KIDNEY DISEASES

(71) Applicants: Technion Research & Development Foundation Limited, Haifa (IL); Ramot at Tel-Aviv University Ltd., Tel-Aviv (IL); Walter Gabriel Wasser, Jerusalem (IL); Rambam Med-Tech Ltd., Haifa (IL)

(72) Inventors: Karl Skorecki, Haifa (IL); Shay Tzur, Haifa (IL); Saharon Rosset, Hamot-HaShavim (IL); Walter Gabriel Wasser, Jerusalem (IL); Doron M. Behar, Hof HaCarmel (IL); Revital Shemer, Haifa (IL)

(73) Assignees: Technion Research & Development Foundation Limited, Haifa (IL); Ramot at Tel-Aviv University Ltd., Tel-Aviv (IL); Walter Gabriel Wasser, Jerusalem (IL); Rambam Med-Tech Ltd., Haifa (IL)

(*) Notice: Subject to any disclaimer, the term of this patent is extended or adjusted under 35 U.S.C. 154(b) by 0 days.

(21) Appl. No.: 16/449,585

(22) Filed: Jun. 24, 2019

(65) Prior Publication Data
US 2019/0309368 A1    Oct. 10, 2019

Related U.S. Application Data

(60) Continuation of application No. 15/136,929, filed on Apr. 24, 2016, now Pat. No. 10,351,911, which is a division of application No. 13/153,569, filed on Jun. 6, 2011, now abandoned.

(60) Provisional application No. 61/351,960, filed on Jun. 7, 2010.

(51) Int. Cl.
*C12Q 1/6883* (2018.01)
*C12Q 1/70* (2006.01)
*G01N 33/68* (2006.01)

(52) U.S. Cl.
CPC ......... *C12Q 1/6883* (2013.01); *C12Q 1/703* (2013.01); *G01N 33/6893* (2013.01); *C12Q 2600/106* (2013.01); *C12Q 2600/156* (2013.01); *C12Q 2600/172* (2013.01); *G01N 2333/775* (2013.01); *G01N 2800/50* (2013.01)

(58) Field of Classification Search
None
See application file for complete search history.

(56) References Cited

U.S. PATENT DOCUMENTS

| | | |
|---|---|---|
| 6,582,908 B2 | 6/2003 | Fodor et al. |
| 2005/0142596 A1 | 6/2005 | Krolewski et al. |
| 2010/0297660 A1 | 11/2010 | Winkler et al. |
| 2011/0030078 A1 | 2/2011 | Raper et al. |
| 2012/0003644 A1 | 1/2012 | Skorecki et al. |
| 2012/0128682 A1 | 5/2012 | Pays et al. |
| 2016/0230233 A1 | 8/2016 | Skorecki et al. |

FOREIGN PATENT DOCUMENTS

WO    WO 2011/133474    10/2011

OTHER PUBLICATIONS

Advisory Action Before the Filing of an Appeal Brief dated Nov. 20, 2018 From the US Patent and Trademark Office Re. U.S. Appl. No. 15/136,929. (4 pages).
Applicant-Initiated Interview Summary dated Apr. 3, 2014 From the US Patent and Trademark Office Re. U.S. Appl. No. 13/153,569.
Examiners Answer dated Feb. 23, 2016 Before the Patent Trial and Appeal Board of the US Patent and Trademark Office Re. U.S. Appl. No. 13/153,569.
Notification of Non-Compliant Appeal Brief (37 CFR 41.37) dated Oct. 7, 2015 From the US Patent and Trademark Office Re. U.S. Appl. No. 13/153,569.
Official Action dated Nov. 6, 2014 From the US Patent and Trademark Office Re. U.S. Appl. No. 13/153,569.
Official Action dated Feb. 7, 2018 From the US Patent and Trademark Office Re. U.S. Appl. No. 15/136,929. (20 pages).
Official Action dated Sep. 14, 2012 From the US Patent and Trademark Office Re. U.S. Appl. No. 13/153,569.
Official Action dated Dec. 20, 2013 From the US Patent and Trademark Office Re. U.S. Appl. No. 13/153,569.
Official Action dated May 24, 2013 From the US Patent and Trademark Office Re. U.S. Appl. No. 13/153,569.
Official Action dated Aug. 27, 2018 From the US Patent and Trademark Office Re. U.S. Appl. No. 15/136,929. (11 pages).

(Continued)

*Primary Examiner* — Paul J Holland

(57) ABSTRACT

Provided are methods and kits for determining predisposition of a subject to develop a kidney disease, by identifying in a sample of the subject at least one APOL1 polypeptide variant which is characterized by a higher trypanolytic activity on *Trypanosoma brucei rhodesiense* as compared to the trypanolytic activity of wild type APOL1 polypeptide as set forth in SEQ ID NO:1 on the *Trypanosoma brucei rhodesiense* under identical assay conditions; or at least one APOL1 nucleotide mutation in the APLO1 genomic sequence set forth in SEQ ID NO:3, wherein the at least one nucleotide mutation or polypeptide variant being in linkage disequilibrium (LD) with the S342G mutation in the APOL1 polypeptide set forth in SEQ ID NO:1, wherein presence of the APOL1 polypeptide variant indicates increased predisposition of the subject to develop the kidney disease.

7 Claims, 6 Drawing Sheets
(5 of 6 Drawing Sheet(s) Filed in Color)
Specification includes a Sequence Listing.

(56) References Cited

OTHER PUBLICATIONS

Behar et al. "African Ancestry Allelic Variation at the MYH9 Gene Contributes to Increased Susceptiblity to Non-Diabetic End-Stage Kidney Disease in Hispanic Americans", Human Molecular Genetics, 19(9): 1816-1827, 2010.

Bostrom et al. "Candidate Genes for Non-Diabetic ESRD in African Americans: A Genome-Wide Association Study Using Pooled DNA", Human Genetics, 128(2): 195-204, Aug. 2010.

Genovese et al. "Association of Trypanolytic ApoL1 Variants With Kidney Disease in African-Americans", Science, 329(5993): 841-845, Aug. 13, 2010. & Supplemental Material.

Kao et al. "MYH9 Is Associated With Nondiabetic End-Stafe Renal Diease in African Americans", Nature Genetics, 40(10): 1185-1192, Oct. 2008.

Kopp et al. "MYH9 Is a Major-Effect Risk Gene for Focal Segmental Glomerulosclerosis", Nature Genetics, 40(10): 1175-1184, Oct. 2008.

Lecordier et al. "C-Terminal Mutants of Apolipoprotein L-I Efficiently Kill Both Trypanosoma Brucei Brucei and Trypanosoma Brucei Rhodesiense", PLoS Pathogens, 5(12): e1000685-1-e1000685-11, Dec. 2009.

NCBI "Reference SNP (refSNP) Cluster Report rs60910145, 'With Untested Allele'", NCBI dbSNP Database [Online], 3 P., Nov. 23, 2007.

NCBI "Reference SNP (refSNP) Cluster Report rs71785313, 'Clinical Channel'", NCBI dbSNP Database [Online], 3 P., Jan. 4, 2008.

NCBI "Reference SNP (refSNP) Cluster Report rs73885319, 'With Untested Allele'", NCBI dbSNP Database [Online], 3 P., Jan. 19, 2009.

Nelson et al. "Dense Mapping of MYH9 Localizes the Strongest Kidney Disease Associations to the Region of Introns 13 to 15", Human Molecular Genetics, 19(9): 1805-1815,2010.

Paul "Genes Linked to Kidney Disease", Genetics Abstracts, 2 P., Oct. 3, 2008.

Ross et al. "HIV-Associated Nephropathy", AIDS, 18(8): 1089-1099, May 21, 2004.

Rosset et al. "The Population Genetics of Chronic Kidney Disease: Insights From the MYH9-APOL1 Locus", Nature Reviews Nephrology, 7(6): 313-327, Jun. 2011. Abstract.

Shlush et al. "Admixture Mapping of End Stage Kidney Disease Genetic Susceptibility Using Estimated Mutual Information Ancestry Informative Markers", BMC Medical Genomics, 3(47): 1-12, 2010.

Takahashi et al. "Apolipoprotein L1 Isoform a Precursor [*Homo Sapiens*]", NCBI Database [Online], NCBI Reference Sequence: NP_003652.2, GenBank Accession No. NO_003652, 3 P., Sep. 28, 2008.

Tomlinson et al. "High-Density-Lipoprotein-Independent Killing of Trypanosoma Brucei by Human Serum", Molecular and Biochemical Parasitology, 70: 131-138, 1995.

Tzur et al. "Missense Mutations in the APOL1 Gene Are Highly Associated With End Stage Kidney Disease Risk Previously Attributed to the MYH9 Gene", Human Genetics, 128: 345-350, 2010.

Fig. 4C
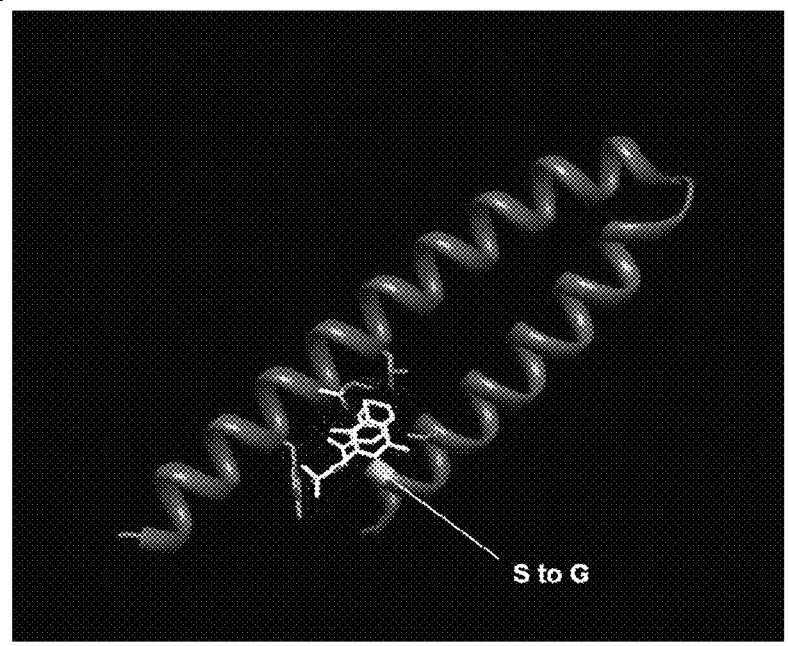
Figs. 5A                Figs. 5B
Controls   African   Cases
               Americans
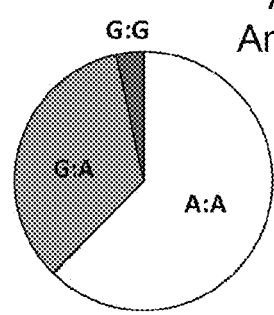   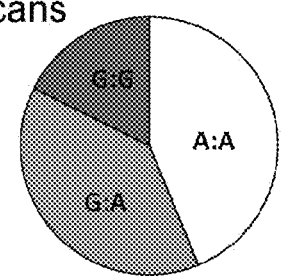
Hispanic
Americans
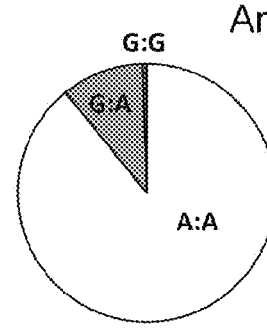
Figs. 5C                Figs. 5D

METHODS AND KITS FOR DETERMINING PREDISPOSITION TO DEVELOP KIDNEY DISEASES

RELATED APPLICATIONS

This application is a continuation of U.S. patent application Ser. No. 15/136,929 filed on Apr. 24, 2016, now U.S. Pat. No. 10,351,911, which is a division of U.S. patent application Ser. No. 13/153,569 filed on Jun. 6, 2011, which claims the benefit of priority under 35 USC 119(e) of U.S. Provisional Patent Application No. 61/351,960 filed Jun. 7, 2010.

The contents of the above applications are all incorporated by reference as if fully set forth herein in their entirety.

SEQUENCE LISTING STATEMENT

The ASCII file, entitled 77864SequenceListing.txt, created on Jun. 24, 2019 comprising 76,998 bytes, submitted concurrently with the filing of this application is incorporated herein by reference.

FIELD AND BACKGROUND OF THE INVENTION

The present invention, in some embodiments thereof, relates to methods and kits for determining predisposition to develop kidney diseases, and, more particularly, but not exclusively, to methods of designing life style change and treatment regimens for a subject predisposed to develop a kidney disease.

Chronic Kidney Disease (CKD) is a powerful independent risk factor for cardiovascular disease and death at all stages. Most patients with CKD will succumb to cardiovascular complications rather than reach end-stage kidney disease (ESKD). Recent reports estimate that as many as 600 million people worldwide have CKD, and hence are at greatly increased risk of cardiovascular disease including hypertension [Hypertext Transfer Protocol (dot)worldwideweb (dot)kidney(dot)org(dot)au/NewsEvents/WorldKidneyDay/tabid/655/Default (dot)aspx].

Based on information from those countries where renal replacement therapy is available and registries are maintained, there are close to one million people with ESKD receiving dialysis treatment or a kidney transplant. In the United States, an estimated 15.5 million have stage 3 and 4 CKD, and 584,000 have ESKD. African Americans have five times greater risk for kidney disease than European Americans. Correspondingly, African-Americans also have a higher risk of mortality from cardiovascular disease than Americans of European ancestry, including death, non-fatal myocardial infarction, and stroke. Finally, it is now appreciated that hypertension, once thought to be a leading cause of CKD leading to ESKD, is the consequence of primary renal glomerular disease in certain risk populations.

Mapping by admixture linkage disequilibrium (MALD) localized an interval on chromosome 22, in a region that includes the MYH9 gene, which was shown to contain African ancestry risk variants associated with certain forms of ESKD (Kao et al. 2008; Kopp et al. 2008). This led to the new designation of MYH9 associated nephropathies. Subsequent studies identified clusters of single nucleotide polymorphisms (SNPs) within MYH9 with the largest odds ratios (OR) reported to date for the association of common variants with common disease risk (Bostrom and Freedman 2010). These MYH9 association studies were extended to earlier stage and related kidney disease phenotypes, and to population groups with varying degrees of recent African ancestry admixture (Behar et al. 2010; Nelson et al. 2010). Thus, the MYH9 has been proposed as a major genetic risk locus for a spectrum of non-diabetic ESKD. However, despite intensive efforts including re-sequencing of the MYH9 gene no suggested functional mutation has been identified (Nelson et al. 2010).

U.S. Patent Application No. 20100297660 to Winkler Cheryl et al. ("SINGLE NUCLEOTIDE POLYMORPHISMS ASSOCIATED WITH RENAL DISEASE") discloses methods for determining the genetic predisposition of a human subject to developing renal disease, such as focal segmental glomerulosclerosis (FSGS) or end-stage kidney disease by detection of one or more haplotype blocks comprising at least two tag single nucleotide polymorphisms (SNPs) in a non-coding region of a MYH9 gene or detecting the presence of at least one tag SNP in a non-coding region of a MYH9 gene.

Additional background art includes Tzur S, et al. (Missense mutations in the APOL1 gene are highly associated with end stage kidney disease risk previously attributed to the MYH9 gene) Hum. Genet. 2010, 128:345-50; Rosset S, et al. (The population genetics of chronic kidney disease: insights from the MYH9-APOL1 locus) Nat. Rev. Nephrol. 2011, May 3. [Epub ahead of print]; Genovese G, et al. (Association of trypanolytic ApoL1 variants with kidney disease in African Americans) Science 2010; 329:841-5; Behar D M, et al. (African ancestry allelic variation at the MYH9 gene contributes to increased susceptibility to non-diabetic end-stage kidney disease in Hispanic Americans) Hum. Mol. Genet. 2010 19(9):1816-27; Shlush L I, et al. (Admixture mapping of end stage kidney disease genetic susceptibility using estimated mutual information ancestry informative markers) BMC Med Genomics. 2010 3:47; and U.S. Patent Application No. 20110030078.

SUMMARY OF THE INVENTION

According to an aspect of some embodiments of the present invention there is provided a method of determining predisposition of a subject to develop a kidney disease, comprising: identifying in a sample of the subject at least one APOL1 polypeptide variant which is characterized by a higher trypanolytic activity on *Trypanosoma brucei rhodesiense* as compared to the trypanolytic activity of wild type APOL1 polypeptide as set forth in SEQ ID NO:1 on the *Trypanosoma brucei rhodesiense* under identical assay conditions, wherein presence of the APOL1 polypeptide variant indicates increased predisposition of the subject to develop the kidney disease, thereby determining the predisposition of the subject to develop the kidney disease.

According to an aspect of some embodiments of the present invention there is provided a method of determining predisposition of a subject to develop a kidney disease, comprising: identifying in a sample of the subject at least one APOL1 nucleotide mutation in the APLO1 genomic sequence set forth in SEQ ID NO:3 or at least one APOL1 polypeptide variant, wherein the at least one nucleotide mutation or polypeptide variant being in linkage disequlibrium (LD) with the S342G mutation in the APOL1 polypeptide set forth in SEQ ID NO:1, wherein presence of the APOL1 nucleotide mutation or the APOL1 polypeptide variant indicates increased predisposition of the subject to develop the kidney disease, thereby determining the predisposition of the subject to develop the kidney disease.

According to an aspect of some embodiments of the present invention there is provided a method of designing a life style change to a subject with the risk of kidney disease, comprising: (a) identifying in a sample of the subject at least one APOL1 polypeptide variant or at least one APOL1 nucleotide mutation, (i) wherein the variant is characterized by a higher trypanolytic activity on *Trypanosoma brucei rhodesiense* as compared to the trypanolytic activity of wild type APOL1 polypeptide as set forth in SEQ ID NO:1 on the *Trypanosoma brucei rhodesiense* under identical assay conditions; (ii) wherein the APOL1 nucleotide mutation is included in the APLO1 genomic sequence set forth in SEQ ID NO:3, and wherein the at least one nucleotide mutation being in linkage disequlibrium (LD) with the S342G mutation in the APOL1 polypeptide set forth in SEQ ID NO:1, wherein presence of the APOL1 polypeptide variant or the APOL1 nucleotide mutation indicates increased predisposition of the subject to develop the kidney disease, and; (b) designing the life style change based on presence or absence of the APOL1 polypeptide variant or the APOL1 nucleotide mutation, thereby designing life style change to a subject with the risk of kidney disease.

According to an aspect of some embodiments of the present invention there is provided a method of designing a life style change to a subject with the risk of kidney disease, comprising: (a) identifying in a sample of the subject at least one APOL1 polypeptide variant or at least one APOL1 nucleotide mutation, (i) wherein the variant is characterized by a higher trypanolytic activity on *Trypanosoma brucei rhodesiense* as compared to the trypanolytic activity of wild type APOL1 polypeptide as set forth in SEQ ID NO:1 on the *Trypanosoma brucei rhodesiense* under identical assay conditions; (ii) wherein the APOL1 nucleotide mutation is included in the APLO1 genomic sequence set forth in SEQ ID NO:3, and wherein the at least one nucleotide mutation being in linkage disequlibrium (LD) with the S342G mutation in the APOL1 polypeptide set forth in SEQ ID NO:1, wherein presence of the APOL1 polypeptide variant or the APOL1 nucleotide mutation indicates increased predisposition of the subject to develop the kidney disease, and; (b) designing the life style change based on presence or absence of the APOL1 polypeptide variant or the APOL1 nucleotide mutation, thereby designing life style change to a subject with the risk of kidney disease.

According to an aspect of some embodiments of the present invention there is provided a method of designing a nephrotoxic anti-retroviral treatment regimen to a subject infected with HIV, comprising: (a) identifying in a sample of the subject at least one APOL1 polypeptide variant or at least one APOL1 nucleotide mutation, (i) wherein the variant is characterized by a higher trypanolytic activity on *Trypanosoma brucei rhodesiense* as compared to the trypanolytic activity of wild type APOL1 polypeptide as set forth in SEQ ID NO:1 on the *Trypanosoma brucei rhodesiense* under identical assay conditions; (ii) wherein the APOL1 nucleotide mutation is included in the APLO1 genomic sequence set forth in SEQ ID NO:3, and wherein the at least one nucleotide mutation being in linkage disequlibrium (LD) with the S342G mutation in the APOL1 polypeptide set forth in SEQ ID NO:1, wherein presence of the APOL1 polypeptide variant or the APOL1 nucleotide mutation indicates increased predisposition of the subject to develop the kidney disease, and; (b) designing the nephrotoxic anti-retroviral treatment regimen based on presence or absence of the APOL1 polypeptide variant or the APOL1 nucleotide mutation, thereby designing a nephrotoxic anti-retroviral treatment regimen to the subject infected with HIV.

According to an aspect of some embodiments of the present invention there is provided a method of determining if a subject is suitable for donating a kidney for transplantation, comprising: (a) identifying in a sample of the subject at least one APOL1 polypeptide variant or at least one APOL1 nucleotide mutation, (i) wherein the variant is characterized by a higher trypanolytic activity on *Trypanosoma brucei rhodesiense* as compared to the trypanolytic activity of wild type APOL1 polypeptide as set forth in SEQ ID NO:1 on the *Trypanosoma brucei rhodesiense* under identical assay conditions; (ii) wherein the APOL1 nucleotide mutation is included in the APLO1 genomic sequence set forth in SEQ ID NO:3, and wherein the at least one nucleotide mutation being in linkage disequlibrium (LD) with the S342G mutation in the APOL1 polypeptide set forth in SEQ ID NO:1, wherein presence of the APOL1 polypeptide variant or the APOL1 nucleotide mutation indicates increased predisposition of the subject to develop a kidney disease, and; wherein increased predisposition of the subject to develop the kidney disease indicates that the subject is not suitable for donating the kidney for transplantation, thereby determining if the subject is suitable for donating a kidney for transplantation.

According to an aspect of some embodiments of the present invention there is provided a kit for determining predisposition to a kidney disease, comprising a reagent capable of specifically detecting at least one APOL1 nucleotide mutation in the APLO1 genomic sequence set forth in SEQ ID NO:3, wherein the at least one nucleotide mutation being in linkage disequlibrium (LD) with the S342G mutation in the APOL1 polypeptide set forth in SEQ ID NO:1.

According to some embodiments of the invention, the APOL1 polypeptide variant comprises a mutation in the C-terminal helix of the APOL1 polypeptide.

According to some embodiments of the invention, the APOL1 polypeptide variant has a reduced binding ability to serum resistance-associated protein (SRA) expressed by *Trypanosoma brucei rhodesiense* as compared to the binding ability of the APOL1 wild type polypeptide under identical assay conditions.

According to some embodiments of the invention, the APOL1 polypeptide variant comprises the amino acid sequence set forth in SEQ ID NO:1 with a mutation selected from the group consisting of G342, M384, N388-del and Y389-del.

According to some embodiments of the invention, the LD between the APOL1 nucleotide mutation and the S342G mutation is characterized by a Lewontin correlation coefficient (D') higher than 0.5.

According to some embodiments of the invention, the significance of the LD is characterized by LOD≥2.

According to some embodiments of the invention, the APOL1 nucleotide mutation is selected from the group consisting of the guanine-containing allele of single nucleotide polymorphism (SNP) rs73885319 (SEQ ID NO:6), the guanine-containing allele of SNP rs60910145 (SEQ ID NO:7), the guanine-containing allele of SNP rs9622363 (SEQ ID NO:8), the adenine-containing allele of SNP rs60295735 (SEQ ID NO:9) and the cytosine-containing allele of SNP rs58384577 (SEQ ID NO:10).

According to some embodiments of the invention, the kidney disease comprises end stage kidney disease.

According to some embodiments of the invention, the kidney disease comprises HIV-associated nephropathy (HIVAN).

According to some embodiments of the invention, the subject is infected with HIV.

According to some embodiments of the invention, the APOL1 nucleotide mutation is selected from the group consisting of the guanine-containing allele of single nucleotide polymorphism (SNP) rs73885319 (SEQ ID NO:6), the guanine-containing allele of SNP rs60910145 (SEQ ID NO:7), the guanine-containing allele of SNP rs9622363 (SEQ ID NO:8), the adenine-containing allele of SNP rs60295735 (SEQ ID NO:9) and the cytosine-containing allele of SNP rs58384577 (SEQ ID NO:10).

According to some embodiments of the invention, the reagent comprises a polynucleotide capable of specifically detecting the APOL1 nucleotide mutation.

According to some embodiments of the invention, the reagent comprises an antibody capable of specifically binding an APOL1 variant comprises the nucleotide mutation and not to the APLO1 wild type polypeptide.

According to some embodiments of the invention, the method further comprising informing the subject on the state of the predisposition to develop the kidney disease.

According to some embodiments of the invention, the nucleotide mutation creates an APOL1 protein variant.

According to some embodiments of the invention, the nucleotide mutation is detected by a DNA detection method.

According to some embodiments of the invention, the APOL1 protein variant is detected by a protein detection method.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

BRIEF DESCRIPTION OF THE SEVERAL VIEWS OF THE DRAWINGS

The patent or application file contains at least one drawing executed in color. Copies of this patent or patent application publication with color drawing(s) will be provided by the Office upon request and payment of the necessary fee.

Some embodiments of the invention are herein described, by way of example only, with reference to the accompanying drawings. With specific reference now to the drawings in detail, it is stressed that the particulars shown are by way of example and for purposes of illustrative discussion of embodiments of the invention. In this regard, the description taken with the drawings makes apparent to those skilled in the art how embodiments of the invention may be practiced.

In the drawings:

FIG. 1 is a schematic view of the chromosomal region encompassing the SNPs according to some embodiments of the present study.

Figure 2:
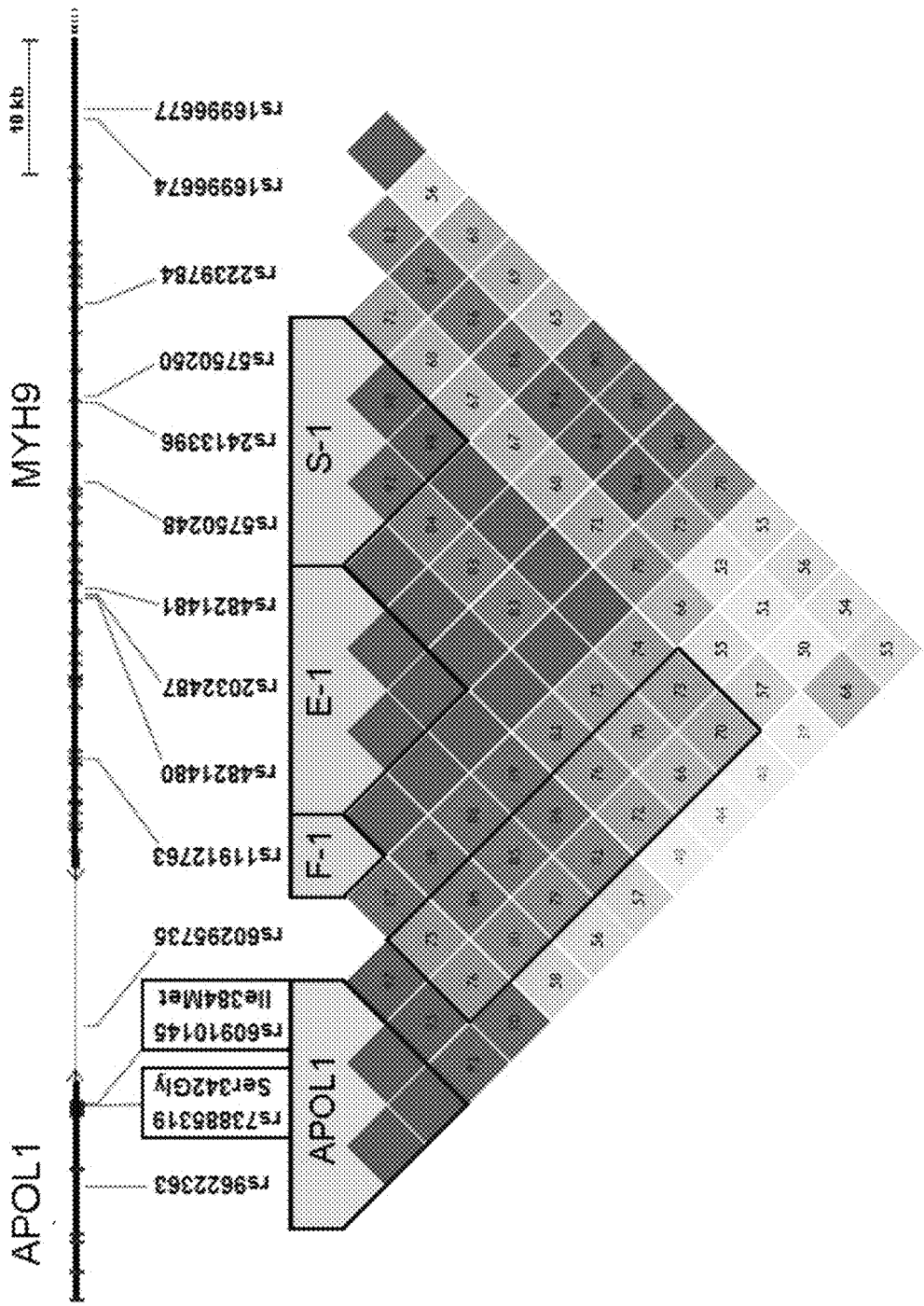
Figure 3C:
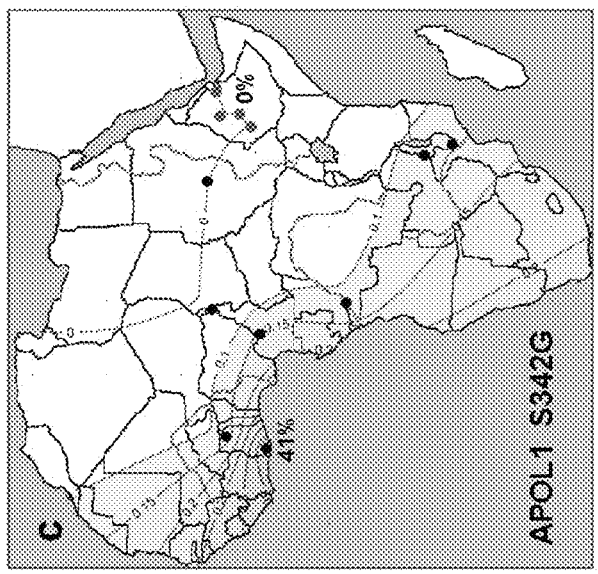
Figure 3B:
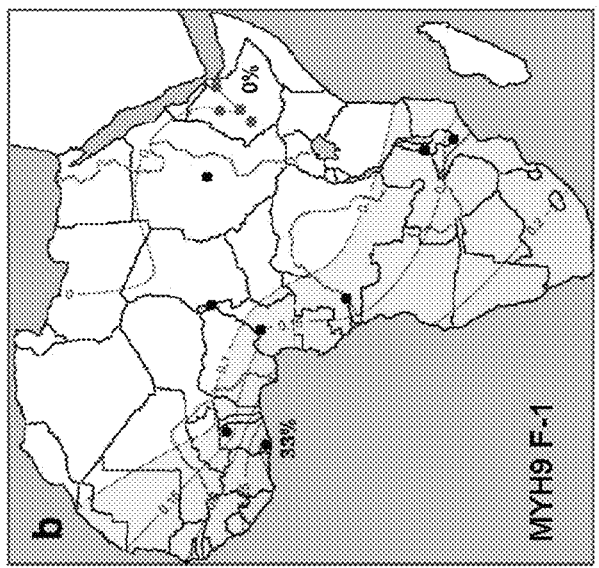
Figure 3A:
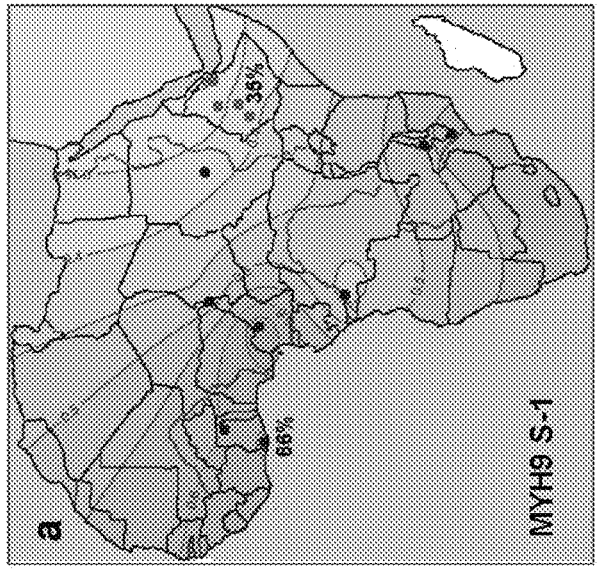
Figure 4A:
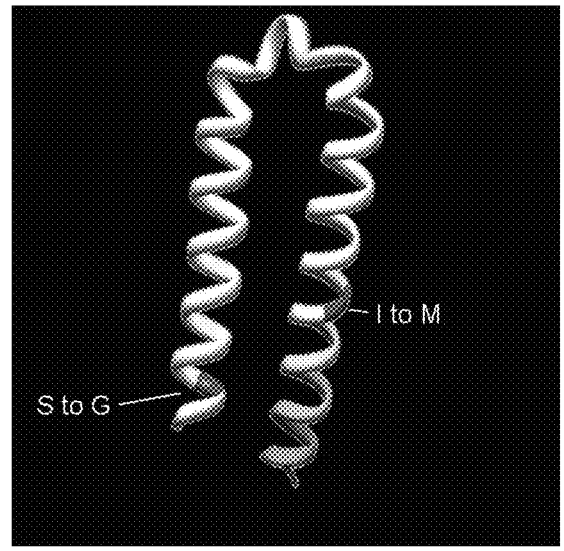
Figure 4B:
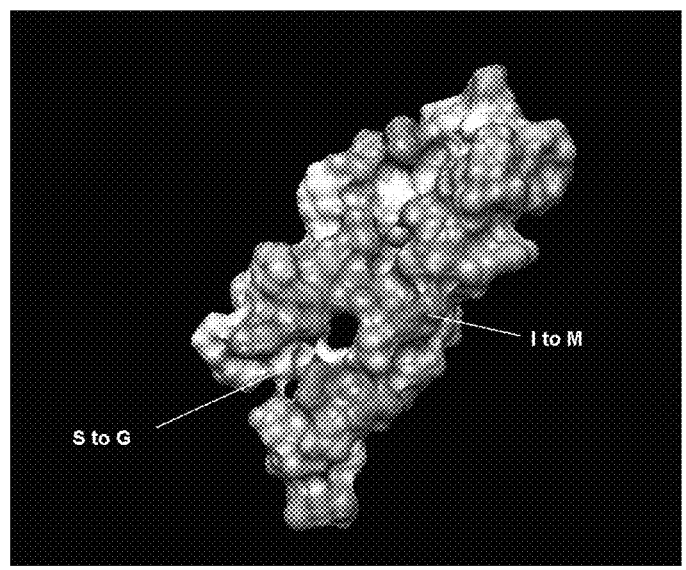

FIG. 2 is a linkage disequilibrium (LD) plot of the non-diabetic ESKD associated SNPs in the APOL1 and MYH9 region with their physical locations on chromosome 22. LD was calculated based on the African American control samples (n=140) and the LD plot was generated using the program HaploView (Barrett et al. 2005). The color scheme represents the pairwise linkage disequilibrium value (D'/LOD) for the 4 new SNPs outside MYH9 (2 of which are missense mutations in APOL1) and for the previously published 10 MYH9 SNPs described in Behar et al. 2010. Bright red squares presents SNPs with linkage LOD≥2 and D'=1. D' values lower than "1" are expressed in percentages;

FIGS. 3A-3C are contour map depicting spatial allele frequency distributions in Africa of the ESKD risk variants. FIG. 3A—MYH9 S-1 (SNP rs5750250); FIG. 3B—MYH9 F-1 SNP (rs11912763); FIG. 3C—APOL1 S342G missense mutation (rs73885319). Maps were generated based on genotyping of 12 African populations (n=676) (Table 3, in the Examples section which follows), using Surfer V.9 (Golden Software). Populations locations are marked (red circles for Ethiopia). Risk allele frequencies in Ethiopia and in South-Ghana are indicated;

FIGS. 4A-4C are predicted peptide structures of the C-terminus domain of the APOL1 gene product (amino acid positions 339-398 in SEQ ID NO:1) that contains the missense mutations S342G and I384M. All predictions were generated using the program I-TASSER (Zhang 2008, 2009), structures were edited with the program CHIMERA (Pettersen et al. 2004). All suggested predicted structures exhibit Tm values >0.5. FIG. 4A—Predicted structure and location of amino acid changes. C-terminus domain is predicted to have a bent alpha-helix structure. The mutation I384M is located on the external surface of the predicted alpha-helix, while the S342G is buried inside. FIG. 4B—Hydrophobicity of the predicted peptide surface (RED-hydrophobic amino-acids, BLUE-polar amino-acids). Hydrophobic core is predicted to stabilize the bent C-terminus helical structure. FIG. 4C—Identified binding site in the predicted structure of the APOL1 C-terminus domain (Zhang 2008, 2009), based on similarity to an analogous known binding site (Billas et al. 2003). S342G is involved in the predicted binding site domain, and is predicted to modify its binding ability.

FIGS. 5A-5D are schematic pie charts depicting allele frequencies for the APOL1 SNP rs73885319 (S342G) in African Americans and Hispanic Americans ESKD cases versus controls. "G" refers to the risk allele and "A" refers to the "protective" allele; FIG. 5A—Controls African Americans; FIG. 5B (Cases African Americas); FIG. 5C (Controls, Hispanic Americans); FIG. 5D (Cases, Hispanic Americans). Note the high prevalence of the risk allele (G) among African American controls as compared to Hispanic Americans controls, and the significant increase in frequency of the risk allele among both African Americans and Hispanic Americans controls.

Figure 6:
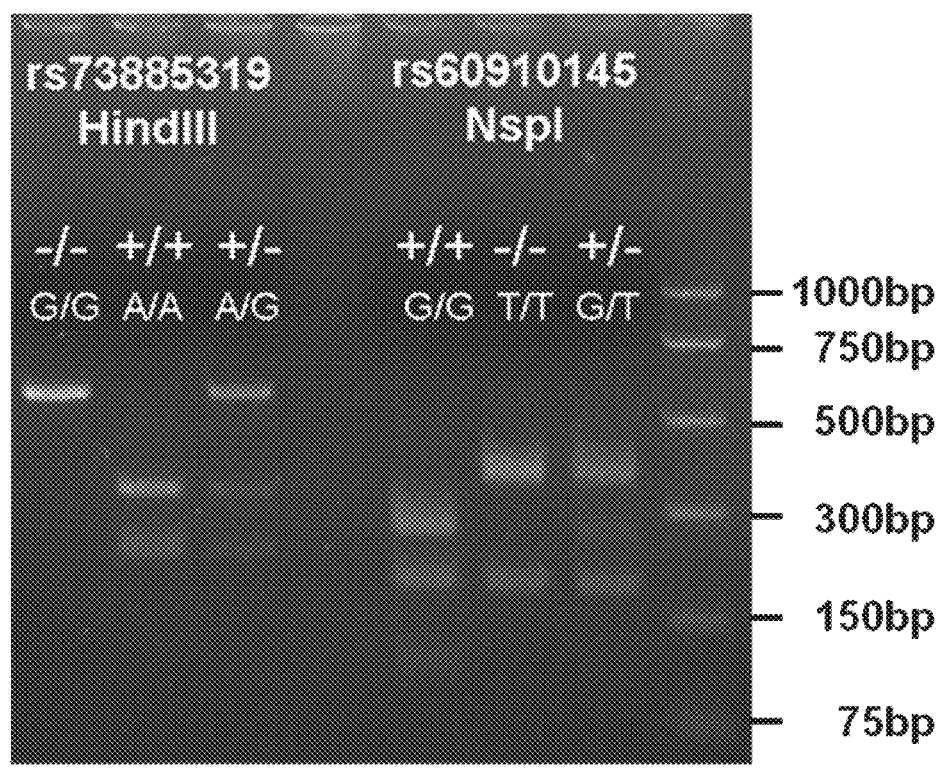

FIG. 6 is a gel image depicting results of restriction fragments length polymorphism (RFLP) analysis for APOL1 missense mutations SNP rs73885319 (S342G) and SNP rs60910145 (I384M). Shown are the restriction fragments resulted from digestion of DNA with the HindIII and NSPI restriction enzymes. SNP APOL1 rs73885319 A/G: The allele containing G eliminates a recognition site of endonuclease HindIII. APOL1 SNP rs60910145 T/G: The allele containing T generates a new recognition site of endonuclease NspI. The sign '+' indicates an additional cutting site in the DNA fragment due to the presence of the mutation. The sign '-' indicates no additional cutting site in the DNA fragment.

DESCRIPTION OF SPECIFIC EMBODIMENTS OF THE INVENTION

The present invention, in some embodiments thereof, relates to methods and kits for determining predisposition to develop a kidney disease, and, more particularly, but not exclusively, to methods of designing a life-style change and/or a treatment regimen in predisposed subjects.

Before explaining at least one embodiment of the invention in detail, it is to be understood that the invention is not necessarily limited in its application to the details set forth in the following description or exemplified by the Examples. The invention is capable of other embodiments or of being practiced or carried out in various ways.

The present inventors have uncovered that SNPs in the APOL1 gene are highly associated with renal disease and therefore identification of the APOL1 risk alleles can be used to determine predisposition to renal diseases.

Thus, as described in the Examples section which follows, the present inventors have uncovered that two Western African specific mis sense mutations (S342G and I384M) in the APOL1 gene/polypeptide are more strongly associated with ESKD than previously reported MYH9 variants (Example 1, Tables 1 and 3, FIGS. 1, 2 and 5A-D). In addition, the present inventors have uncovered that the distribution of these risk variants in African populations is consistent with the pattern of African ancestry ESKD risk previously attributed to MYH9 (Example 2, Table 3, FIGS. 3A-C). These results demonstrate that the functional polymorphisms in the APOL1 protein account for the increased susceptibility of the African American population to develop renal disease such as ESKD, and suggest the use of these markers as diagnostic and prognostic markers for diagnosing renal diseases and for designing life style change and treatment regimens to subjects at risk of renal disease based on the presence or absence of the predisposition to develop the renal disease.

Thus, according to an aspect of some embodiments of the invention there is provided a method of determining predisposition of a subject to develop a kidney disease. The method comprising identifying in a sample of the subject at least one APOL1 polypeptide variant which is characterized by a higher trypanolytic activity on *Trypanosoma brucei rhodesiense* as compared to the trypanolytic activity of wild type APOL1 polypeptide as set forth in SEQ ID NO:1 on the *Trypanosoma brucei rhodesiense* under identical assay conditions, wherein presence of the APOL1 polypeptide variant indicates increased predisposition of the subject to develop the kidney disease, thereby determining the predisposition of the subject to develop the kidney disease.

As used herein the term "predisposition" refers to the tendency of a subject to develop a certain condition (e.g., a kidney disease).

According to some embodiments of the invention, the predisposition which is determined by the method of some embodiments of the invention is a genetic predisposition, i.e., predisposition to develop a condition due to a certain genetic background as compared to a subject devoid of such genetic background.

It should be noted that a subject who is predisposed to develop a disease (e.g., kidney disease) is more likely to develop the disease than a non-predisposed subject.

The predisposition to develop the kidney disease can be quantified by generating and using genotype relative risk (GRR) values. The GRR is the increased chance of an individual with a particular genotype to develop the disease. Thus, the GRR of the risk genotype G, with respect to the protective genotype Go, is the ratio between the risk of an individual carrying genotype G to develop the disease, and the risk of an individual carrying genotype Go to develop the disease. The GRR used herein is represented in terms of an appropriate odds ratio (OR) of G versus Go in cases and controls. Moreover, computation of GRR of genotypes or haplotypes is based on a multiplicative model in which the GRR of an homozygote individual is the square of the GRR of an heterozygote individual. For further details see Risch and Merikangas, 1996 [The future of genetic studies of complex human diseases. Science 273: 1516-1517], which is incorporated herein by reference in its entirety.

Once calculated, the GRR can reflect the increased predisposition risk on an individual with a specific APOL1 genotype to develop the kidney disease.

As used herein the phrase "APOL1 polypeptide variant" refers to an APOL1 amino acid sequence which comprises at least one amino acid change with respect to the wild type APOL1 polypeptide set forth by SEQ ID NO:1. The amino acid change can be an amino acid(s) substitution, deletion or insertion. The amino acid substitution can be a conservative substitution, i.e., with a similar amino acid (e.g., a positively charged amino acid is replaced by another positively charged amino acid; a hydrophobic amino acid is replaced by another hydrophobic amino acid; a negatively-charged amino acid is replaced by another negatively charged amino acid), or it can be a non-conservative substitution, i.e., with an amino acid having different characteristics (e.g., a positively charged amino acid is replaced by a negatively charged amino acid; a hydrophobic amino acid is replaced by a positively-charged amino acid; a negatively-charged amino acid is replaced by a hydrophobic amino acid, etc.).

It should be noted that the amino acid change can include one or more amino acids of the APOL1 polypeptide set forth by SEQ ID NO:1.

It should be noted that the "wild type APOL1 polypeptide" comprises "S" (Serine) at amino acid position 342 in SEQ ID NO:1, "I" (Isoleucine) at amino acid position 384 in SEQ ID NO:1, "N" (Asparagine) at amino acid position 388 in SEQ ID NO:1 and "Y" (Tyrosine) at amino acid position 389 in SEQ ID NO:1.

According to some embodiments of the invention, the APOL1 variant comprises only one amino acid change with respect to the wild type APOL1 polypeptide set forth by SEQ ID NO:1.

According to some embodiments of the invention, the APOL1 variant comprises two amino acid changes with respect to the wild type APOL1 polypeptide set forth by SEQ ID NO:1.

According to some embodiments of the invention, the APOL1 variant comprises at least one amino acid change and no more than about 60 amino acid changes with respect to the wild type APOL1 polypeptide set forth by SEQ ID NO:1.

According to some embodiments of the invention, the APOL1 variant comprises about 2-20 (e.g., 2, 3, 4, 5, 6, 7, 8, 9, 10, 11, 12, 13, 14, 15, 16, 17, 18, 19 or 20) amino acid changes with respect to the wild type APOL1 polypeptide set forth by SEQ ID NO:1.

According to some embodiments of the invention, the APOL1 polypeptide variant comprises a mutation (missense, nonsense, deletion or insertion) in the C-terminal helix of the APOL1 polypeptide. According to some embodiments of the invention, the amino acid change(s) in APOL1 variant occurs in the SRA-interacting domain in the C-terminal end of the APOL1 polypeptide, between amino acids 339-398 of SEQ ID NO:1 (FIG. 1 of Lecordier et al., 2009, PLoS Pathog. 2009 December; 5(12): e1000685).

According to some embodiments of the invention, the amino acid change(s) in APOL1 variant does not occur within the pore forming domain (amino acids 60-238 of SEQ ID NO:1) and/or within the membrane-addressing domain (amino acids 238-304 of SEQ ID NO:1).

As described, the APOL1 polypeptide variant which is identified by the method of some embodiments of the invention is characterized by a higher trypanolytic activity on *Trypanosoma brucei rhodesiense* as compared to the trypanolytic activity of wild type APOL1 polypeptide as set forth in SEQ ID NO:1 on the *Trypanosoma brucei rhodesiense* under identical assay conditions.

According to some embodiments of the invention, the *Trypanosoma brucei rhodesiense* is resistant to lysis by the apolipoprotein present in normal human serum.

According to some embodiments of the invention, the *Trypanosoma brucei rhodesiense* expresses serum resistance-associated protein (SRA), also referred to as SRA-positive.

It should be noted that wild type APOL1 fails to lyse the SRA+(positive) *Trypanosoma brucei rhodesiense* (See for example, FIG. 3C in Genovese G., et al. "Association of Trypanolytic APOL1 variants with kidney disease in African-Americans", Science 2010, 329: 841-845, which is fully incorporated herein by reference).

As used herein the phrase "higher trypanolytic activity" refers to at least about 10%, at least about 15%, 20%, 25%, 30%, 40%, 45%, 50%, 55%, 60%, 65%, 70%, 75%, 80%, 85%, 90%, 95%, or 99% greater trypanolytic activity of the APOL1 polypeptide variant as compared to the trypanolytic activity of wild type APOL1 polypeptide as set forth in SEQ ID NO:1.

According to some embodiments of the invention, the APOL1 polypeptide variant which exhibits a higher trypanolytic activity as compared to the APOL1 wild type polypeptide set forth by SEQ ID NO:1 is selected from the group G342, M384, N388-del and Y389-del (positions refer to the APOL1 polypeptide sequence set forth in SEQ ID NO:1).

According to some embodiments of the invention, the APOL1 polypeptide variant is APOL1 N388-del/Y389-del (numbers relate to the APOL1 polypeptide sequence set forth in SEQ ID NO:1).

The sample used according to the method of this aspect of the invention can be any biological sample (obtained from an individual, e.g., human) which comprises the APOL1 polypeptide, or a sample of a recombinant or synthetic APOL1 polypeptide. Examples of biological samples include, but are not limited to whole blood or fractions thereof, such as serum, lipoproteins [High-density lipoprotein (HDL)], body fluids and exertions, tissue samples, and the like. The sample can be at least partially isolated from the subject, and further purified, or can be a crude sample.

According to some embodiments of the invention the sample is a serum sample.

According to some embodiments of the invention the sample is plasma HDL.

The trypanolytic activity can be measured as the percentage of survival of the trypanosome in the presence of a sample containing the APOL1 polypeptide. Thus, for example, while in the presence of the wild type APOL1 polypeptide set forth in SEQ ID NO:1 the percentage of survival can be about 100%, in the presence of an APOL1 variant the percentage of survival of the trypanosome can be reduced to 80%, 60%, 40%, 20% and 0% survival, which is referred to as 20%, 40%, 60%, 80% and 100% trypanolytic activity of the APOL1 polypeptide, respectively.

Assays which can be used to measure the trypanolytic activity of a protein on *Trypanosoma brucei rhodesiense* are known in the art and described, for example in Lecordier L, et al. "C-terminal mutants of apolipoprotein L-I efficiently kill both *Trypanosoma brucei brucei* and *Trypanosoma brucei rhodesiense*." PLoS Pathog. 2009 December; 5(12): e1000685. Epub 2009 Dec. 4; U.S. Patent Application No. 20110030078; Genovese G., et al. "Association of Trypanolytic APOL1 variants with kidney disease in African-Americans", Science 2010, 329: 841-845; and in Tomlinson, et al., "High-density-lipoprotein-independent Killing of *Trypanosoma brucei brucei* by Human Serum," Mol. Biochem. Parasitol. 70:131-138 (1995), each of which is hereby incorporated by reference in its entirety.

Following is a non-limiting description of an in vitro assays which can be used to determine the trypanolytic activity of the APOL1 variant. Samples containing the APOL1 polypeptide can be for example, serum samples, plasma HDL or recombinant APOL1 polypeptides. Serum samples can be obtained by simple blood drawing and separation of serum from the blood. Plasma HDLs can be prepared by density gradient centrifugation and gel filtration. Recombinant APOL1 polypeptides [wild type APOL1 (SEQ ID NO:1) or APOL1 polypeptide variants (e.g., the G342, M384, N388-del and/or Y389-del APOL1 polypeptide variant)] can be expressed from a nucleic acid construct comprising the coding sequence of APOL1 which is expressed in prokaryotic (e.g., *Escherichia coli*) or eukaryotic (e.g., 293T) cells essentially as described in Lecordier L, et al. 2009 (Supra).

The trypanolytic activity is determined in *Trypanosoma brucei rhodesiense*. There are two major types of *Trypanosoma brucei rhodesiense* clones: the normal human serum-resistant (SRA+) and the normal human serum-sensitive (SRA-) T. b. *rhodesiense* ETat 1.2 clones can be used. ETat 1.2R is resistant to normal human serum, and ETat 1.2S is sensitive to normal human serum. It should be noted that while the SRA-T. b. *rhodesiense* (sensitive) clone is used as a positive control for the trypanolytic activity by all forms of APOL1 polypeptides (wild type and variant APOL1 polypeptides), the SRA+T. b. *rhodesiense* (resistance) is used to differentiate between the APOL1 variants which are capable of lysing the *Trypanosoma brucei rhodesiense* and the wild type APOL1 polypeptide set forth in SEQ ID NO:1 which is incapable of lysing the *Trypanosoma brucei rhodesiense* as can be determined by a survival assay as described below. The trypanosomes can be diluted into pre-warmed DMEM containing 10% fetal bovine serum (FBS). In 96-well plates, serum samples are diluted into DMEM+10% fetal calf serum (FCS) and trypanosomes are added to a final volume of 0.2 ml, containing about $2.5 \times 10^5$/ml parasites. Killing is allowed to proceed for about 17 hours at 37° C. in a $CO_2$ equilibrated incubator and living trypanosomes are counted using a heamocytometer. HDL killing assays are performed for 150 minutes at 37° C. in DMEM, 0.2% BSA using aliquots of sized fractionated lipoproteins incubated with parasites (*trypanosoma*) diluted at a final concentration of about $5 \times 10^5$ cells/ml. Parasite lysis can be determined using a calcein-AM fluorescence-based assay (Tomlinson et al., "High-density-lipoprotein-independent Killing of *Trypanosoma brucei* by Human Serum," Mol Biochem Parasitol 70: 131-8 (1995), which is hereby incorporated by reference in its entirety). Recombinant APOL1 polypeptides (e.g., about 0.1-20 µg/ml, e.g., about 0.6-10 µg/ml, e.g., about 0.6-5 µg/ml) can be incubated with the *trypanosoma* overnight and the survival of *trypanosoma* can be determined and expressed as percentage (%) survival as compared to control (e.g., FCS).

According to some embodiments of the invention, the APOL1 polypeptide variant has a reduced binding ability to serum resistance-associated protein (SRA) expressed by

*Trypanosoma brucei rhodesiense* as compared to the binding ability of the APOL1 wild type polypeptide under identical assay conditions.

Assays of measuring the binding ability of the APOL1 polypeptide to *Trypanosoma brucei rhodesiense* SRA are known in the art and are described for example, in Genovese G., et al. "Association of Trypanolytic APOL1 variants with kidney disease in African-Americans", Science 2010, 329: 841-845, which is hereby incorporated herein by its entirety.

Determination of predisposition of a subject to develop a kidney disease can be also performed by single nucleotide polymorphism detection methods.

According to an aspect of some embodiments of the invention there is provided a method of determining predisposition of a subject to develop a kidney disease, comprising: identifying in a sample of the subject at least one APOL1 nucleotide mutation in the APLO1 genomic sequence set forth in SEQ ID NO:3 (chr22:36,622,000-36,677,000 in NCBI37.1/hg19 assembly) or at least one APOL1 polypeptide variant, wherein the at least one nucleotide mutation or polypeptide variant being in linkage disequlibrium (LD) with the S342G mutation in the APOL1 polypeptide set forth in SEQ ID NO:1, wherein presence of the APOL1 nucleotide mutation or the APOL1 polypeptide variant indicates increased predisposition of the subject to develop the kidney disease, thereby determining the predisposition of the subject to develop the kidney disease.

The sample according to some embodiments of the invention is a DNA or protein sample.

The DNA sample can be obtained from any source of cells of the individual, including, but not limited to, peripheral blood cells (obtained using a syringe), skin cells (obtained from a skin biopsy), saliva or mouth epithelial cells (obtained from a mouth wash), and body secretions such as urine and tears, and from biopsies, etc. Alternatively, nucleic acid tests can be performed on dry samples (e.g. hair or skin).

The sample may contain genomic DNA, cDNA or RNA. Methods of preparing genomic DNA or cDNA and RNA are well known in the art.

According to some embodiments of the invention, the DNA sample is obtained from a peripheral blood sample. Methods of extracting DNA from blood samples are well known in the art.

Once obtained, the DNA sample is preferably characterized for the presence or absence of at least one or more of the APOL1 nucleotide mutations in a homozygous or a heterozygous form in the sample of the subject.

The term "absence" as used herein in regard to the nucleotide or protein mutation describes the negative result of a specific genotype determination test. For example, if the genotype determination test is suitable for the identification of guanine nucleotide—containing allele of SNP rs73885319 (encoding APOL1 G342), and the individual on which the test is performed is homozygote for the adenosine nucleotide—containing allele of SNP rs73885319 (encoding APOL1 S342), then the result of the test will be "absence of nucleotide or protein mutation".

The terms "homozygous" or "heterozygous" refer to two identical or two different alleles, respectively, of a certain mutation or polymorphism.

The phrases "APOL1 nucleotide mutation" or "APOL1 single nucleotide polymorphism (SNP)", which are interchangeably used herein, refer to a substitution, deletion, insertion or inversion of a nucleotide sequence in the APOL1 genomic sequence with respect to the wild type genomic sequence set forth in SEQ ID NO:3.

It should be noted that the APOL1 mutation can be a substitution, deletion, insertion or inversion of a nucleotide sequence in the APOL1 coding sequence with respect to the wild type APOL1 mRNA sequence set forth in SEQ ID NO:2 (GenBank Accession No. NM_001136540.1); or it can be a missense, nonsense, deletion or insertion resulting in a mutant APOL1 polypeptide with respect to the wild type polypeptide sequence set forth in SEQ ID NO:1 (GenBank Accession No. NP_003652.2).

It should be noted that "wild type APOL1 mRNA sequence" comprises "A" (adenosine nucleotide) at nucleotide position 1231 in SEQ ID NO:2, "T" (thymidine nucleotide) at position 1359 in SEQ ID NO:2, "ATT" at nucleotide positions 1369-1371 in SEQ ID NO:2, "ATA" at nucleotide positions 1372-1374 in SEQ ID NO:2, and "T" (thymidine nucleotide) at nucleotide position 2538 in SEQ ID NO:2.

It should be noted that the "wild type APOL1 genomic sequence" comprises "A" (adenosine nucleotide) at nucleotide position 34556 in SEQ ID NO:3, "A" (adenosine nucleotide) at nucleotide position 39907 in SEQ ID NO:3, "T" (thymidine nucleotide) at nucleotide position 40035 in SEQ ID NO:3, "AAT" at nucleotide positions 40045-40047 in SEQ ID NO:3, "TAT" at nucleotide positions 40048-40050 in SEQ ID NO:3, "T" (thymidine nucleotide) at nucleotide position 41214 in SEQ ID NO:3, and "G" (guanine nucleotide) at nucleotide position 45155 in SEQ ID NO:3.

The APOL1 mutation can be a missense mutation (i.e., a mutation which changes an amino acid residue in the protein with another amino acid residue), a nonsense mutation (i.e., a mutation which introduces a stop codon in a protein), a frameshift mutation (i.e., a mutation, usually, deletion or insertion of nucleic acids which changes the reading frame of the protein, and may result in an early termination or in a longer amino acid sequence), a readthrough mutation (i.e., a mutation which results in an elongated protein due to a change in a coding frame or a modified stop codon), a promoter mutation (i.e., a mutation in a promoter sequence, usually 5' to the transcription start site of a gene, which result in up-regulation or down-regulation of a specific gene product), a regulatory mutation (i.e., a mutation in a region upstream or downstream, or within a gene, which affects the expression of the gene product), a deletion (i.e., a mutation which deletes coding or non-coding nucleic acids in a gene sequence), an insertion (i.e., a mutation which inserts coding or non-coding nucleic acids into a gene sequence), an inversion (i.e., a mutation which results in an inverted coding or non-coding sequence), and a duplication (i.e., a mutation which results in a duplicated coding or non-coding sequence).

According to some embodiments of the invention, the at least one mutation comprises no more than about 100, no more than about 90, no more than about 80, no more than about 70, no more than about 60, no more than about 50, no more than about 40, no more than about 30, no more than about 20, no more than about 15, no more than about 10, e.g., no more than 9, 8, 7, 6, 5, 4, 3, 2 nucleotide mutations in the APOL1 genomic sequence with respect to the wild type genomic sequence set forth in SEQ ID NO:3.

According to some embodiments of the invention, the at least one mutation comprises no more than about 100, no more than about 90, no more than about 80, no more than about 70, no more than about 60, no more than about 50, no more than about 40, no more than about 30, no more than about 20, no more than about 15, no more than about 10, e.g., no more than 9, 8, 7, 6, 5, 4, 3, 2 nucleotide mutations in the APOL1 coding sequence with respect to the wild type coding sequence set forth in SEQ ID NO:2.

According to some embodiments of the invention, the at least one mutation comprises no more than about 100, no more than about 90, no more than about 80, no more than about 70, no more than about 60, no more than about 50, no more than about 40, no more than about 30, no more than about 20, no more than about 15, no more than about 10, e.g., no more than 9, 8, 7, 6, 5, 4, 3, 2 amino acid mutations in the APOL1 genomic sequence with respect to the wild type polypeptide sequence set forth in SEQ ID NO:1.

As described, the nucleotide mutation is in linkage disequilibrium with the S342G mutation in the APOL1 polypeptide set forth in SEQ ID NO:1, which is encoded by the AG (adenosine to guanine) substitution at position 1231 of the APOL1 mRNA (coding sequence) set forth by SEQ ID NO:2.

The phrase "linkage disequilibrium" (LD) is used to describe the statistical correlation between two neighboring polymorphic genotypes. Typically, LD refers to the correlation between the alleles of a random gamete at the two loci, assuming Hardy-Weinberg equilibrium (statistical independence) between gametes. LD is quantified with either Lewontin's parameter of association (D') or with Pearson correlation coefficient (r) [Devlin B, Risch N. (1995). A comparison of linkage disequilibrium measures for fine-scale mapping. Genomics. 29: 311-322.]. Two loci with a LD value of 1 are the to be in complete LD. At the other extreme, two loci with a LD value of 0 are termed to be in linkage equilibrium. Linkage disequilibrium is calculated following the application of the expectation maximization algorithm (EM) for the estimation of haplotype frequencies [Slatkin M, Excoffier L. (1996). Testing for linkage disequilibrium in genotypic data using the Expectation-Maximization algorithm. Heredity. 76: 377-83.]. Preferably, LD values according to the present invention for neighboring genotypes/loci are selected above 0.1, preferably, above 0.2, more preferable above 0.5, more preferably, above 0.6, still more preferably, above 0.7, preferably, above 0.8, more preferably above 0.9, ideally about 1.0.

In the D-Prime Plot, each diagonal represents a different SNP, with each square representing a pairwise comparison between two SNPs. SNPs are numbered sequentially, 5' to 3', and their relative location is indicated along the top. Red squares indicate statistically significant (LOD>2) allelic association (linkage disequilibrium, LD) between the pair of SNPs, as measured by the D' statistic; darker colors of red indicate higher values of D', up to a maximum of 1. White squares indicate pairwise D' values of <1 with no statistically significant evidence of LD. Blue squares indicate pairwise D' values of 1 but without statistical significance.

According to some embodiments of the invention, the LD between the APOL1 nucleotide mutation and the S342G mutation is characterized by a Lewontin correlation coefficient (D') higher than about 0.5, e.g., higher than about 0.6, higher than about 0.7, higher than about 0.8, higher than about 0.9, higher than about 0.91, higher than about 0.92, higher than about 0.93, higher than about 0.94, higher than about 0.95, higher than about 0.96, higher than about 0.97, higher than about 0.98, higher than about 0.99, e.g., about 1.0.

According to some embodiments of the invention, the significance of the LD is characterized by LOD≥2, e.g., LOD≥3, LOD≥4, LOD≥5, LOD≥6, LOD≥7.

As shown in FIG. 2, and described in Example 1 of the Examples section which follows, and based on the 1000-genomes-project (Hypertext Transfer Protocol://World Wide Web (dot)1000genomes(dot)org/) the present inventors have uncovered that the rs9622363, rs58384577, rs73885319 and rs60910145 SNPs are in complete LD (D'/LOD=100), and that the rs60295735 SNP is in tight linkage disequilibrium with each of them [i.e., D'/LOD (in percentages)=91 (with rs9622363), 95 (with rs73885319) and 97 (with rs60910145)].

According to some embodiments of the invention, the APOL1 nucleotide mutation is selected from the group consisting of the guanine-containing allele of single nucleotide polymorphism (SNP) rs73885319 (SEQ ID NO:6), the guanine-containing allele of SNP rs60910145 (SEQ ID NO:7), the guanine-containing allele of SNP rs9622363 (SEQ ID NO:8), the adenine-containing allele of SNP rs60295735 (SEQ ID NO:9) and the cytosine-containing allele of SNP rs58384577 (SEQ ID NO:10).

According to some embodiments of the invention, the nucleotide mutation creates an APOL1 protein variant.

The SNPs of some embodiments of the invention can be identified using a variety of approaches suitable for identifying sequence alterations. One option is to determine the entire gene sequence of a PCR reaction product. Alternatively, a given segment of nucleic acid may be characterized on several other levels. At the lowest resolution, the size of the molecule can be determined by electrophoresis by comparison to a known standard run on the same gel. A more detailed picture of the molecule may be achieved by cleavage with combinations of restriction enzymes prior to electrophoresis, to allow construction of an ordered map. The presence of specific sequences within the fragment can be detected by hybridization of a labeled probe, or the precise nucleotide sequence can be determined by partial chemical degradation or by primer extension in the presence of chain-terminating nucleotide analogs.

Following is a non-limiting list of SNPs detection methods which can be used to identify one or more of the SNPs of some embodiments of the invention.

Restriction fragment length polymorphism (RFLP): This method uses a change in a single nucleotide (the SNP nucleotide) which modifies a recognition site for a restriction enzyme resulting in the creation or destruction of an RFLP. Single nucleotide mismatches in DNA heteroduplexes are also recognized and cleaved by some chemicals, providing an alternative strategy to detect single base substitutions, generically named the "Mismatch Chemical Cleavage" (MCC) (Gogos et al., Nucl. Acids Res., 18:6807-6817, 1990). However, this method requires the use of osmium tetroxide and piperidine, two highly noxious chemicals which are not suited for use in a clinical laboratory.

Allele specific oligonucleotide (ASO): In this method, an allele-specific oligonucleotide (ASO) is designed to hybridize in proximity to the polymorphic nucleotide, such that a primer extension or ligation event can be used as the indicator of a match or a mis-match. Hybridization with radioactively labeled allelic specific oligonucleotides (ASO) also has been applied to the detection of specific SNPs (Conner et al., Proc. Natl. Acad. Sci., 80:278-282, 1983). The method is based on the differences in the melting temperature of short DNA fragments differing by a single nucleotide. Stringent hybridization and washing conditions can differentiate between mutant and wild-type alleles.

Denaturing/Temperature Gradient Gel Electrophoresis (DGGE/TGGE): Two other methods rely on detecting changes in electrophoretic mobility in response to minor sequence changes. One of these methods, termed "Denaturing Gradient Gel Electrophoresis" (DGGE) is based on the observation that slightly different sequences will display different patterns of local melting when electrophoretically resolved on a gradient gel. In this manner, variants can be distinguished, as differences in melting properties of homoduplexes versus heteroduplexes differing in a single nucleotide can detect the presence of SNPs in the target sequences because of the corresponding changes in their electrophoretic mobilities. The fragments to be analyzed, usually PCR products, are "clamped" at one end by a long stretch of G-C base pairs (30-80) to allow complete denaturation of the sequence of interest without complete dissociation of the strands. The attachment of a GC "clamp" to the DNA fragments increases the fraction of mutations that can be recognized by DGGE (Abrams et al., Genomics 7:463-475, 1990). Attaching a GC clamp to one primer is critical to ensure that the amplified sequence has a low dissociation temperature (Sheffield et al., Proc. Natl. Acad. Sci., 86:232-236, 1989; and Lerman and Silverstein, Meth. Enzymol., 155:482-501, 1987). Modifications of the technique have been developed, using temperature gradients (Wartell et al., Nucl. Acids Res., 18:2699-2701, 1990), and the method can be also applied to RNA:RNA duplexes (Smith et al., Genomics 3:217-223, 1988).

Limitations on the utility of DGGE include the requirement that the denaturing conditions must be optimized for each type of DNA to be tested. Furthermore, the method requires specialized equipment to prepare the gels and maintain the needed high temperatures during electrophoresis. The expense associated with the synthesis of the clamping tail on one oligonucleotide for each sequence to be tested is also a major consideration. In addition, long running times are required for DGGE. The long running time of DGGE was shortened in a modification of DGGE called constant denaturant gel electrophoresis (CDGE) (Borrensen et al., Proc. Natl. Acad. Sci. USA 88:8405, 1991). CDGE requires that gels be performed under different denaturant conditions in order to reach high efficiency for the detection of SNPs.

A technique analogous to DGGE, termed temperature gradient gel electrophoresis (TGGE), uses a thermal gradient rather than a chemical denaturant gradient (Scholz, et al., Hum. Mol. Genet. 2:2155, 1993). TGGE requires the use of specialized equipment which can generate a temperature gradient perpendicularly oriented relative to the electrical field. TGGE can detect mutations in relatively small fragments of DNA therefore scanning of large gene segments requires the use of multiple PCR products prior to running the gel.

Single-Strand Conformation Polymorphism (SSCP): Another common method, called "Single-Strand Conformation Polymorphism" (SSCP) was developed by Hayashi, Sekya and colleagues (reviewed by Hayashi, PCR Meth. Appl., 1:34-38, 1991) and is based on the observation that single strands of nucleic acid can take on characteristic conformations in non-denaturing conditions, and these conformations influence electrophoretic mobility. The complementary strands assume sufficiently different structures that one strand may be resolved from the other. Changes in sequences within the fragment will also change the conformation, consequently altering the mobility and allowing this to be used as an assay for sequence variations (Orita, et al., Genomics 5:874-879, 1989).

The SSCP process involves denaturing a DNA segment (e.g., a PCR product) that is labeled on both strands, followed by slow electrophoretic separation on a non-denaturing polyacrylamide gel, so that intra-molecular interactions can form and not be disturbed during the run. This technique is extremely sensitive to variations in gel composition and temperature. A serious limitation of this method is the relative difficulty encountered in comparing data generated in different laboratories, under apparently similar conditions.

Dideoxy fingerprinting (ddF): The dideoxy fingerprinting (ddF) is another technique developed to scan genes for the presence of mutations (Liu and Sommer, PCR Methods Appli., 4:97, 1994). The ddF technique combines components of Sanger dideoxy sequencing with SSCP. A dideoxy sequencing reaction is performed using one dideoxy terminator and then the reaction products are electrophoresed on nondenaturing polyacrylamide gels to detect alterations in mobility of the termination segments as in SSCP analysis. While ddF is an improvement over SSCP in terms of increased sensitivity, ddF requires the use of expensive dideoxynucleotides and this technique is still limited to the analysis of fragments of the size suitable for SSCP (i.e., fragments of 200-300 bases for optimal detection of mutations).

In addition to the above limitations, all of these methods are limited as to the size of the nucleic acid fragment that can be analyzed. For the direct sequencing approach, sequences of greater than 600 base pairs require cloning, with the consequent delays and expense of either deletion sub-cloning or primer walking, in order to cover the entire fragment. SSCP and DGGE have even more severe size limitations. Because of reduced sensitivity to sequence changes, these methods are not considered suitable for larger fragments. Although SSCP is reportedly able to detect 90% of single-base substitutions within a 200 base-pair fragment, the detection drops to less than 50% for 400 base pair fragments. Similarly, the sensitivity of DGGE decreases as the length of the fragment reaches 500 base-pairs. The ddF technique, as a combination of direct sequencing and SSCP, is also limited by the relatively small size of the DNA that can be screened.

Pyrosequencing™ analysis (Pyrosequencing, Inc. Westborough, Mass., USA): This technique is based on the hybridization of a sequencing primer to a single stranded, PCR-amplified, DNA template in the presence of DNA polymerase, ATP sulfurylase, luciferase and apyrase enzymes and the adenosine 5' phosphosulfate (APS) and luciferin substrates. In the second step the first of four deoxynucleotide triphosphates (dNTP) is added to the reaction and the DNA polymerase catalyzes the incorporation of the deoxynucleotide triphosphate into the DNA strand, if it is complementary to the base in the template strand. Each incorporation event is accompanied by release of pyrophosphate (PPi) in a quantity equimolar to the amount of incorporated nucleotide. In the last step the ATP sulfurylase quantitatively converts PPi to ATP in the presence of adenosine 5' phosphosulfate. This ATP drives the luciferase-mediated conversion of luciferin to oxyluciferin that generates visible light in amounts that are proportional to the amount of ATP. The light produced in the luciferase-catalyzed reaction is detected by a charge coupled device (CCD) camera and seen as a peak in a Pyrogram™. Each light signal is proportional to the number of nucleotides incorporated.

Acycloprime™ analysis (Perkin Elmer, Boston, Mass., USA): This technique is based on fluorescent polarization (FP) detection. Following PCR amplification of the sequence containing the SNP of interest, excess primer and dNTPs are removed through incubation with shrimp alkaline phosphatase (SAP) and exonuclease I. Once the enzymes are heat inactivated, the Acycloprime-FP process uses a thermostable polymerase to add one of two fluorescent terminators to a primer that ends immediately upstream of the SNP site. The terminator(s) added are identified by their increased FP and represent the allele(s) present in the original DNA sample. The Acycloprime process uses AcycloPol™, a novel mutant thermostable polymerase from the Archeon family, and a pair of AcycloTerminators™ labeled with R110 and TAMRA, representing the possible alleles for the SNP of interest. AcycloTerminator™ non-nucleotide analogs are biologically active with a variety of DNA polymerases. Similarly to 2', 3'-dideoxynucleotide-5'-triphosphates, the acyclic analogs function as chain terminators. The analog is incorporated by the DNA polymerase in a base-specific manner onto the 3'-end of the DNA chain, and since there is no 3'-hydroxyl, is unable to function in further chain elongation. It has been found that AcycloPol has a higher affinity and specificity for derivatized Acyclo-Terminators than various Taq mutant have for derivatized 2',3'-dideoxynucleotide terminators.

Reverse dot blot: This technique uses labeled sequence specific oligonucleotide probes and unlabeled nucleic acid samples. Activated primary amine-conjugated oligonucleotides are covalently attached to carboxylated nylon membranes. After hybridization and washing, the labeled probe, or a labeled fragment of the probe, can be released using oligomer restriction, i.e., the digestion of the duplex hybrid with a restriction enzyme. Circular spots or lines are visualized colorimetrically after hybridization through the use of streptavidin horseradish peroxidase incubation followed by development using tetramethylbenzidine and hydrogen peroxide, or via chemiluminescence after incubation with avidin alkaline phosphatase conjugate and a luminous substrate susceptible to enzyme activation, such as CSPD, followed by exposure to x-ray film.

It will be appreciated that advances in the field of SNP detection have provided additional accurate, easy, and inexpensive large-scale SNP genotyping techniques, such as dynamic allele-specific hybridization (DASH, Howell, W. M. et al., 1999. Dynamic allele-specific hybridization (DASH). Nat. Biotechnol. 17: 87-8), microplate array diagonal gel electrophoresis [MADGE, Day, I. N. et al., 1995. High-throughput genotyping using horizontal polyacrylamide gels with wells arranged for microplate array diagonal gel electrophoresis (MADGE). Biotechniques. 19: 830-5], the TaqMan system (Holland, P. M. et al., 1991. Detection of specific polymerase chain reaction product by utilizing the 5'→3' exonuclease activity of *Thermus aquaticus* DNA polymerase. Proc Natl Acad Sci USA. 88: 7276-80), as well as various DNA "chip" technologies such as the GeneChip microarrays (e.g., Affymetrix SNP chips) which are disclosed in U.S. Pat. No. 6,300,063 to Lipshutz, et al. 2001, which is fully incorporated herein by reference, Genetic Bit Analysis (GBA™) which is described by Goelet, P. et al. (PCT Appl. No. 92/15712), peptide nucleic acid (PNA, Ren B, et al., 2004. Nucleic Acids Res. 32: e42) and locked nucleic acids (LNA, Latorra D, et al., 2003. Hum. Mutat. 22: 79-85) probes, Molecular Beacons (Abravaya K, et al., 2003. Clin Chem Lab Med. 41: 468-74), intercalating dye [Germer, S. and Higuchi, R. Single-tube genotyping without oligonucleotide probes. Genome Res. 9:72-78 (1999)], FRET primers (Solinas A et al., 2001. Nucleic Acids Res. 29: E96), AlphaScreen (Beaudet L, et al., Genome Res. 2001, 11(4): 600-8), SNPstream (Bell P A, et al., 2002. Biotechniques. Suppl.: 70-2, 74, 76-7), Multiplex minisequencing (Curcio M, et al., 2002. Electrophoresis. 23: 1467-72), SnaPshot (Turner D, et al., 2002. Hum Immunol. 63: 508-13), MassEXTEND (Cashman J R, et al., 2001. Drug Metab Dispos. 29: 1629-37), GOOD assay (Sauer S, and Gut IG. 2003. Rapid Commun. Mass. Spectrom. 17: 1265-72), Microarray minisequencing (Liljedahl U, et al., 2003. Pharmacogenetics. 13: 7-17), arrayed primer extension (APEX) (Tonisson N, et al., 2000. Clin. Chem. Lab. Med. 38: 165-70), Microarray primer extension (O'Meara D, et al., 2002. Nucleic Acids Res. 30: e75), Tag arrays (Fan J B, et al., 2000. Genome Res. 10: 853-60), Template-directed incorporation (TDI) (Akula N, et al., 2002. Biotechniques. 32: 1072-8), fluorescence polarization (Hsu™, et al., 2001. Biotechniques. 31: 560, 562, 564-8), Colorimetric oligonucleotide ligation assay (OLA, Nickerson D A, et al., 1990. Proc. Natl. Acad. Sci. USA. 87: 8923-7), Sequence-coded OLA (Gasparini P, et al., 1999. J. Med. Screen. 6: 67-9), Microarray ligation, Ligase chain reaction, Padlock probes, Rolling circle amplification, Invader assay (reviewed in Shi MM. 2001. Enabling large-scale pharmacogenetic studies by high-throughput mutation detection and genotyping technologies. Clin Chem. 47: 164-72), coded microspheres (Rao K V et al., 2003. Nucleic Acids Res. 31: e66) and MassArray (Leushner J, Chiu N H, 2000. Mol Diagn. 5: 341-80).

For example, as described under "GENERAL MATERIALS AND EXPERIMENTAL METHODS" in the Examples section which follows, determination of the SNPs was performed using the KasPar methodology (Petkov et al. 2004), as well as by PCR-RFLP [for SNP RS73885319 (S342G) and SNP RS60910145 (I384M)].

The protein sample can be obtained from any source of cells, tissues or body fluids of the individual. According to some embodiments of the invention, the protein sample is obtained from a blood sample (serum or plasma) of the individual. Methods of extracting proteins from blood samples are well known in the art. Once extracted, determination of the APOL1 polypeptide variants can be accomplished directly, by analyzing the protein gene products of the APOL1 gene, or portions thereof. Such a direct analysis is often accomplished using an immunological detection method.

Immunological detection methods: The immunological detection methods used in context of the present invention are fully explained in, for example, "Using Antibodies: A Laboratory Manual" [Ed Harlow, David Lane eds., Cold Spring Harbor Laboratory Press (1999)] and those familiar with the art will be capable of implementing the various techniques summarized hereinbelow as part of the present invention. All of the immunological techniques require antibodies specific to at least one of the two APOL1 alleles (the wild type allele and the APOL1 variant allele). Immunological detection methods suited for use as part of the present invention include, but are not limited to, radio-immunoassay (RIA), enzyme linked immunosorbent assay (ELISA), western blot, immunohistochemical analysis, and fluorescence activated cell sorting (FACS).

Radio-immunoassay (RIA): In one version, this method involves precipitation of the desired substrate, APOL1 in this case and in the methods detailed hereinbelow, with a specific antibody and radiolabelled antibody binding protein (e.g., protein A labeled with $I^{125}$) immobilized on a precipitable carrier such as agarose beads. The number of counts in the precipitated pellet is proportional to the amount of substrate.

In an alternate version of the RIA, a labeled substrate and an unlabelled antibody binding protein are employed. A sample containing an unknown amount of substrate is added in varying amounts. The decrease in precipitated counts from the labeled substrate is proportional to the amount of substrate in the added sample.

Enzyme linked immunosorbent assay (ELISA): This method involves fixation of a sample (e.g., fixed cells or a proteinaceous solution) containing a protein substrate to a surface such as a well of a microtiter plate. A substrate specific antibody coupled to an enzyme is applied and allowed to bind to the substrate. Presence of the antibody is then detected and quantitated by a colorimetric reaction employing the enzyme coupled to the antibody. Enzymes commonly employed in this method include horseradish peroxidase and alkaline phosphatase. If well calibrated and within the linear range of response, the amount of substrate present in the sample is proportional to the amount of color produced. A substrate standard is generally employed to improve quantitative accuracy.

Western blot: This method involves separation of a substrate from other protein by means of an acrylamide gel followed by transfer of the substrate to a membrane (e.g., nylon or PVDF). Presence of the substrate is then detected by antibodies specific to the substrate, which are in turn detected by antibody binding reagents. Antibody binding reagents may be, for example, protein A, or other antibodies. Antibody binding reagents may be radiolabelled or enzyme linked as described hereinabove. Detection may be by autoradiography, colorimetric reaction or chemiluminescence. This method allows both quantitation of an amount of substrate and determination of its identity by a relative position on the membrane which is indicative of a migration distance in the acrylamide gel during electrophoresis.

Immunohistochemical analysis: This method involves detection of a substrate in situ in fixed cells by substrate specific antibodies. The substrate specific antibodies may be enzyme linked or linked to fluorophores. Detection is by microscopy and subjective evaluation. If enzyme linked antibodies are employed, a colorimetric reaction may be required.

Fluorescence activated cell sorting (FACS): This method involves detection of a substrate in situ in cells by substrate specific antibodies. The substrate specific antibodies are linked to fluorophores. Detection is by means of a cell sorting machine which reads the wavelength of light emitted from each cell as it passes through a light beam. This method may employ two or more antibodies simultaneously.

The antibody used in the method of the present invention is selected differentially interactable with at least one form of a APOL1 protein encoded by an APOL1 allele having an SNP rs73885319 (S342G, i.e., the S342 polymorph or the G342 polymorph) and SNP rs60910145 (I384M, i.e., the I384 polymorph or the M384 polymorph) and can differentiate between polymorphs of the APOL1 protein via differential antibody interaction. Antibodies useful in context of this embodiment of the invention can be prepared using methods of antibody preparation well known to one of ordinary skills in the art, using, for example, synthetic peptides derived from the two different forms of the APOL1 protein for vaccination of antibody producing animals and subsequent isolation of antibodies therefrom. Monoclonal antibodies specific to each of the APOL1 variants can also be prepared as is described, for example, in "Current Protocols in Immunology" Volumes I-III Coligan J. E., Ed. (1994); Stites et al. (Eds), "Basic and Clinical Immunology" (8th Edition), Appleton & Lange, Norwalk, Conn. (1994); Mishell and Shiigi (Eds), "Selected Methods in Cellular Immunology", W. H. Freeman and Co., New York (1980).

The term "antibody" as used in the present invention includes intact molecules as well as functional fragments thereof, such as Fab, F(ab')2, and Fv that are capable of binding to macrophages. These functional antibody fragments are defined as follows: Fab, the fragment which contains a monovalent antigen-binding fragment of an antibody molecule, can be produced by digestion of whole antibody with the enzyme papain to yield an intact light chain and a portion of one heavy chain; Fab', the fragment of an antibody molecule that can be obtained by treating whole antibody with pepsin, followed by reduction, to yield an intact light chain and a portion of the heavy chain; two Fab' fragments are obtained per antibody molecule; (Fab')2, the fragment of the antibody that can be obtained by treating whole antibody with the enzyme pepsin without subsequent reduction; F(ab')2 is a dimer of two Fab' fragments held together by two disulfide bonds; Fv, defined as a genetically engineered fragment containing the variable region of the light chain and the variable region of the heavy chain expressed as two chains; and single chain antibody ("SCA"), a genetically engineered molecule containing the variable region of the light chain and the variable region of the heavy chain, linked by a suitable polypeptide linker as a genetically fused single chain molecule.

Methods of making these fragments are known in the art. See for example, Harlow and Lane, Antibodies: A Laboratory Manual, Cold Spring Harbor Laboratory, New York, 1988, incorporated herein by reference.

Antibody fragments according to the present invention can be prepared by proteolytic hydrolysis of the antibody or by expression in *E. coli* or mammalian cells (e.g. Chinese hamster ovary cell culture or other protein expression systems) of DNA encoding the fragment.

Antibody fragments can be obtained by pepsin or papain digestion of whole antibodies by conventional methods. For example, antibody fragments can be produced by enzymatic cleavage of antibodies with pepsin to provide a 5S fragment denoted F(ab')2. This fragment can be further cleaved using a thiol reducing agent, and optionally a blocking group for the sulfhydryl groups resulting from cleavage of disulfide linkages, to produce 3.5S Fab' monovalent fragments. Alternatively, an enzymatic cleavage using pepsin produces two monovalent Fab' fragments and an Fc fragment directly. These methods are described, for example, by Goldenberg, U.S. Pat. Nos. 4,036,945 and 4,331,647, and references contained therein, which patents are hereby incorporated by reference in their entirety. See also Porter, R. R., Biochem. J., 73: 119-126, 1959. Other methods of cleaving antibodies, such as separation of heavy chains to form monovalent light-heavy chain fragments, further cleavage of fragments, or other enzymatic, chemical, or genetic techniques may also be used, so long as the fragments bind to the antigen that is recognized by the intact antibody.

Fv fragments comprise an association of $V_H$ and $V_L$ chains. This association may be noncovalent, as described in Inbar et al., Proc. Nat'l Acad. Sci. USA 69:2659-62, 1972. Alternatively, the variable chains can be linked by an intermolecular disulfide bond or cross-linked by chemicals such as gluteraldehyde. Preferably, the Fv fragments comprise $V_H$ and $V_L$ chains connected by a peptide linker. These single-chain antigen binding proteins (sFv) are prepared by constructing a structural gene comprising DNA sequences encoding the $V_H$ and $V_L$ domains connected by an oligonucleotide. The structural gene is inserted into an expression vector, which is subsequently introduced into a host cell such as *E. coli*. The recombinant host cells synthesize a single polypeptide chain with a linker peptide bridging the two V domains. Methods for producing sFvs are described, for example, by Whitlow and Filpula, Methods, 2: 97-105, 1991; Bird et al., Science 242:423-426, 1988; Pack et al., Bio/Technology 11:1271-77, 1993; and Ladner et al., U.S. Pat. No. 4,946,778, which is hereby incorporated by reference in its entirety.

Another form of an antibody fragment is a peptide coding for a single complementarity-determining region (CDR). CDR peptides ("minimal recognition units") can be obtained by constructing genes encoding the CDR of an antibody of interest. Such genes are prepared, for example, by using the polymerase chain reaction to synthesize the variable region from RNA of antibody-producing cells. See, for example, Larrick and Fry, Methods, 2: 106-10, 1991.

Once the predisposition to develop the kidney disease has been determined, the information regarding predisposition can be presented to the individual and/or to the treating physician. This is particularly important in case of a positive prediction of kidney disease in a subject (i.e., when there is predisposition to develop kidney disease according to the methods described hereinabove), in order to take actions, which might prevent or delay the development of the kidney disease before its onset.

It should be noted that upon the onset (or occurrence) of the kidney disease, the subject's general health can deteriorate, and the subject can become severely ill, without cure, leading to death.

On the other hand, absence of predisposition to develop a kidney disease may be of a great relief to a subject being at risk thereof based on family history and/or presence of other disease(s).

Thus, according to some embodiments of the invention, the method further comprising informing the subject on the state of the predisposition to develop the kidney disease.

As used herein, the term "subject" includes mammals, preferably human beings at any age which suffer from a pathology (kidney disease) or is at risk of developing a pathology (kidney disease).

According to some embodiments of the invention, the kidney disease comprises an end stage kidney disease.

According to some embodiments of the invention, the kidney disease is not a diabetic-associated or diabetic-related kidney disease.

It should be noted that determination of the predisposition of the subject to develop a kidney disease can affect the subject's life style, such that the subject is aware of the risk to develop the disease and takes action(s) in order to prevent the kidney disease, which actions were otherwise not been taken.

For example, a subject who is predisposed to develop a kidney disease may be put on a restrictive diet for preventing overload of protein or salt on the kidney, and/or be treated with suitable medications which prevent or delay onset of the kidney disease.

According to an aspect of some embodiments of the invention there is provided a method of designing a life style change to a subject with the risk of kidney disease, comprising:

(a) identifying in a sample of the subject at least one APOL1 polypeptide variant or at least one APOL1 nucleotide mutation, (i) wherein the variant is characterized by a higher trypanolytic activity on *Trypanosoma brucei rhodesiense* as compared to the trypanolytic activity of wild type APOL1 polypeptide as set forth in SEQ ID NO:1 on the *Trypanosoma brucei rhodesiense* under identical assay conditions;

(ii) wherein the APOL1 nucleotide mutation is included in the APLO1 genomic sequence set forth in SEQ ID NO:3, and wherein the at least one nucleotide mutation being in linkage disequlibrium (LD) with the S342G mutation in the APOL1 polypeptide set forth in SEQ ID NO:1, wherein presence of the APOL1 polypeptide variant or the APOL1 nucleotide mutation indicates increased predisposition of the subject to develop the kidney disease, and;

(b) designing the life style change based on presence or absence of the APOL1 polypeptide variant or the APOL1 nucleotide mutation, thereby designing life style change to a subject with the risk of kidney disease.

As mentioned, the knowledge of presence or absence or the predisposition to develop the kidney disease can be used to design a suitable treatment regimen to a subject having a certain disease and being at risk of developing also a kidney disease. Non-limiting examples of such subjects include those infected with HIV which causes AIDS, patients who have a single kidney, a past episode of acute kidney injury, have donated a kidney or otherwise lost a kidney, recurrent urinary infections, childhood reflux disease, exposure of kidney toxic medications, patients with hypertensive nephrosclerosis, non-monogenic focalsegmental glomerulosclerosis, a patient with sickle-cell kidney disease and the like.

It should be noted that HIV-infected subjects are at risk to develop HIV-associate nephropathy (HIVAN). However, the threshold for introducing an antiretroviral therapy in patients with HIV does not currently take into account the patient's risk of HIV-related kidney disease. Such risk could potentially be accounted for by a management algorithm that includes the effects of APOL1 genotype. Thus, determining the etiology of kidney dysfunction in a patient with AIDS who is receiving potentially nephrotoxic antiretroviral therapy may be assisted by APOL1 genotyping.

According to some embodiments of the invention, the subject is infected with HIV.

According to some embodiments of the invention, the kidney disease comprises HIV-associated nephropathy (HIVAN).

Thus, according to an aspect of some embodiments of the invention there is provided a method of designing a nephrotoxic anti-retroviral treatment regimen to a subject infected with HIV, comprising:

(a) identifying in a sample of the subject at least one APOL1 polypeptide variant or at least one APOL1 nucleotide mutation, (i) wherein the variant is characterized by a higher trypanolytic activity on *Trypanosoma brucei rhodesiense* as compared to the trypanolytic activity of wild type APOL1 polypeptide as set forth in SEQ ID NO:1 on the *Trypanosoma brucei rhodesiense* under identical assay conditions;

(ii) wherein the APOL1 nucleotide mutation is included in the APLO1 genomic sequence set forth in SEQ ID NO:3, and wherein the at least one nucleotide mutation being in linkage disequlibrium (LD) with the S342G mutation in the APOL1 polypeptide set forth in SEQ ID NO:1, wherein presence of the APOL1 polypeptide variant or the APOL1 nucleotide mutation indicates increased predisposition of the subject to develop the kidney disease, and;

(b) designing the nephrotoxic anti-retroviral treatment regimen based on presence or absence of the APOL1 polypeptide variant or the APOL1 nucleotide mutation, thereby designing a nephrotoxic anti-retroviral treatment regimen to the subject infected with HIV.

For example, the clinician might decide to press on with therapy to alleviate the kidney injury in an HIV-infected patient carrying APOL1 risk alleles, or might choose not to implement such therapy in an HIV-infected patient who does not carry APOL1 risk alleles.

Similarly, determination of the predisposition to develop a kidney disease may have important considerations for both living kidney donors and recipients. For example, subjects having increased predisposition to develop a kidney disease may not be eligible to donate a kidney. Similarly, a subject having an increased predisposition to develop a kidney disease may not benefit from a kidney transplantation. Thus, the APOL1 genotyping may well be added to the battery of tests undertaken prior to living kidney donation, for the benefit of both donor and recipient.

Thus, according to an aspect of some embodiments of the invention, there is provided a method of determining if a subject is suitable for donating a kidney for transplantation, comprising:

(a) identifying in a sample of the subject at least one APOL1 polypeptide variant or at least one APOL1 nucleotide mutation, (i) wherein the variant is characterized by a higher trypanolytic activity on *Trypanosoma brucei rhodesiense* as compared to the trypanolytic activity of wild type APOL1 polypeptide as set forth in SEQ ID NO:1 on the *Trypanosoma brucei rhodesiense* under identical assay conditions;

(ii) wherein the APOL1 nucleotide mutation is included in the APLO1 genomic sequence set forth in SEQ ID NO:3, and wherein the at least one nucleotide mutation being in linkage disequlibrium (LD) with the S342G mutation in the APOL1 polypeptide set forth in SEQ ID NO:1, wherein presence of the APOL1 polypeptide variant or the APOL1 nucleotide mutation indicates increased predisposition of the subject to develop a kidney disease, and;

wherein increased predisposition of the subject to develop the kidney disease indicates that the subject is not suitable for donating the kidney for transplantation, thereby determining if the subject is suitable for donating a kidney for transplantation.

Current guidelines for the management of hypertension suggest that African Americans as a group do not enjoy renal benefit from antihypertensive therapy, and moreover the recommendations for use of specific antihypertensive drug categories in African American patients are influenced by which African subpopulation they belong to. The presence or absence of the APOL1 risk alleles for predisposition to a kidney disease may be also used to improve the individualization of therapy in the African American group of patients, such that those without APOL1 risk alleles might be expected to enjoy a substantial renal benefit from antihypertensive regimens, similar to those that have proven effective in patients of European ancestry.

It will be appreciated that the reagents utilized by the methods for determining predisposition to develop kidney disease according to some embodiments of the invention and which are described hereinabove can form a part of a kit.

Such a kit includes at least one reagent for determining a presence or absence in a homozygous or heterozygous form, of at least one APOL1 nucleotide mutation or APOL1 protein variant.

According to an aspect of some embodiments of the invention there is provided a kit for determining predisposition to a kidney disease, comprising a reagent capable of specifically detecting at least one APOL1 nucleotide mutation in the APLO1 genomic sequence set forth in SEQ ID NO:3, and/or a reagent capable of specifically detecting at least one APOL1 nucleotide mutation in the APLO1 coding sequence set forth in SEQ ID NO:2, wherein the at least one nucleotide mutation being in linkage disequilibrium (LD) with the S342G mutation in the APOL1 polypeptide set forth in SEQ ID NO:1, and/or a reagent capable of specifically detecting at least one APOL1 polypeptide variant, wherein said APOL1 polypeptide variant is characterized by a higher trypanolytic activity on *Trypanosoma brucei rhodesiense* as compared to the trypanolytic activity of wild type APOL1 polypeptide as set forth in SEQ ID NO:1 on said *Trypanosoma brucei rhodesiense* under identical assay conditions.

According to some embodiments of the invention, the APOL1 nucleotide mutation is selected from the group consisting of the guanine-containing allele of single nucleotide polymorphism (SNP) rs73885319 (SEQ ID NO:6), the guanine-containing allele of SNP rs60910145 (SEQ ID NO:7), the guanine-containing allele of SNP rs9622363 (SEQ ID NO:8), the adenine—containing allele of SNP rs60295735 (SEQ ID NO:9) and the cytosine-containing allele of SNP rs58384577 (SEQ ID NO:10).

According to some embodiments of the invention, the reagent comprises a polynucleotide capable of specifically detecting the APOL1 nucleotide mutation by any of the mutation and/or SNP detection methods described hereinabove.

According to some embodiments of the invention, the reagent comprises an antibody capable of specifically binding an APOL1 variant comprises the nucleotide mutation and not to the APLO1 wild type polypeptide.

According to preferred embodiments the APOL1 polypeptide variant which is detected by the reagent comprised in the kit has a mutation selected from the group consisting of G342, M384, N388-del and Y389-del with respect to the wild type amino acid sequence set forth in SEQ ID NO:1.

According to preferred embodiments the kit further comprising packaging material packaging at least one reagent and a notification in or on the packaging material. Such a notification identifies the kit for use in determining if an individual is predisposed to develop a kidney disease, and/or suitable to donate a kidney for transplantation, and/or suitable for receiving kidney transplantation, and/or for designing a life style change and/or for designing a treatment regimen for a subject.

The kit also includes the appropriate instructions for use and labels indicating FDA approval for use in vitro.

As used herein the term "about" refers to ±10%.

The terms "comprises", "comprising", "includes", "including", "having" and their conjugates mean "including but not limited to".

The term "consisting of" means "including and limited to".

The term "consisting essentially of" means that the composition, method or structure may include additional ingredients, steps and/or parts, but only if the additional ingredients, steps and/or parts do not materially alter the basic and novel characteristics of the claimed composition, method or structure.

As used herein, the singular form "a", "an" and "the" include plural references unless the context clearly dictates otherwise. For example, the term "a compound" or "at least one compound" may include a plurality of compounds, including mixtures thereof. Throughout this application, various embodiments of this invention may be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Whenever a numerical range is indicated herein, it is meant to include any cited numeral (fractional or integral) within the indicated range. The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals therebetween.

As used herein the term "method" refers to manners, means, techniques and procedures for accomplishing a given task including, but not limited to, those manners, means, techniques and procedures either known to, or readily developed from known manners, means, techniques and procedures by practitioners of the chemical, pharmacological, biological, biochemical and medical arts.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

Various embodiments and aspects of the present invention as delineated hereinabove and as claimed in the claims section below find experimental support in the following examples.

EXAMPLES

Reference is now made to the following examples, which together with the above descriptions illustrate some embodiments of the invention in a non limiting fashion.

Generally, the nomenclature used herein and the laboratory procedures utilized in the present invention include molecular, biochemical, microbiological and recombinant DNA techniques. Such techniques are thoroughly explained in the literature. See, for example, "Molecular Cloning: A laboratory Manual" Sambrook et al., (1989); "Current Protocols in Molecular Biology" Volumes I-III Ausubel, R. M., ed. (1994); Ausubel et al., "Current Protocols in Molecular Biology", John Wiley and Sons, Baltimore, Md. (1989); Perbal, "A Practical Guide to Molecular Cloning", John Wiley & Sons, New York (1988); Watson et al., "Recombinant DNA", Scientific American Books, New York; Birren et al. (eds) "Genome Analysis: A Laboratory Manual Series", Vols. 1-4, Cold Spring Harbor Laboratory Press, New York (1998); methodologies as set forth in U.S. Pat. Nos. 4,666,828; 4,683,202; 4,801,531; 5,192,659 and 5,272,057; "Cell Biology: A Laboratory Handbook", Volumes I-III Cellis, J. E., ed. (1994); "Current Protocols in Immunology" Volumes I-III Coligan J. E., ed. (1994); Stites et al. (eds), "Basic and Clinical Immunology" (8th Edition), Appleton & Lange, Norwalk, Conn. (1994); Mishell and Shiigi (eds), "Selected Methods in Cellular Immunology", W. H. Freeman and Co., New York (1980); available immunoassays are extensively described in the patent and scientific literature, see, for example, U.S. Pat. Nos. 3,791,932; 3,839,153; 3,850,752; 3,850,578; 3,853,987; 3,867,517; 3,879,262; 3,901,654; 3,935,074; 3,984,533; 3,996,345; 4,034,074; 4,098,876; 4,879,219; 5,011,771 and 5,281,521; "Oligonucleotide Synthesis" Gait, M. J., ed. (1984); "Nucleic Acid Hybridization" Hames, B. D., and Higgins S. J., eds. (1985); "Transcription and Translation" Hames, B. D., and Higgins S. J., Eds. (1984); "Animal Cell Culture" Freshney, R. I., ed. (1986); "Immobilized Cells and Enzymes" IRL Press, (1986); "A Practical Guide to Molecular Cloning" Perbal, B., (1984) and "Methods in Enzymology" Vol. 1-317, Academic Press; "PCR Protocols: A Guide To Methods And Applications", Academic Press, San Diego, Calif. (1990); Marshak et al., "Strategies for Protein Purification and Characterization—A Laboratory Course Manual" CSHL Press (1996); all of which are incorporated by reference as if fully set forth herein. Other general references are provided throughout this document. The procedures therein are believed to be well known in the art and are provided for the convenience of the reader. All the information contained therein is incorporated herein by reference.

General Materials and Experimental Methods

Sample Sets—

The non-diabetic ESKD sample set is a sub-set of a larger ESKD cohort previously reported (Behar et al. 2010). The designation of MYH9 associated nephropathies included hypertension affiliated chronic kidney disease, HIV-associated nephropathy (HIVAN), and non-monogenic forms of focal segmental glomerulosclerosis (Bostrom and Freedman 2010). The sample includes 430 non-diabetic ESKD cases and 525 controls, all of whom are self-identified as either African American or Hispanic American. The present inventors have already reported the African, European and Native American ancestry admixture proportions for these samples, based on a set of 40 genome wide Ancestry Informative Markers, and also the association and risk parameters for a set of 42 SNP polymorphic markers in the MYH9 genetic locus in the entire sample set (Behar et al. 2010).

The African populations sample set consists of 676 samples from 12 African populations, including Cameroon (2 ethnic groups), Congo, Ethiopia (4 ethnic groups), Ghana (2 groups), Malawi, Mozambique, Sudan with details provided in Table 2 hereinbelow. Whole Genome Amplification of extracted DNA was carried out as previously reported (van Eijk et al. 2010).

All sampling and testing was conducted with institutional review board approval for human genetic studies on anonymized samples, with informed consent.

SNP Genotyping—

Genotyping of the novel six SNPs reported herein and in Tzur et al. 2010, i.e., SNPs rs73885319, rs60910145, rs9622363 [APOL1], rs60295735 [near APOL1], rs56767103 [FOXRED2], rs11089781 [APOL3], was performed with the KasPar methodology (Petkov et al. 2004). In addition PCR and RFLP reactions were designed for the APOL1 SNPs as follows. DNA fragments containing the both APOL1 SNPs [SNP rs73885319 (S342G) and SNP rs60910145 (I384M)] were generated by PCR amplification of genomic DNA using the following primers: forward primer: 5'-ACA AGC CCA AGC CCA CGA CC-3' (SEQ ID NO:4) and the reverse primer: 5'-CCT GGC CCC TGC CAG GCA TA-3' (SEQ ID NO:5). PCR reaction mix included 30 ng template DNA with 7.5 pmol of each primer and the Red Load Taq Master (Larova). PCR conditions were 95° C. for 3 minutes followed by 40 cycles of denaturation at 95° C. for 30 seconds, annealing 65° C. for 20 seconds, and elongation 72° C. for 1 minute. The resulting amplicon was digested with both endonucleases HindIII and NspI and was run on a 2% agarose gel. SNP APOL1 rs73885319 A/G: The allele containing G eliminates a recognition site of endonuclease HindIII. APOL1 SNP rs60910145 T/G: The allele containing T generates a new recognition site of endonuclease NspI. An example for RFLP genotyping of APOL1 rs73885319 A/G and APOL1 SNP rs60910145 T/G is shown in FIG. 6. SNP validation was performed by Sanger sequencing.

Example 1

Search for Sequence Variants Associated with ESKD

In order to detect functional mutations which are significantly more associated with ESKD than all previously reported SNPs in MYH9, the present inventors have re-examined the MALD interval surrounding MYH9, and detected novel missense mutations with predicted functional effects in the neighboring loci such as the APOL1 gene.

Identification of Candidate Non-Synonymous SNPs Related to ESKD—

To search for variants possibly associated with ESKD, the present inventors analyzed 119 whole genome sequences recently released by the 1000 Genomes Project [world wide web (dot) 1000genomes (dot) org] and examined in these genomes a 1.55 Mbp interval surrounding MYH9, spanning nucleotide positions 34,000,000 to 35,550,000 (NCBI36 assembly). Of the 119 whole genome sequences, 60 are of European origin (HapMap CEU cohort), and 59 are of West-African origin (HapMap YRI cohort) yielding a total of 7,479 SNPs in the 1.55 Mbp chromosome 22 interval. Filtering criteria were applied to identify candidates for further consideration and analysis, based on: (1) low allele frequency in CEU but not in YRI, and (2) LD patterns with the previously identified leading MYH9 risk variants. From the 7,479 SNPs, the present inventors have selected for further examination all SNPs which complied with the following conditions:

(1) Minor allele frequency in the CEU cohort not exceeding 7.5% (9/120 chromosomes). This minor allele was designated as a putative "risk state" for this SNP.

(2) Risk state in the YRI cohort at allele frequency exceeding 17.5% (21/118 chromosomes).

(3) A minimal level of LD with the MYH9 S-1 SNP rs5750250 (FIG. 2). The criterion used was a chi-square test p-value not exceeding 0.15 for the 3*3 genotype table comparing each candidate SNP to the S-1 SNP in the YRI cohort.

Figure 1:
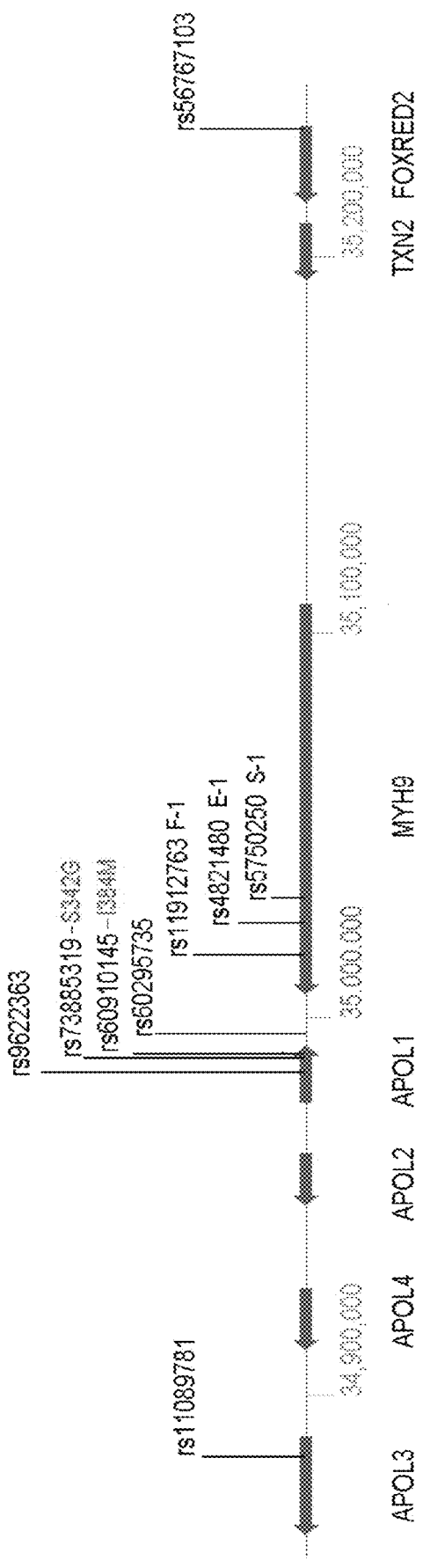

All candidate SNPs which passed these requirements (total 250) were inspected in order to identify non-synonymous exonic SNPs, indicating a possible functional role. These were again examined for consistency with association patterns in the leading MYH9 risk variants S-1 (rs5750250) and F-1 (rs11912763) (Nelson et al. 2010) to confirm higher prevalence of the African "risk" state in the YRI cohort, and rarity of the risk state in the S-1 protective state (G:G), given the high attributable risk of S-1, especially for HIVAN (Winkler et al. 2010), indicating that the causative variant should be extremely rare in the presence of the S-1 protective state. This yielded four candidate non-synonymous exonic SNPs for genotyping: The first two (rs73885319 and rs60910145) are missense mutations in the last exon of the APOL1 gene (S342G and I384M) which is the neighboring gene, located 14 kbp 3' downstream from MYH9. A third SNP (rs11089781) is a nonsense mutation (Q58X) in the APOL3 gene located 110 kbp further 3' downstream. The fourth SNP (rs56767103) is a missense mutation (R71C) in the gene FOXRED2 located 100 kbp upstream to the 5' side of MYH9 (FIG. 1). Of note the two variants located 128 bp apart in APOL1 are in almost perfect LD (237 out of 238 chromosomes from the 1000 Genomes Project).

These four variants were genotyped in a previously reported sample set of African American and Hispanic American cases and controls (n=955) (Behar et al. 2010). Associations of these candidates with ESKD phenotypes previously attributed to MYH9, were determined using logistic regression, with correction for global and local ancestry, and considering three major modes of inheritance as previously reported (Behar et al. 2010).

Association Analysis—

For determining the association of each SNP with ESKD in the dataset, the present inventors performed logistic regression with ESKD status (Cases/Control) as the response, and included covariates for local and global ancestry as well as for cohort (African American/Hispanic American). Ancestry estimates were calculated as previously described (Behar et al. 2010). In addition to the four exonic SNPs described above, two additional SNPs in the APOL1 region were chosen for genotyping, including SNP rs9622363 located in intron 3, and SNP rs60295735 located in the inter-genic region between the genes APOL1 and MYH9. These SNPs were chosen using the same criteria as those applied to the exonic SNPs, as described above.

TABLE 1

Association with non-diabetic ESKD of non-synonymous SNPs in APOL1, APOL3 and FOXRED2 in the MALD peak and comparison with leading MYH9 SNPs

| rs number | Gene | Type | Chr22 Location[a] | Alleles[b] | YRI risk frequency[c] | CEU risk frequency | Mode[d] | OR | P value |
|---|---|---|---|---|---|---|---|---|---|
| rs73885319[e] | APOL1 | exon 5 | 36661906 | A/G | 46% | 0% | Recessive | 6.7 | 2.71E−06 |
| | | S342G missense | | | | | Additive | 2.22 | 2.38E−08 |
| | | | | | | | Dominant | 2.23 | 8.11E−06 |
| rs60910145 | APOL1 | exon 5 | 36662034 | T/G | 45% | 0% | Recessive | 6.74 | 9.89E−06 |
| | | I384M missense | | | | | Additive | 2.28 | 3.00E−08 |
| | | | | | | | Dominant | 2.32 | 4.75E−06 |
| rs11089781 | APOL3 | exon 1 | 36556768 | G/A | 31% | 0% | Recessive | 6.62 | 2.82E−03 |
| | | Q58X nonsense | | | | | Additive | 2.18 | 3.79E−06 |
| | | | | | | | Dominant | 2.22 | 3.23E−05 |

TABLE 1-continued

Association with non-diabetic ESKD of non-synonymous SNPs in APOL1, APOL3 and FOXRED2 in the MALD peak and comparison with leading MYH9 SNPs

| rs number | Gene | Type | Chr22 Location[a] | Alleles[b] | YRI risk frequency[c] | CEU risk frequency | Mode[d] | OR | P value |
|---|---|---|---|---|---|---|---|---|---|
| rs56767103 | FOXRED2 | exon 1 R71C missense | 36902259 | G/A | 18% | 0% | Recessive | 1.33 | 6.83E−01 |
| | | | | | | | Additive | 1.52 | 5.19E−02 |
| | | | | | | | Dominant | 1.66 | 3.64E−02 |
| rs11912763 | MYH9 | intron 33 F-1 designation | 36684722 | G/A | 48% | 0% | Recessive | 2.38 | 2.86E−02 |
| | | | | | | | Additive | 1.96 | 4.05E−05 |
| | | | | | | | Dominant | 2.28 | 4.20E−05 |
| rs5750250 | MYH9 | intron13 S-1 designation | 36708483 | A/G | 66% | 6% | Recessive | 2.48 | 4.29E−05 |
| | | | | | | | Additive | 1.78 | 6.68E−05 |
| | | | | | | | Dominant | 1.55 | 4.97E−02 |

Table 1.
[a]Location on Chromosome 22 in NCBI37.1/hg19 assembly.
[b]African ESKD "risk" state in bold.
[c]Frequencies according to available 1000genome data.
[d]Association results were derived using logistic regression, correcting for global and local African ancestry, and combining the Hispanic and African American cohorts.
[e]See FIGS. 5A-D for allele frequency pie-charts in cases versus controls.

The APOL1 Missense Variants (Rs73885319 and Rs60910145) are More Strongly Associated with ESKD Risk than the Leading MYH9 Risk Variants—

Table 1 hereinabove shows the association results for the combined dataset of the African American and Hispanic American cohorts. For comparison, the present inventors include the results from the two previously reported leading MYH9 risk variants (S-1 rs5750250, F-1 rs11912763) (Nelson et al. 2010). The APOL1 missense variants (rs73885319 and rs60910145) are more strongly associated with ESKD risk than the leading MYH9 risk variants, both in terms of OR and p values (Table 1 above). The lower allele frequency and OR, with a higher p value for the APOL3 nonsense variant, and the weak association for the FOXRED2 missense mutation, render these variants unlikely candidates to explain the risk attributed to this genomic region. The results for combined and meta-analysis of the two separate cohort-based results are congruent (Table 2, below).

For determining whether the APOL1 SNP rs73885319 explains the association of ESKD with MYH9 SNPs, the present inventors performed a logistic regression with the same covariates, but included both the APOL1 SNP and an MYH9 SNP in the analysis. To avoid committing to a specific mode of inheritance, the present inventors included the SNPs as categorical variables with three values (three possible genotypes), and then performed an analysis of deviance on the results (Hastie and Pregibon 1992), first adding the APOL1 SNP, and then the MYH9 SNP, and performing a chi-square test for the null hypothesis that the MYH9 SNP does not add to the ability to explain ESKD status.

Analysis of deviance of the combined logistic regression indicates that LD with APOL1 SNP rs73885319 accounted for much or all the statistical association previously attributed to the leading MYH9 variants with ESKD. In this regard, the present inventors also examined two non-coding variants in the APOL1 region which are in high LD with the APOL1 missense mutations, and as expected, both showed significant disease risk association (FIG. 2 and Table 2, below).

Three major modes of association (recessive, additive, dominant) were tested through definition of appropriate dummy variables in the regression. In addition to this combined analysis, the regression analysis was performed in each cohort separately, and the resulting p-values were combined using Fisher's meta-analysis. Results are shown in Table 2 below.

TABLE 2

Association of the examined SNPs in the MALD peak with non-diabetic ESKD in African and Hispanic Americans

| rs number | Chr22 Location | Gene | Type | Alleles | YRI risk freq. | CEU risk freq. | Mode | Hispanic American OR | lower | upper | p-value | African American OR | lower | upper | p-value | Meta-analysis p-value | Combined analysis OR | p-value |
|---|---|---|---|---|---|---|---|---|---|---|---|---|---|---|---|---|---|---|
| rs7388519 | 36661906 | APOL1 | exon 5 S342G missense | A/G | 0.457 | 0 | Recessive | 15.48 | 3.99 | 60.00 | 8.8E-04 | 4.86 | 2.35 | 10.06 | 3.5E-04 | 4.9E-06 | 6.70 | 2.7E-06 |
|  |  |  |  |  |  |  | Additive | 3.59 | 2.21 | 5.83 | 1.5E-05 | 1.90 | 1.46 | 2.48 | 5.9E-05 | 2.0E-08 | 2.22 | 2.4E-08 |
| rs60910145 | 36662034 | APOL1 | exon 5 I384M missense | T/G | 0.449 | 0 | Dominant | 3.47 | 1.95 | 6.16 | 3.7E-04 | 1.89 | 1.34 | 2.67 | 2.2E-03 | 1.2E-05 | 2.23 | 8.1E-06 |
|  |  |  |  |  |  |  | Recessive | 12.80 | 3.28 | 49.94 | 2.1E-03 | 5.05 | 2.29 | 11.13 | 7.4E-04 | 2.2E-05 | 6.74 | 9.9E-06 |
|  |  |  |  |  |  |  | Additive | 3.54 | 2.17 | 5.78 | 2.3E-05 | 1.94 | 1.48 | 2.56 | 7.3E-05 | 3.5E-08 | 2.28 | 3.0E-08 |
| rs60295735 | 36667154 | Intergenic | Intergenic (APOL1-MYH9) | G/A | 0.432 | 0 | Dominant | 3.56 | 2.00 | 6.33 | 3.0E-04 | 1.95 | 1.37 | 2.76 | 1.8E-03 | 8.1E-06 | 2.32 | 4.8E-06 |
|  |  |  |  |  |  |  | Recessive | 12.79 | 3.28 | 49.92 | 2.1E-03 | 2.99 | 1.56 | 5.73 | 5.8E-03 | 1.5E-04 | 4.27 | 1.2E-04 |
|  |  |  |  |  |  |  | Additive | 3.43 | 2.10 | 5.60 | 3.6E-05 | 1.76 | 1.35 | 2.31 | 5.6E-04 | 3.8E-07 | 2.10 | 4.6E-07 |
| rs9622363 | 36656555 | APOL1 | intronic | A/G | 0.711 | 0 | Dominant | 3.32 | 1.87 | 5.91 | 5.9E-04 | 1.87 | 1.31 | 2.66 | 3.5E-03 | 2.9E-05 | 2.22 | 1.5E-05 |
|  |  |  |  |  |  |  | Recessive | 5.11 | 2.36 | 11.06 | 5.2E-04 | 3.68 | 2.46 | 5.52 | 1.2E-07 | 1.5E-09 | 3.92 | 6.3E-10 |
|  |  |  |  |  |  |  | Additive | 2.80 | 1.73 | 4.53 | 4.2E-04 | 2.34 | 1.79 | 3.06 | 1.8E-07 | 1.8E-09 | 2.46 | 2.6E-10 |
| rs56767103 | 36902259 | FOXRED2 | exon 1 R71C missense | G/A | 0.177 | 0 | Dominant | 2.03 | 1.15 | 3.60 | 4.1E-02 | 2.26 | 1.41 | 3.61 | 4.3E-03 | 1.7E-03 | 2.20 | 3.2E-04 |
|  |  |  |  |  |  |  | Recessive | Inf | 0.00 | Inf | 9.9E-01 | 1.02 | 0.33 | 3.17 | 9.8E-01 | 1.0E+00 | 1.33 | 6.8E-01 |
|  |  |  |  |  |  |  | Additive | 2.75 | 1.40 | 5.41 | 1.4E-02 | 1.23 | 0.84 | 1.82 | 3.7E-01 | 3.3E-02 | 1.52 | 5.2E-02 |
| rs11089781 | 36556768 | APOL3 | exon 1 Q58X nonsense | G/A | 0.305 | 0 | Dominant | 2.69 | 1.33 | 5.46 | 2.1E-02 | 1.33 | 0.85 | 2.10 | 3.0E-01 | 3.9E-02 | 1.66 | 3.6E-02 |
|  |  |  |  |  |  |  | Recessive | 2.30 | 0.42 | 12.44 | 4.2E-01 | 13.06 | 2.43 | 70.14 | 1.2E-02 | 3.1E-02 | 6.62 | 2.8E-03 |
|  |  |  |  |  |  |  | Additive | 2.57 | 1.55 | 4.24 | 2.0E-03 | 2.01 | 1.45 | 2.78 | 4.2E-04 | 1.3E-05 | 2.18 | 3.8E-06 |
| rs4821480 | 36695247 | MYH9 | intron23 E-1 designation | T/G | 0.763 | 0.058 | Dominant | 2.87 | 1.66 | 4.96 | 1.5E-03 | 1.93 | 1.32 | 2.82 | 4.3E-03 | 8.2E-05 | 2.22 | 3.2E-05 |
|  |  |  |  |  |  |  | Recessive | 3.37 | 1.56 | 7.29 | 9.6E-03 | 1.82 | 1.24 | 2.69 | 1.1E-02 | 1.1E-03 | 2.05 | 6.6E-04 |
|  |  |  |  |  |  |  | Additive | 1.67 | 1.06 | 2.63 | 6.4E-02 | 1.64 | 1.23 | 2.19 | 4.4E-03 | 2.6E-03 | 1.65 | 6.5E-04 |
| rs5750250 | 36708483 | MYH9 | intron13 S-1 designation | A/G | 0.661 | 0.058 | Dominant | 1.14 | 0.66 | 1.99 | 6.9E-01 | 1.92 | 1.10 | 3.36 | 5.6E-02 | 1.6E-01 | 1.47 | 1.0E-01 |
|  |  |  |  |  |  |  | Recessive | 3.82 | 1.67 | 8.73 | 7.5E-03 | 2.29 | 1.54 | 3.43 | 6.7E-04 | 6.7E-05 | 2.48 | 4.3E-05 |
|  |  |  |  |  |  |  | Additive | 1.50 | 0.96 | 2.34 | 1.4E-01 | 1.92 | 1.45 | 2.54 | 1.3E-04 | 2.1E-04 | 1.78 | 6.7E-05 |
| rs11912763 | 36684722 | MYH9 | intron 33 F-1 designation | G/A | 0.483 | 0 | Dominant | 1.02 | 0.60 | 1.74 | 9.5E-01 | 2.28 | 1.37 | 3.81 | 7.8E-03 | 4.4E-02 | 1.55 | 5.0E-02 |
|  |  |  |  |  |  |  | Recessive | 4.31 | 1.21 | 15.34 | 5.9E-02 | 1.95 | 0.95 | 3.99 | 1.3E-01 | 4.4E-02 | 2.38 | 2.9E-02 |
|  |  |  |  |  |  |  | Additive | 3.02 | 1.80 | 5.08 | 4.7E-04 | 1.67 | 1.23 | 2.27 | 5.8E-03 | 3.8E-05 | 1.96 | 4.1E-05 |
|  |  |  |  |  |  |  | Dominant | 3.64 | 1.97 | 6.75 | 5.7E-04 | 1.90 | 1.29 | 2.79 | 6.2E-03 | 4.8E-05 | 2.28 | 4.2E-05 |

Table 2: Location on Chromosome 22 in NCBI37.1/hg19 assembly. Provided are the results of the association studies performed on SNPs in the APOL1, MYH9, FOXRED2 and APOL3 genes. The Table also demonstrates similarity between the p values obtained from combining the p values from the separate cohort based analyses (African American, Hispanic American) in a meta analysis, and the p values obtained directly from a combined analysis of both cohorts including an indicator for cohort. This demonstrates the robustness of the statistical conclusions to variations in methodology.

Residual Associations of MYH9 SNPs Beyond LD with APOL1 Missense Mutations—

As described above, the present inventors performed analysis of deviance tests of the hypothesis that the APOL1 missense mutation rs73885319 can account for the statistical association between MYH9 SNPs and ESKD status. Analysis of deviance shows that the associations of the E-1 and F-1 haplotype SNPs are satisfactorily explained by this mutation ($p>0.5$ for F-1, $p>0.1$ for E-1). For the S-1 SNP rs5750250, the present inventors obtained a borderline p-value of 0.01, indicating the possibility that the S-1 SNP carries an association signal beyond its LD with rs73885319.

Example 2

Distribution and Frequencies of the APOL1 Risk Allele in African Populations

HIV-associated nephropathy (HIVAN) has been considered as the most prominent non-diabetic form of kidney disease within what has been termed the MYH9-associated nephropathies (Kopp et al. 2008). Behar et al. 2006, reported absence of HIVAN in HIV infected Ethiopian.

The APOL1 S342G Missense Mutation is Absent in Certain African Populations—

To test whether genomic factors are associated with the absence of HIVAN in Ethiopian population, the present inventors have examined the allele frequencies of the APOL1 missense mutations, as well as the leading MYH9 risk variants in 676 individuals from 12 African populations, including 304 Ethiopians and the results are presented in Table 3, hereinbelow.

TABLE 3

Distribution of the rs73885319 (S342G) risk allele among various African populations

| Country | Population | Sample Size | Latitude | Longitude | rs73885319 risk allele frequency |
|---|---|---|---|---|---|
| Ghana | Bulsa | 22 | 10.7 | -1.3 | 11% |
| Ghana | Asante | 35 | 5.8 | -2.8 | 41% |
| Cameroon | Somie | 65 | 6.45 | 11.45 | 16% |
| Congo | COG | 55 | -4.25 | 15.28 | 11% |
| Malawi | MWI | 50 | -13.95 | 33.7 | 12% |
| Mozambique | Sena | 51 | -17.45 | 35 | 12% |
| Sudan | Kordofan | 30 | 13.08 | 30.35 | 0% |
| Cameroon | Far-North-CMR/Chad | 64 | 12.5 | 14.5 | 1% |
| Ethiopia | Afar | 76 | 12 | 41.5 | 0% |
| Ethiopia | Amhara | 76 | 11.5 | 38.5 | 0% |
| Ethiopia | Oromo | 76 | 9 | 38.7 | 0% |
| Ethiopia | Maale | 76 | 7.6 | 37.2 | 0% |

Table 3: Frequency of the risk allele for rs73885319 (S342G) in APOL1 among the African populations sample set (total n = 676), according to the location of each population. The samples analyzed and presented in this Table form part of the collection of DNA maintained by The Centre for Genetic Anthropology at University College London. Buccal cells were collected with informed consent and institutional ethics approval from anonymous donors unrelated at the paternal grandfather level, classified by self declared ethnic identity.

A reduced frequency of the APOL1 missense mutations (Table 3), and of the MYH9 risk variants is shown in North-East Africa populations (e.g., Sudan, Chad and Ethiopia), with the complete absence of the APOL1 missense mutations (as well as the F-1 risk variant) in Ethiopia (FIGS. 3A-C).

Analysis and Discussion

The present inventors have uncovered that the two missense mutations S342G and I384M in the APOL1 protein can explain the increased risk for kidney disease in African Americans. The kidney diseases include: 1) Primary non-monogenic focal segmental glomerulosclerosis (FSGS), 2) Hypertension-attributed kidney disease (hypertensive nephrosclerosis), and 3) HIV-associated nephropathy (HIVAN).

The associations of these diseases with APOL1 mutations have an odds-ratio (OR) between 7-10, the highest OR ever reported for complex disease. These allelic variants are common in African continental heritage populations in the United States, such as the African and Hispanic-American populations, as well as West African immigrant communities in New York City. It is estimated that ~13% of the African American population have a homozygous or compound heterozygous state of the APOL1 risk alleles that dramatically increase their risk for CKD and attendant cardiovascular and cerebrovascular disease [Tzur S, et al. Hum Genet 2010 128:345-50; Rosset S, et al. Nat Rev Nephrol. 2011 May 3. [Epub ahead of print]; and Genovese G, et al., Science 2010; 329:841-5].

Functional Role of the APOL1 S342G Missense Mutation in *Trypanosoma Brucei Rhodesiense* Infection—

The APOL1 gene encodes apolipoprotein L-1, whose known activities include powerful trypanosomolysis (Lecordier et al. 2009). *Trypanosoma brucei rhodesiense* transmitted by tsetse flies prevalent in central and western Africa is a cause of human African trypanosomiasis, and shows resistance to this trypanosomolytic effect, by virtue of expressing serum resistance-associated protein (SRA), which interacts with the C-terminal domain of apolipoprotein L-1 (Lecordier et al. 2009). The S342G variant is predicted to modify the binding site of the C-terminal domain of the APOL1 gene product (FIGS. 4A-C).

With respect to kidney disease risk, APOL1 is also prominently involved in authophagic pathways (Zhaorigetu et al. 2008), and a recent study has provided compelling evidence for the role of well preserved authophagy in the integrity of renal glomerular podocytes (Hartleben et al. 2010). Moreover, apolipoproteins have also been identified as circulating inhibitors of glomerular proteinuria (Candiano et al. 2001).

Functional studies, combined with clinical and genetic evidence—point to a "gain-of-injury" model, as opposed to a "loss-of-function" model for the mechanism of APOL1 mediated risk. Moreover, preliminary results indicate that the mechanistic distinction between the risk (African risk variant states) and non-risk (non-African protective states) of the gene, relate to access to its target of injury.

The APOL1 genetic markers can be useful in the clinical setting. For example, the threshold for introducing antiretroviral therapy in patients with HIV does not currently take into account the patient's risk of HIV-related kidney disease. Such risk could potentially be accounted for by a management algorithm that includes the effects of APOL1 genotype. So too, determining the etiology of kidney dysfunction in a patient with AIDS who is receiving potentially nephrotoxic antiretroviral therapy may be assisted by APOL1 genotyping. For example, the clinician might decide to press on with therapy to alleviate the kidney injury in a patient carrying APOL1 risk alleles, or might choose not to implement such therapy in a patient who does not carry APOL1 risk alleles.

With regard to transplantation, APOL1 genotype may have important considerations for both living kidney donors and recipients. African American kidney donors have poorer long-term renal function than European American donors. If this observation turns out to be restricted to the subgroup of donors who are in the APOL1 risk category, APDL1 genotyping may well be added to the battery of tests undertaken prior to living kidney donation, for the benefit of both donor and recipient.

New insights may also be forthcoming with regard to the recurrence of focal segmental glomerulosclerosis following kidney transplantation. One these studies, implicated apolipoproteins among the circulating factors that govern recurrent proteinuria following transplantation in focal segmental glomerulosclerosis. Thus advance knowledge of genotype might guide preparatory therapy (e.g. plasmapheresis) for this possible outcome, or suggest new preventive or therapeutic approached.

Current guidelines for the management of hypertension suggest that African Americans as a group do not enjoy renal benefit from antihypertensive therapy, and moreover the recommendations for use of specific antihypertensive drug categories in African American patients are influenced by which African subpopulation they belong to. APDL1 genotyping may improve the individualization of therapy in this very large group of patients, such that those without APDL1 risk alleles might be expected to enjoy a substantial renal benefit from antihypertensive regimens, similar to those that have proven effective in patients of European ancestry.

Indeed, APDL1 seems to offer a particularly enlightening example of a gene with DNA sequence variants that are common in the population, and which confer an advantage under one set of environmental conditions (trypanosomiasis epidemics) but may have deleterious effects in the face of a different set of environmental conditions (such as HIV infection and increased life expectancy). This interplay is part of the emerging discipline of evolutionary medicine and validates in the clinical setting the maxim of the eminent geneticist Theodosius Dobzhansky, "Nothing in biology makes sense except in the light of evolution".

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention. To the extent that section headings are used, they should not be construed as necessarily limiting. In addition, any priority document(s) of this application is/are hereby incorporated herein by reference in its/their entirety.

REFERENCES

Additional References are Cited in Text

Barrett J C, Fry B, Mailer J, Daly M J (2005) Haploview: analysis and visualization of L D and haplotype maps. Bioinformatics 21: 263-5;

Behar D M, Rosset S, Tzur S, Selig S, Yudkovsky G, Bercovici S, Kopp J B, Winkler C A, Nelson G W, Wasser W G, Skorecki K (2010) African ancestry allelic variation at the MYH9 gene contributes to increased susceptibility to non-diabetic end-stage kidney disease in Hispanic Americans. Hum Mol Genet 19: 1816-27;

Behar D M, Shlush L I, Maor C, Lorber M, Skorecki K (2006) Absence of HIV-associated nephropathy in Ethiopians. Am J Kidney Dis 47: 88-94;

Billas I M, Iwema T, Gamier J M, Mitschler A, Rochel N, Moras D (2003) Structural adaptability in the ligand-binding pocket of the ecdysone hormone receptor. Nature 426: 91-6;

Bostrom M A, Freedman B I (2010) The Spectrum of MYH9-Associated Nephropathy. Clin J Am Soc Nephrol;

Candiano G, Musante L, Carraro M, Faccini L, Campanacci L, Zennaro C, Artero M, Ginevri F, Perfumo F, Gusmano R, Ghiggeri G M (2001) Apolipoproteins prevent glomerular albumin permeability induced in vitro by serum from patients with focal segmental glomerulosclerosis. J Am Soc Nephrol 12: 143-50;

Hartleben B, Godel M, Meyer-Schwesinger C, Liu S, Ulrich T, Kobler S, Wiech T, Grahammer F, Arnold S J, Lindenmeyer M T, Cohen C D, Pavenstadt H, Kerjaschki D, Mizushima N, Shaw A S, Walz G, Huber T B (2010) Autophagy influences glomerular disease susceptibility and maintains podocyte homeostasis in aging mice. J Clin Invest 120: 1084-96;

Hastie T J, Pregibon D (1992) In: Chambers J M, Hastie T J (eds) Statistical Models in S. Wadsworth & Brooks;

Kao W H, Klag M J, Meoni L A, Reich D, Berthier-Schaad Y, Li M, Coresh J, Patterson N, Tandon A, Powe N R, Fink N E, Sadler J H, Weir M R, Abboud H E, Adler S G, Divers J, Iyengar S K, Freedman B I, Kimmel P L, Knowler W C, Kohn O F, Kramp K, Leehey D J, Nicholas S B, Pahl M V, Schelling J R, Sedor J R, Thornley-Brown D, Winkler C A, Smith M W, Parekh R S (2008) MYH9 is associated with nondiabetic end-stage renal disease in African Americans. Nat Genet 40: 1185-92;

Kopp J B, Smith M W, Nelson G W, Johnson R C, Freedman B I, Bowden D W, Oleksyk T, McKenzie L M, Kajiyama H, Ahuja T S, Berns J S, Briggs W, Cho M E, Dart R A, Kimmel P L, Korbet S M, Michel D M, Mokrzycki M H, Schelling J R, Simon E, Trachtman H, Vlahov D, Winkler C A (2008) MYH9 is a major-effect risk gene for focal segmental glomerulosclerosis. Nat Genet 40: 1175-84;

Lecordier L, Vanhollebeke B, Poelvoorde P, Tebabi P, Paturiaux-Hanocq F, Andris F, Lins L, Pays E (2009)C-terminal mutants of apolipoprotein L-I efficiently kill both *Trypanosoma brucei brucei* and *Trypanosoma brucei rhodesiense*. PLoS Pathog 5: e1000685;

Nelson G W, Freedman B I, Bowden D W, Langefeld C D, An P, Hicks P J, Bostrom M A, Johnson R C, Kopp J B, Winkler C A (2010) Dense mapping of MYH9 localizes the strongest kidney disease associations to the region of introns 13 to 15. Hum Mol Genet 19: 1805-15;

Pettersen E F, Goddard T D, Huang C C, Couch G S, Greenblatt D M, Meng E C, Ferrin T E (2004) UCSF Chimera—a visualization system for exploratory research and analysis. J Comput Chem 25: 1605-12;

Petkov P M, Ding Y, Cassell M A, Zhang W, Wagner G, Sargent E E, Asquith S, Crew V, Johnson K A, Robinson P, Scott V E, Wiles M V (2004) An efficient SNP system for mouse genome scanning and elucidating strain relationships. Genome Res 14: 1806-11;

van Eijk R, van Puijenbroek M, Chhatta A R, Gupta N, Vossen R H, Lips E H, Cleton-Jansen A M, Morreau H, van Wezel T (2010) Sensitive and specific KRAS somatic mutation analysis on whole-genome amplified DNA from archival tissues. J Mol Diagn 12: 27-34;

Winkler C A, Nelson G, Oleksyk T K, Nava M B, Kopp J B (2010) Genetics of focal segmental glomerulosclerosis and human immunodeficiency virus-associated collapsing glomerulopathy: the role of MYH9 genetic variation. Semin Nephrol 30: 111-25;

Zhang Y (2008) I-TASSER server for protein 3D structure prediction. BMC Bioinformatics 9: 40;

Zhang Y (2009) I-TASSER: fully automated protein structure prediction in CASP8. Proteins 77 Suppl 9: 100-13;

Zhaorigetu S, Wan G, Kaini R, Jiang Z, Hu C A (2008) ApoL1, a BH3-only lipid-binding protein, induces autophagic cell death. Autophagy 4: 1079-82;

What is claimed is:

1. A kit for detecting a nucleotide sequence encoding an apolipoprotein L-1 (APOL1) polypeptide variant of the amino acid sequence of SEQ ID NO: 1 comprising a biological sample of a subject having kidney disease and a labeled oligonucleotide which hybridizes to the nucleotide sequence encoding an APOL1 polypeptide variant of the amino acid sequence of SEQ ID NO: 1 with at least one mutation selected from the group consisting of glycine at position 342 (G342), methionine at position 384 (M384), deletion of asparagine at position 388 (N388-del) and deletion of tyrosine at position 389 (Y389-del), wherein said labeled oligonucleotide does not hybridize to the nucleotide sequence encoding the wild type APOL1 polypeptide of the amino acid sequence of SEQ ID NO: 1, and wherein said labeled oligonucleotide is a fluorescently-labeled oligonucleotide or a radioactively-labeled oligonucleotide.

2. The kit of claim 1, wherein said biological sample is a DNA sample.

3. The kit of claim 1, wherein said labeled oligonucleotide hybridizes to at least two of the nucleotide sequences encoding said apolipoprotein L-1 (APOL1) polypeptide variants.

4. The kit of claim 1, wherein said labeled oligonucleotide hybridizes to a nucleotide sequence encoding apolipoprotein L-1 (APOL1) polypeptide variants comprising at least two of said mutations but does not hybridize to the nucleotide sequence encoding the wild type APOL1 polypeptide of the amino acid sequence of SEQ ID NO: 1.

5. The kit of claim 1, wherein said subject is an African-American.

6. The kit of claim 1, wherein said labeled oligonucleotide is radioactively-labeled.

7. The kit of claim 1, wherein said labeled oligonucleotide is fluorescently-labeled.

* * * * *

SEQUENCE LISTING

```
<160> NUMBER OF SEQ ID NOS: 10

<210> SEQ ID NO 1
<211> LENGTH: 398
<212> TYPE: PRT
<213> ORGANISM: Homo sapiens
<220> FEATURE:
<221> NAME/KEY: misc_feature
<222> LOCATION: (342)..(342)
<223> OTHER INFORMATION: Can be S or G
<220> FEATURE:
<221> NAME/KEY: misc_feature
<222> LOCATION: (384)..(384)
<223> OTHER INFORMATION: Can be I or M
<220> FEATURE:
<221> NAME/KEY: misc_feature
<222> LOCATION: (388)..(388)
<223> OTHER INFORMATION: May be missing
<220> FEATURE:
<221> NAME/KEY: misc_feature
<222> LOCATION: (389)..(389)
<223> OTHER INFORMATION: May be missing

<400> SEQUENCE: 1

Met Glu Gly Ala Ala Leu Leu Arg Val Ser Val Leu Cys Ile Trp Met
1               5                  10                  15

Ser Ala Leu Phe Leu Gly Val Gly Val Arg Ala Glu Glu Ala Gly Ala
            20                  25                  30

Arg Val Gln Gln Asn Val Pro Ser Gly Thr Asp Thr Gly Asp Pro Gln
        35                  40                  45

Ser Lys Pro Leu Gly Asp Trp Ala Ala Gly Thr Met Asp Pro Glu Ser
    50                  55                  60

Ser Ile Phe Ile Glu Asp Ala Ile Lys Tyr Phe Lys Glu Lys Val Ser
65                  70                  75                  80

Thr Gln Asn Leu Leu Leu Leu Thr Asp Asn Glu Ala Trp Asn Gly
                85                  90                  95

Phe Val Ala Ala Glu Leu Pro Arg Asn Glu Ala Asp Glu Leu Arg
                100                 105                 110

Lys Ala Leu Asp Asn Leu Ala Arg Gln Met Ile Met Lys Asp Lys Asn
            115                 120                 125

Trp His Asp Lys Gly Gln Gln Tyr Arg Asn Trp Phe Leu Lys Glu Phe
        130                 135                 140

Pro Arg Leu Lys Ser Glu Leu Glu Asp Asn Ile Arg Arg Leu Arg Ala
145                 150                 155                 160

Leu Ala Asp Gly Val Gln Lys Val His Lys Gly Thr Thr Ile Ala Asn
                165                 170                 175

Val Val Ser Gly Ser Leu Ser Ile Ser Ser Gly Ile Leu Thr Leu Val
            180                 185                 190

Gly Met Gly Leu Ala Pro Phe Thr Glu Gly Gly Ser Leu Val Leu Leu
        195                 200                 205

Glu Pro Gly Met Glu Leu Gly Ile Thr Ala Ala Leu Thr Gly Ile Thr
    210                 215                 220

Ser Ser Thr Met Asp Tyr Gly Lys Lys Trp Trp Thr Gln Ala Gln Ala
```

```
                225                 230                 235                 240
    His Asp Leu Val Ile Lys Ser Leu Asp Lys Leu Lys Glu Val Arg Glu
                    245                 250                 255

Phe Leu Gly Glu Asn Ile Ser Asn Phe Leu Ser Leu Ala Gly Asn Thr
                    260                 265                 270

Tyr Gln Leu Thr Arg Gly Ile Gly Lys Asp Ile Arg Ala Leu Arg Arg
                    275                 280                 285

Ala Arg Ala Asn Leu Gln Ser Val Pro His Ala Ser Ala Ser Arg Pro
                290                 295                 300

Arg Val Thr Glu Pro Ile Ser Ala Glu Ser Gly Glu Gln Val Glu Arg
    305                 310                 315                 320

Val Asn Glu Pro Ser Ile Leu Glu Met Ser Arg Gly Val Lys Leu Thr
                    325                 330                 335

Asp Val Ala Pro Val Xaa Phe Phe Leu Val Leu Asp Val Val Tyr Leu
                    340                 345                 350

Val Tyr Glu Ser Lys His Leu His Glu Gly Ala Lys Ser Glu Thr Ala
                    355                 360                 365

Glu Glu Leu Lys Lys Val Ala Gln Glu Leu Glu Glu Lys Leu Asn Xaa
                370                 375                 380

Leu Asn Asn Asn Tyr Lys Ile Leu Gln Ala Asp Gln Glu Leu
    385                 390                 395
```

<210> SEQ ID NO 2
<211> LENGTH: 2924
<212> TYPE: DNA
<213> ORGANISM: Homo sapiens
<220> FEATURE:
<221> NAME/KEY: misc_feature
<222> LOCATION: (1231)..(1231)
<223> OTHER INFORMATION: can be A or G
<220> FEATURE:
<221> NAME/KEY: misc_feature
<222> LOCATION: (1359)..(1359)
<223> OTHER INFORMATION: can be T or G
<220> FEATURE:
<221> NAME/KEY: misc_feature
<222> LOCATION: (1369)..(1371)
<223> OTHER INFORMATION: May be missing
<220> FEATURE:
<221> NAME/KEY: misc_feature
<222> LOCATION: (1372)..(1374)
<223> OTHER INFORMATION: May be missing
<220> FEATURE:
<221> NAME/KEY: misc_feature
<222> LOCATION: (2538)..(2538)
<223> OTHER INFORMATION: can be T or C

<400> SEQUENCE: 2

```
gactttcact ttccctttcg aattcctcgg tatatcttgg ggactggagg acctgtctgg     60
ttattataca gacgcataac tggaggtggg atccacacag ctcagaacag ctggatcttg    120
ctcagtctct gccagggaa gattccttgg aggagcacac tgtctcaacc cctcttttcc    180
tgctcaagga ggaggccctg cagcgacatg gagggagctg ctttgctgag agtctctgtc    240
ctctgcatct ggatgagtgc acttttcctt ggtgtgggag tgagggcaga ggaagctgga    300
gcgagggtgc aacaaaacgt tccaagtggg acagatactg gagatcctca aagtaagccc    360
ctcggtgact gggctgctgg caccatggac ccagagagca gtatctttat tgaggatgcc    420
attaagtatt tcaaggaaaa agtgagcaca cagaatctgc tactcctgct gactgataat    480
gaggcctgga acggattcgt ggctgctgct gaactgccca ggaatgaggc agatgagctc    540
cgtaaagctc tggacaacct tgcaagacaa atgatcatga agacaaaaaa ctggcacgat    600
```

```
aaaggccagc agtacagaaa ctggtttctg aaagagtttc ctcggttgaa aagtgagctt    660
gaggataaca taagaaggct ccgtgccctt gcagatgggg ttcagaaggt ccacaaaggc    720
accaccatcg ccaatgtggt gtctggctct ctcagcattt cctctggcat cctgaccctc    780
gtcggcatgg gtctggcacc cttcacagag ggaggcagcc ttgtactctt ggaacctggg    840
atggagttgg gaatcacagc cgctttgacc gggattacca gcagtaccat ggactacgga    900
aagaagtggt ggacacaagc ccaagcccac gacctggtca tcaaaagcct tgacaaattg    960
aaggaggtga gggagttttt gggtgagaac atatccaact ttctttcctt agctggcaat   1020
acttaccaac tcacacgagg cattgggaag gacatccgtg ccctcagacg agccagagcc   1080
aatcttcagt cagtaccgca tgcctcagcc tcacgccccc gggtcactga gccaatctca   1140
gctgaaagcg gtgaacaggt ggagagggtt aatgaaccca gcatcctgga aatgagcaga   1200
ggagtcaagc tcacggatgt ggcccctgta ngcttctttc ttgtgctgga tgtagtctac   1260
ctcgtgtacg aatcaaagca cttacatgag ggggcaaagt cagagacagc tgaggagctg   1320
aagaaggtgg ctcaggagct ggaggagaag ctaaacatnc tcaacaataa ttataagatt   1380
ctgcaggcgg accaagaact gtgaccacag ggcagggcag ccaccaggag agatatgcct   1440
ggcaggggcc aggacaaaat gcaaactttt tttttttct gagacagagt cttgctctgt    1500
cgccaagttg gagtgcaatg gtgcgatctc agctcactgc aagctctgcc tcccgtgttc   1560
aagcgattct cctgccttgg cctcccaagt agctgggact acaggcgcct accaccatgc   1620
ccagctaatt tttgtatttt taatagagat ggggtttcac catgttggcc aggatggtct   1680
cgatctcctg acctcttgat ctgcccacct tggcctccca aagtgctggg attacaggcg   1740
tgagccatcg cttttgaccc aaatgcaaac attttattag ggggataaag agggtgaggt   1800
aaagtttatg gaactgagtg ttagggactt tggcatttcc atagctgagc acagcagggg   1860
aggggttaat gcagatggca gtgcagcaag gagaaggcag gaacattgga gcctgcaata   1920
agggaaaaat gggaactgga gagtgtgggg aatgggaaga agcagtttac tttagactaa   1980
agaatatatt gggggggccgg gtgtagtggc tcatgcctgt aatcccagca ctttgggagg   2040
ccaaggcggg cggatcacga ggtcaggaga tcgagaccat cctggctaac acagtgaaac   2100
cccgtctcta ctaaaaatac aaaaaattag ccgggcatgg tggcgggcgc ctgtagttcc   2160
agctaactgg gcggctgagg caggagaatg gcgtgaacct gggaggtgga gcttgcagtg   2220
agccgagata tcgccactgc actccagcct gggtgacaga gcgagactcc atctcaaaaa   2280
aaaaaaaaaa aagaatatat tgacggaaga atagagagga ggcttgaagg aaccagcaat   2340
gagaaggcca ggaaaagaaa gagctgaaaa tggagaaagc ccaagagtta gaacagttgg   2400
atacaggaga gaaacagcg gctccactac agacccagcc ccaggttcaa tgtcctccga    2460
agaatgaagt cttccctgg tgatggtccc ctgccctgtc tttccagcat ccactctccc    2520
ttgtcctcct gggggcanat ctcagtcagg cagcggcttc ctgatgatgg tcattggggt   2580
ggttgtcatg tgatgggtcc cctccaggtt actaaagggt gcatgtcccc tgcttgaaca   2640
ctgaagggca ggtggtgggc catggccatg gtccccagct gaggagcagg tgtccctgag   2700
aacccaaact tcccagagag tatgtgagaa ccaaccaatg aaaacagtcc catcgctctt   2760
acccggtaag taaacagtca gaaaattagc atgaaagcag tttagcattg ggaggaagct   2820
cagatctcta gagctgtctt gtcgccgccc aggattgacc tgtgtgtaag tcccaataaa   2880
ctcacctact catcaagctg gaaaaaaaaa aaaaaaaaa aaaa                     2924
```

```
<210> SEQ ID NO 3
<211> LENGTH: 51060
<212> TYPE: DNA
<213> ORGANISM: Homo sapiens
<220> FEATURE:
<221> NAME/KEY: misc_feature
<222> LOCATION: (34556)..(34556)
<223> OTHER INFORMATION: can be A or G
<220> FEATURE:
<221> NAME/KEY: misc_feature
<222> LOCATION: (39907)..(39907)
<223> OTHER INFORMATION: can be A or G
<220> FEATURE:
<221> NAME/KEY: misc_feature
<222> LOCATION: (40035)..(40035)
<223> OTHER INFORMATION: can be G or T
<220> FEATURE:
<221> NAME/KEY: misc_feature
<222> LOCATION: (40045)..(40047)
<223> OTHER INFORMATION: May be missing
<220> FEATURE:
<221> NAME/KEY: misc_feature
<222> LOCATION: (40048)..(40050)
<223> OTHER INFORMATION: May be missing
<220> FEATURE:
<221> NAME/KEY: misc_feature
<222> LOCATION: (41214)..(41214)
<223> OTHER INFORMATION: can be C or T
<220> FEATURE:
<221> NAME/KEY: misc_feature
<222> LOCATION: (45155)..(45155)
<223> OTHER INFORMATION: can be A or G

<400> SEQUENCE: 3
tcctggcatc tcctttcatt tttcctttct tcccaaatta acctctttcc aacacagcac    60
ttcaagttcc cctggaactt catcggtcca tcggtgtccc ctggtctgga agagcaccga   120
ccacttgcca aggcccccac cactctgctg ccatcacaac caccatcacc accattacga   180
gaaaaacttg agactgatgg cccccaaagc ttagaaggag ctgagagacc aaagaatgac   240
tcgaacaagt ccagcttggt gagtaggtga gtttattggg acttacacac aggtcaatcc   300
tgggcagcga caggacagct ctagagatct gtgcttcctc ccaatgctaa actgctttca   360
tgctaatctt ctgactgttt acttaccggc taagagcgat gggactgttt tcattggttg   420
gttctcagat actctctggg aagtttgggt tctcagggac acctgctcct cagctgggga   480
ttgtggccat ggcctaccac ctgcctctca gggttcaagc aggggacatg caccctttag   540
taacctggag gggacccgtc acatgacaac cacccaaacc accatcatga agaagccact   600
ggctgactgt gatacacccc cagaaggaca agggagagtg gatgctggaa agacagagcg   660
agagaccatc accagggaaa gactttattc ttggaaggac atcaaacctg gggggggtc    720 ggtagtggag ctgctgtttc ttctcctgta tccaacagtt ctaactctgg ttttctccat   780
tttcagctct ttcttttcct ggccttctca ttgctggttc ctgcaagctc ccctctatt    840 cttcgcccaa tatattcttt agtccaaagt aaactacttc ttcccattcc ccacactctc   900
cagtcctctc tcctccctta ttgcaggctc cagtgttcct gccttctcct tggtgcactt   960
gccatctgca ttaacccctc ccttgctgtg ctcagctaca caaatgccaa agtcactaac  1020
actcagttcc ataagcttta ccttgccctc cttatcccc taataaaatg tctgcatttt  1080
ggccaggcgc ggtggctcac gcctgtaatc ccagcacttt gggaggccga ggtgggcaga  1140
tcacgaggtc aggagatgga gaccatcgtg ctaacacag tgaaacccg tctccagtga    1200 aaatacaaaa aaattagccg ggcgtggtgg caggtgcctg tagtcccagc tactcggag    1260 actgaggccg gagaatggtg tgaacccggg aggcggagtt tgcagtgagc cgagattgag  1320
```

```
ccactgcact ccatcctggg cgatagagcg agactccatc tcaaaaaaaa aaaaaaaaaa    1380
aaaaaaaagt ctgcattttg tcctggcctg tgcccggcat ttctgccctg gtggctgcac    1440
tgctctgggg tcattggtct tggcctggct gcagcatctc atggatcttg gtgagaaagt    1500
tgagcttccc ctccagctcc tgagcccgct tcttcagctc ctcagctgac tctgactttg    1560 cccctcaag caagtgcttt gactcatatg caaggctgac cacatccagc agaagcaaga    1620
tgcctccagt ggctgcaccc acgatcatgg ttcctctgct cattgcctgg gcggggcctt    1680
caacaaccct ctcaacctgt tcaccgcctt cagctgagat tcgcccaatg atatgcgggg    1740
gtggggcata cgctcctaac tgagggttgg ctctggctcg tctgatggca cggatgttcc    1800
tcccaatccc ttgtgtgact tggtaccaat tgtcaactaa ggtaagaaca ttgggtgtgt    1860
tcccacccac aaactccttc atcacctttg ctacattggt gccgctttgg tccaagttgc    1920
gggcttgggc tcgtgcccgc aatttgttta ctagttctac cacactgcag gtaatcccag    1980
ccacagcagc tgctgctccc agacccatgc cagtgtccaa gagcacaaaa ctgattcctt    2040
ctgtgaaggg tgccagaccc aggccgagga gggtcaggat gccagaggta gtgccaacag    2100
agttggacac cacattggca atggtggtgc ctctgtggac ctgctcaacc tcctctgcaa    2160
gggcacggag cttccttatg tgatcctcaa gctccctttt caaccgagga aactctttca    2220
aaaaccactg cctgtgctgc tggtctttat cgtggcggtt tttgtccttc atgaccatgt    2280
gacttgcaag cttgttcaga gctttacgga gctcatctgc ctcatccctg cacaaggaaa    2340
ggttaaagga ttaagaaatg cagtttccct atctgtgaaa tgagctccat gcgatctcta    2400
tcctgtgtaa attgcagagc tttcactatc aatcaaatag aaacaaattt tacaaatgga    2460
attaattatc tttcaaactc aaacacattt tgttcatcat agatattcct cagtacttat    2520
tccatatgga aataaatatc ttaaaggcac ctcagatgct ctttcatggt aggtgtttga    2580
taaagatgcc tcctcactca agggcaggtc aacaccgtga ctgccaaagt gtttggagag    2640
ggaaaactct gcagatgaac aaagagcagt gagagtgaga caaagagacc ttattaccag    2700
gatggcagga aagtgaagca tgaactttac ccaaagagag gccttccctt tgtcctcagc    2760
tcctgggaag tgatctccag gcccctggaa tgtcctgcct ggtaggaaca tctttctttg    2820
cctggtgatt tggccacggg acagtatagc gatgtgatgg atgataggt ttggggctat    2880 ttggtgtctt tcctgacttc cagaggactt ggggactaaa ggtgtgagat ctcagggaag    2940
ggctggagac tctagccatg agggcagctt gtgatccagc cccagcagat actctggaca    3000
ctaaggcatg ggttgagaaa gaaggacttt ctccttgacc aactccagct gggctcttca    3060
gagcttcttc tccactaggc gccgaccttg gccttccaca ctcacccact gctttctgga    3120
cttgcaccac cttggctcag caagaatctc cccaaatcag tttagggagg tcctccccg    3180 cttgctgtct gagcaccgtt tgttatctga tcatgctcct cacccccacc actggtggtt    3240
gagggtctga cctgcctttg gcgagaatcc tgttaggcca gtttagcagg aacccccac    3300 tctggcgtct cctgtcagtc ctgttccatc tcccgccccc accctggtgt tggctgtgac    3360 tcccctctg tctttactat atttggagct gggctcagtc tccctcccct gtaacaacaa    3420
tcctgaataa aggcttcatt tctggtttaa tgtgattcac aggaattttt ccttaactgg    3480
gtgagcttcc ctggttggca acaccgcatg tgttttgtcc cacattcaca caggagaaca    3540
cagcctcctg aggacaatga agattcacac ctgaaatcct cccagactct gcctgtgtg    3600 tctcttcctt aggctgattt taatctgtgt tctttccctg tgataaacca caatcgtgca    3660
```

```
atagcagttt tcagtgagtt acgtgagtcc ttctagtgaa ttataaaatc taaggatgat    3720
tttaggaatc cccatagatt tgcaggtggt gtcaaaggta agggtgccct cagacattgc    3780
agtctggcta tctctgagta ctttgaattc aaacaaaaac aaaacctcag aaagacagga    3840
gatcactttg cctggcatct gctcccttcc aatgcctcat gcccttttcac ctggctgaag   3900
gctactgggt gcggccactg ccccagctga ctggagtggg agatctggct attcattctg    3960
gctccacatg gacgctccag ccaccttact gcctcctgac ctaccacctg cacccccaac    4020
cttccaggtc tcactcgcag gtgtcaccag cctaactgat gccttagcag tgacagcttc    4080
acctgtgtgc acagcaaggc catgtgcaat tttatggaac cactagaaga ctcaagacac    4140
tttcagaacc atctatataa attgctaatg ctgaaaagac ctgaatttgg tcaagatggt    4200
agaggaagtg ttttcctcct cggttgggac tttgtgagtc tgctcagtac ccctgaaatt    4260
acacaaattg gcagcaactc attctacttt ggaaatggtc actaaggcat gccatggtaa    4320
ggagcttctc tgtgtagaag agaagaaggt ctgaaagggt agtccagaac tcaccagttc    4380
caaggcatgg ggtgagagac acaggctacc atgaccctgt atgcccatga gtgttgggat    4440
catccagaca gggaagaaat atccctctcc cactcacatg tcctctgcaa gttcatgacc    4500
tccttaagtt tcaagccctt ggtgcctctc tttccacacc ctagtcccag ccctggtgcc    4560
ccagccttcc tgcttgtcct accaaaccaa ggctgactct tactccatcc tgactccagg    4620
ctctgacact ggtcccggtc tctctgggcc tttgagcagg atcttagtcc ttggttcccc    4680
accttttgacc tggagttgcc tctaaggcct tcaccacact cctatgacat tgaattgcta   4740
ttcctattgg acagaagaca gttccaagtc tccatgacat aagcccagag cccaggaact    4800
aggcctctca ggatcctgga ccagcagaag ggtcctgctg tgtttgtgga attcttcaga    4860
tgagaaaaaa ggccccagcc agcatcccca ggaacacata ttgtttaggt taggattttt    4920
ctgacttttc ccaaaggaag tcctgctggg ctcccatctt caagaagaag atccttaacc    4980
ctggtctctt tccaccaagc ttgtaagatg ttaacgttaa ctgtgcacct actatgtgtc    5040
agtcattatg ctaagcactt tacatgcatg atctcatttt tctcataata aaactccatt    5100
gatgaagaaa ggctgaaagt gagaaagtaa ctggcaaagt tcccatcacc agcagatggc    5160
agaaatgacc ctgttcctgt gggcttccta tcccctcagc ctgaggctac tcactgccag    5220
cgaaggacat ggaggaaata ttcctcctgg agtgccgaga aggtcatcct caagcccagc    5280
agaggggggct gcctggagga ggtgtgcctg tcagggacaa ccagcccagg ggagatctga   5340
gtggcatcgc tggggcgccc catggagtta accccatgga gcttacctgg gcagttcagc    5400
agcagccacg aatccattcc aggcttcatc atcagtcagc agttgtagca gattctctct    5460
gctcacttgg tcctggaaat acttaaggta atcctcaata aagatactgc tctctagttg    5520
gaaagaagaa aggataaggt tggaggatag tgtaggggag cataacagcc attgcacatt    5580
aggtggttac atgttaattt ttcctggaca actgtgatgt gggacatgtt tgatggagtc    5640
atcagtgcta tagagggatt gtgtgcccccc aaaattcata tgctgaagcc ctaaactcga   5700
gtgactatat ttgaagattg ggcctttaag gaagcaatta agactgaatg agatcacaag    5760
ggtagggctc taatcctact agagggctag tgtcctattg taagaagaga aagagaaaca    5820
ataaggccag gtaagcacac agcgcaaagg cagctgccgc aagccagcaa gagagtcctc    5880
ccaaggctcc aacccttaa tttaataaac catcaaagac agaaacccca aaccccactg     5940
ggcccaactg gctcttctga gtccacctgc acttccatcc ctgagcctgt gcttctgctt    6000
tgcagctgat ttgttttttc tttgactcaa attttttctc tcagtggagt caaaaacctg    6060
```

```
gacaaggcta aggtctggtc tctcctggat tcggagaact tcctaaaccc accagcacca      6120
atgtgaccag gaattttcca aaaggtaaa tcaaaacagg cagttttgta actgcaacca      6180
atcaaataat gtccttattg cagtttcata tttactcgat aaatacttgt ctctgacact      6240
ttttcatcat aacatgaagc ctcttccagt ttggttttct caattcatga attccttctt      6300
attcaaataa atgttactgt gcctcagatt tttctttgac aaggggtatc tgagatcatg      6360
ggaatgaggc cctgcctgag gcagtcatcc ctggtcagca ggtgcttgtg atgggcagtg      6420
cagggcgggt gccctaacac agatgagggg actgggtggc ttccacctgg aatcaacagg      6480
ggatagatag aggagataga ggggatgcaa actaattctt agggaggccc tactgtgtgg      6540
caggctttgg ccaggccagg tacccttata atatttaatc ttcgtgacaa catggggaaa      6600
tattattttc atggtacacg agaggggagg taaggagctc caggtcacac agaagggact      6660
tggaaaaggc cagaccgggg tccatttaag ttggaagctg ggtcaagcat gatacattcc      6720
catagggcca ctcagaacag aggggctggt gcagggcaag agctggaggg aggggaccgg      6780
cctgtgctgg aaaaaacccct gggtcagcag ggagaagagc ggtagataag agatcagggc      6840
tgcaggtcaa cctcctctcc cacccctccc ctcctcctgg accctgctct tcccccactc      6900
ccctctcttg cttgttccac ttcctcatgg ctgtcctgcc ccacttgagt catctgctgg      6960
gtgacagggt agggaggaag tgggcacctg ggccgtgtca ccccgaggag aggtcaggat      7020
gcagatgacc cccagacccc tgggtcgggg gactccacgt gacctcttct gctgctcggg      7080
gcagactcat tggcctccta gtccatctgg gttcttctgg ggctcactca gctgtggagg      7140
tgccaccctc cattctaggt gcgagtagga actagccagg aaagaggaag cgagcctacc      7200
tgggttcatg gtgccagcgg ctgggttacc gaggggcttt ccttggagct ctccagtcac      7260
tgtccagact ggaaggtttt ccttaaccct tgagaacgag aaaacaaatt gtgggatcga      7320
aggtgagcct cctgtgtaca gagggaggct ggaggggctg ggtctttgca gatccctctg      7380
tggtagcagc aaatgtccag agtgtttatc tcctggggcc ctgccagcta gtatttacag      7440
aaactcacct cgttccagct tcctcttccc tcactctcac accaaggcag ggtcctcttg      7500
tcctgtaggg gtatgagaag aagataatca gaggaggggc agccatctga tcattacaga      7560
aactacagag tctatacaca ggaatagaga tgggagggaa cattctgaca atgacctggg      7620
cctgggaaca tgtatgataa ctagttgatg atagccagtg tgtattgtgt gtctgtgatg      7680
tgcatggcct ctgacatgta tctcattcga tgatcacaca caggacagga gatgggtacc      7740
actttcccat ttgaacacag aggaatccac aaaagttagg gaacttatgg gtgttttcac      7800
aatagtgcta gagccaggac ttctgcttca atcccatgtc ttcaattact gtgctctact      7860
cccttaaata tacaatattg agtcatgtat acacgctcat ggtaaatgac tcctcattgc      7920
aaatccctgt ctcacactct gtgctcaact cttcgtcttg gtgaactcac tggtgctgca      7980
gtggacagcc tgtgtcccg ttgcttctct aagattcttt gtcccacaaa gacctggatc      8040
ctgctagatg ccggcccagc cctgctgtg gctgccgagc cctcctgatg cttccccgtc      8100
ccctctgctg tcctccccta gctgatggac cttagggtgt ttctaattct tcatataaat      8160
tatgctacaa agaatatcct ccctcacgta aaactgctca catttgagat tatttcctta      8220
agatactttt aagagtagaa tgactaggtc aaaagctatt aacatctcaa agtttttat      8280 acctagagcc actctgtatg aaaactgtac aaattcacac tcaaactaac aggatatgaa      8340
gatgtccatt ctttcagtct tactggctct cagtagtctt ttcttcagga aaacaaaaca      8400
```

```
aaacaaaaca ttattccttg agacaaggtc tcactcctag tatgcagccc aggctgctgg    8460
caaaatcctg gccttagggg atcctcccac cctgccctct aaagtgctgg attacaaaca    8520
tgagccacga cacccggcct gaataaatgc tgatctttat atagaggaaa gttcttcaca    8580
ttctgctcct gattatctta ccctggggag tgagggaaaa tagcaaatgt taatcatatt    8640
aatcatcttt aggcactgtt ttaagaagac agaagagcat ttatcaacct ccctcctga    8700
gatcaaacta cagccatagt caaggcactt acaggtataa tggcacttaa tgttaatgtg    8760
ggcaaacatt ggtggatttt gcaccactaa ttgctctaag atgttataaa tagtaactca    8820
cagaactctt ccaagaacct aggaagtgtg taccattggt atttccatttt tcaggtaaga    8880
aaactgaaac agatgttcag tgacttgccc aagctcagaa tctactacgt ggtaaagact    8940
gggttcccac ccagacagac ggactcaaga actcacgcac tgcctctgca ccctctgctg    9000
ccaatgaaaa tttaaatgag ggcaacagga gatcagagat gccaagagat gttggaaaac    9060
agaactggct gaagaaatga caactgaata aagaggggtg aagggagctg tgaaccacag    9120
caatgccaag agggcatcca gccaggcaga gtggtctact aggcagagcc tcagagaggg    9180
gaggagttca ccaggcccac gtgccatatg ggattcatgc cagccttgag tctacaccag    9240
tgaaaaaaat cagagagttc atgactgaag caatatgccc cagaaataat atctttgtat    9300
tctgacactt cagtgggttc ccattcaatc accctacagg gaagactgcc agtagacctg    9360
cccccccaccc cgttcaatat gaatagatct aggatcagaa attggagaaa ggtgaaagtg    9420
gggaaacaga ccaagatgac caaatacaaa aggagtccag aacaaacaag taattttta    9480
aatctcaaac ccatgtcctc agggagatta aaaatatt tattcataaa cttaaaacaa    9540
gatatataga aagaagaaa atcaatgaa acaaacaaaa aagagattt tctagaaact    9600
aaaaggtgat gatcaaataa acaagtctag agagaccatg tgaaagaaag tcacggaaat    9660
cctccagaaa ataaaccaaa aagatgacag aggaaaagga gctatatggg aatagaaaa    9720
gttaccaggc acagggtcac agggtgttct aagaaagcta cttgagaatg agccaccggg    9780
aggaagaaag ggtgggtggg tgggtgtgtg tgtgtgtgtg tgtgtgtgtg tgtgtatgtg    9840
ttgtgcatcc atggagggca ggtggggata accaagaaag aaaaagacat gggatccaga    9900
aaacaggaaa atcaacccag agagaaggga atctgaggat cacagtggga catgcagtag    9960
gcctacaaaa cgaccagtcc aggatggaat aaaaagggaa tggttctgtg ggaaaaaggg   10020
actcaataga atacctcaaa ggattcacag tttgagagaa actgaggaaa tgaagaaggc   10080
aagcagtaca agggaggaaa aaaacaaag gcaattagaa acatcaggaa aaagtaaagc   10140
tgtgccacaa acatgtgca aacatggtgt acaactcagc tccacagtaa atagtattta   10200
aaacatcaca aaatgtaaac actcttgatt gattttaac tttgagaaca gaacagagca   10260
tataaatatg agaactaaat atacttgtta ccgattagta caaacttaaa gcacaaaggt   10320
agcagttggg atgtgaagca ctgaacgaag gagaaggagg attaatattg tcatcttta   10380
aagagggag tcaagaaata ctaggtaaaa ctgagagtat aagaaagaaa gttgtaagta   10440
aattgtttac agctacaaag ttgctaatgg aggacataaa actggtgata caatattagg   10500
aaaaggtgga gaggagagat agagggagtg tacaaacaag atgaaaatga ctaataatga   10560
cactataagt aataatgata ataccgattc aggcccatcc cagttagggg cggctccaaa   10620
atcaccattg ttctttttctc accttgtgtc tctgcgcact ccccggcaca cccacttcca   10680
gcagctggtc tttgtttgca gactttattt taacagctca gtggttcccg ggcatcctcc   10740
agctcttata caaaagcccc ctcctcaaaa gccactcgcc tccctctttc cacttcccac   10800
```

```
ctctgtttca gggtcgaggc atccagatat ctgtcttctg gggcccctac gcagcaagac    10860
taaaaggggg acccagtcct gggcagcagt tcaccagggg agtatgcaga ggggcatctg    10920
gacacttctt gctgtaaggg acggggtgac gggaggggggt cttcccttcc ccttcttcct    10980
gctttgttca ctctgtgaca ccctaggcca ggggagctgt ctcaacgcca tctcatgagc    11040
catgagaacc aggaggacca ggagggagaa gaggagcagg agggcagaca gagctggggc    11100
ctcggacctg cccaatactt gtgaggagct gcatccagga tcccatcctc ctgggtcatt    11160
gttggcctgg ctcccacctt tgtctggagc ctctgctggg ggttgaggct ggatactgcc    11220
cctcaggctt gactaggaca cagtgtgtac tccatgggtg agcctgcagg ctggtcaatt    11280
ccggtgtcca actgagcgac ctggaagagg agccctccct cccacctcag ctctgagcca    11340
agctctccag atgcagagga cagggactct cagcaaagca tctccctcca agtggttgtg    11400
gggcatcctc cttgggcagg gaaagaggag tcgaaatgat ttcctgagaa atcgtcattt    11460
tcattttatt tttgagaaac tgtcttgctc tgtcacccag tctggagtgc tttgggcta    11520 tcacagcttg ctgtagccta gagcccctgg gctcaagtga tccttctgcc tcagccttcc    11580
aggtagctgg gactacaggc acacggcacc atgcaggact aatttgttaa ttttcattt    11640 cagagagaca gcatctcctg tgttgcccaa gctgtcttga gctcctagca tcatgtgatt    11700
ctcccgcctc tgcctcccac agcactgaat tacaggcctc agccgtggca ctgcacccctt    11760 ctgaggaatc ttcagtgaaa agccacggtc aagttcaaac cccatagcag ggcacacagg    11820
ccctctgatg ctctggaccc caccttcctc accgctccct gccaccacag tcaccttagg    11880
tccaggcacc cactgacgcc ctgcttcggt gcctcctgga gccatctac tcctcccact    11940 cccatcccca gcctcaggcc ttcactcagc tgctccctcg ccctggaatg tccccccac    12000 tgtccccacc atgtgcaagt cacctgtcct cagagaccca cccaaagctg cctggtccat    12060
gcggcggccc ccaaccctcc ccaggctccc tgagcactct gctttccaga gggagctcta    12120
cctgtatgtg gctctttggg cctctgtctc ccctttagac tctgaacatt caatggggac    12180
actgttgtgt tcccagctgc accccctacg actgacctgg atgccctccg ccctccctgg    12240
cacagcctgg ctgaaatccc aggtgcagga ggcattactt gaactaaaag caaccagcct    12300
ctggatgaca tggcccagct tcagtttcac tttcagttga gaaattgaat ttaattttc    12360 tttctatctt gatgggcatc tcttttggt gaagaacaaa taagaccatg actcatattt    12420
cacagaaatt acccccctga tttcatggac ttttggcagc tctatcaagt tttttagagg    12480
ggaaaaatct taggctggga ggggaggtga cttgcccaga gtcacacagc tcttggaggg    12540
cagaggggag gccaacatct gcccttgtga ctctgatatt gaagcaaaaa tgggtgattt    12600
taataatcca acagtgtcca ggtttgattc tgcttctaca aacacagaga cctaagctct    12660
cactcctgta gttatactca caattccaca gtgtggcttt tgaatctcat gattgcaaag    12720
ctggcatcat gccacaggta ccattctgca atgcgacctt tcactccc tgtctcagcc    12780 atgtttccca ttagggacac agcacagcct gtttcttctc tatcagctca gaggtctgaa    12840
cagagggaca gaggtgaggg ccagagacgt gaagtcctat gatctgcctg ctcagcctcc    12900
tgacacggga ccctggcaag tcattcccct cccagggcct cagtttcccc acagggcctg    12960
gcacaagtag gtgctcagac tcagggtgag tgagacaacc tctgagttcc ttgtgtctca    13020
aaagaaatct gttgttccca ttgggcttca gcagcagcac cctggggcca gcctgggtgt    13080
ggcccggcca caaggacatg ccgggctcca ggtcacctcc cctcctccac cttctttgat    13140
```

-continued

```
tccttcaaat tcccaaaga gatgggcacc cccaacacct acctttcttc tggggtcagc    13200
tggccgtgtc tgagggtgtc agaaccagag ctgagcccgg ggagctttgt gaacccatct    13260
aagctgtttt ccccacctct ctctacagtt tacccgccca gcaggaggga gggagcaatc    13320
agactcaagc ctgggtgcaa atcccggctc tgccactgct ttcctgtctg atctgaacca    13380
gctacctaac ctctctgagc ttatctacaa aagctgaatg atccttccct tatagagcta    13440
ttgcaagaat aaggacatgg gggtagatca cactatcccc aacttaccaa gggatcttcc    13500
tctgacagag actgagcaag atccaactgt tctgagctgt gtggatccca cgtccagctg    13560
tgcatctgtg taataaccag acacgtcctc cggcctccca gatataccct ggaattcgaa    13620
agggaaagtg aaagtcacaa cttcccagca gctcatgacc aagcacagta aacacgctgc    13680
tccccagcac cacctgcagt ccaggcccag cctccttgct gctgcactta gaggagcagc    13740
cgcagaccag acatccgggt ccctctcatc caacccacct gcctcacatc ctcaggattc    13800
aaggtctgct gtgtcagctg cccatgtctc aggcagtcag aaccagagtt gagcctgggg    13860
agttttttga acccatctga gccgcttgcc ccccaacccc cgccccgatc tctgcagttt    13920
aagggcacag caggtgggg agagaagtca gactcaagcc tcagtgcaat tccaggctct    13980
gcccctgttt tactgtctga tctgaactag ttacctaacc tttctgagct caagaaagac    14040
ctgccactga ctgaccgtgg ggctctccag attactcccc gtccttccgt tccccacat    14100 tcctcagatg cctgccttac tcccacacat gccatcagca tcagcacagt cccccacaca    14160
tgctgggtgg atgcttattg catatttatt gtaatgcttc tgaggttatg ttttctgtta    14220

tgtttttgat atagagtctt gctctgtagc ccaggctgga gagcagtggc acaatcatag    14280
ctacttcaag tggcacaatc aagccatcct cccatctcag cttccgagta gctgggatta    14340
caggtgcctg ccactacacc cagctaattt tttgtaattt tagtagagat ggggtttcac    14400
catcttggcc aggctggtct tgaactcctg acctcaagtg atccacctgc cttggcctcc    14460
caaagtgctg ggattacagg tgtgagccac ggcgcccagc ccattgtatc cttcttgtga    14520
ctttgtgtct tcatagctta gctcctacta ataaatgaga acatacaata tttggttttc    14580
cattcctgag ttacttcact cagaataatg tgtccaact tcatccagat tgttacggat    14640
gccattattc ccttcctttt tacagctgag taatattcca tggcatatac atatataggg    14700

tgtgtgtgt gtgtgtgtgt gtgtgtatat acacacacat tttcttcatc cacttgttgg    14760
ctgatgagca tttaggttgg tccatatttt tttcggttgc aaattatgca gctataaaca    14820

tgcatgtgcg agtatctttt ttatataata acтттттcтcc tctgggtaga tacccggtag    14880

tgggattact ggatcaaatg gtattctact tttagttttt taaggagttg ccatactgtt    14940

ttccatagtg gttgtactag tttacattcc caccaccagt gtaaaagttt tcccttgtca    15000
ccatattcac accattttag ctaggctggt cttgaactcc tgacctcaag tgatccacct    15060
gctttggcct cccaaagtgc tgggattaca ggtgtgagcc actgcaccct tctattcttc    15120

tttgattttt aaattatggc cattcttgca ggagtaaggt ggcaacttat tgcagtttta    15180
atttgcattt ctctgataat tagtgacgtt gagcacattt tcatatttt ttggccattt    15240 cattttgtat atcttctttt gagaattgtc tattcatgtc ctttgcccac tttttgatgg    15300 gattattttt ттттттcттgc tgatttgttt gagttccttg tagaaactgg atattagtcc    15360

tttgtcaaat gcacagtttg caaatatttt ctcccacttt gagggttgtc tgttttctct    15420
gctgattatt tattttgctg tgcagaagct tttactttta attaggtccc atctctttat    15480

тттгтgтттc gttgcattta tttttgggtt cttggtcctg aattctttgc ctaagccaat    15540
```

```
gtctggagga gttttttccga tgttatcttc tagaattttt atggtttcag gttttagatt   15600
taagtctttg atccatcttg agttgatttt tgtatgagga tactgtttca ttcttctaca   15660
tgtggcttgc caattatcct ggcaccattt gttgaatagg gtgtcctttc cgcactatac   15720
gttttttcttt gctttgtcaa agactagtta gctgaaagta tttggcttta tttctggggtt  15780
ctctattctg ttcccttgat ctatgtgcct attttttatac cggtaccatt ctgccattat   15840
gtaccttttt tttttttttt tttttttttt tttgagatgg agtctctctc tgtcacccaa   15900
gctggagtgc agtggtgcga tcttggctcg ctgcaagctc cacctcctgg gttcatgcta   15960
ttctcctgcc tcagcctccc gagtagctgg gactacaggc gcccaccacc acacctggct   16020
aatttttttt tttttttttt tttgtatttt agtagagatg gggtttcact gtgttagcca   16080
ggatggtctc gatctcctga cctcgtgatc tgcctgcctt agcctcccaa ggtgctggga   16140
ttacagatgt gagccactgc acccagccct tgtaccttttt aagtgaacca tttagcccat   16200
tttcattcaa tgttagtatt gagatataaa gtgctgttct attcatcagg caagttgttg   16260
cctaaatacc ttattttttt cattgtgtta ttgttttata ggccctaagg cttataaaac   16320
aatatgctgt aaggaggttc tattttggtg tatttcgagg ttttgtttca agacttagaa   16380
ctccgtttag catttcttgt agtactggct tggtagtggc gaattctttc agcatttgtt   16440
tgtctgaaaa agactttatc tctccttcat ttatgaagct tggttttgct ggatacaaaa   16500
ttcttgacta acaattattt tgtttaagga ggctaacaac aggactccag tcccttctgg   16560
cttgtatggt ttctgctgat aaattagctg ttaatctcat agattttcct ttacaggtta   16620
ccttatgctt ttgtctcaca gctcttaaga ttatttcctt cttcttgact ttagataccc   16680
tgatgacatg tgcctaggtg aggatcattt tgtgatgaat ttcccagatg ttctttgaac   16740
ttcttgtatc tggatatcta gatctctagc aaggccaagg aagttttcct caattattcc   16800
ctcaaataag ttttccaaac ttttagattt ctcttcatcc tcagcaacac caattattct   16860
taaatttggc catttaacat aatctcaaat ttcttggagg ctttgctcat ttttttaaaat  16920
tctttttttct ttgtctttgt ctgattgggt aatttgaaaa gctgtgtctt caagctctga   16980
agttcttttct tctacttgtt ctagtctatt gttgaaactt tccagtgcct tttgtatttc   17040
tttcagtgtg tctttcattt ccagaagctg tgattgtttt ttctttgtga tatctatttc   17100
tctggagaat tttcatccat attctgtatt ttttaaaatt tctttaagtt ggttttcacc   17160
ttcctctgct atctccttga atagcttaat aatcaaccttt ctaaattctt tatatggcaa   17220
ttcagagatt ttttgttggc ttgtatctat tgctggggag ctagcaatag ctttgggggg   17280
tgttatagaa atatgttttg tcatattacc agaattactt ttccggttcc ttctcatttg   17340
ggtagactat ttcagtggaa agatctgaaa ctcaactcct tctgttcagg ttcttttgtc   17400
ccacgggtta ttccttgatg tggtactctc cttctcctag gaatagggct tcctgagagc   17460
cagactgcag tgattgttat tgctcttctg ggtatagcca cccactgggg ctataccagc   17520
ctttgggttg gtgctgggga atgtctgcaa agagtcctgt gatgtgatca tcttctggtc   17580
tcctagccat ggataccagc acctactctg gtgtaggtga caggcgagtg aagtagactc   17640
cgtgagagtc attggttgta gttctcttta gtgtgctgtt ttctccaatg ctggttatgc   17700
tagcagtgaa gctgtcatgt ggagagactg aggacctctg gtcagtcagg atgttgcggg   17760
cagtggtatt agctccttgtc ttctccttcc tgggaatagg gttattctgt catgagttgc   17820
tgtaatggcc tgagttggtt ggtctccagc caggaagtgg cactttcaag agagcaccag   17880
```

```
ctgcggtagt agaagggaga tacaagcttg ccctaggttg accagggtaa gtattctagt    17940
ttctcaggtg attggcaggg ccataaagct cccacgagtt tatgtctttt gtgttcagct    18000
accaggataa gtagagaaat accatcaggt ggagggcagg gttagctggg tctgagctca    18060
gactttcctt aagcagggct tgctgcggcc actgtgaggg atgcagattg tcctaaggcc    18120
aatggggttt gttacagagg ggattatggc tgcctctgct gtgccatata gttcgccagg    18180
gaagtggggg atagctggca gcgagaggcc tcacccagat cacatgcagt ggcaaggct    18240 ggccttgctc ccgcagtgcc ccactaacaa tgccaagttt agattcaggc agcctgtgcg    18300
cagaactcag accttgtccc aggccataag cttctccact gagaaagcaa gcatggcttt    18360
caggccttgc ctctccccat ctgcccacag tgtcagtggt ggctcctggg ctcatatttg    18420
cagaagttcc tgttctcccc ctggattctg ctcaagaaaa ttcaagccca gtagaaatta    18480
ttagaaaatc catctggaag cttctttcac cctgtgaccc ctcccaaatt ctgctggctg    18540
cttttcccaa aggcctctgt gagataccgc cagggatggt gccctgggct tgagctggac    18600
actgggaatg cctacaggat tcttcccact tctgcttcta cttttacatt ttgcatggtt    18660
ctctgaatcc atttcagcta tgggtaaggt taaatccctc tcctgtaatc tggattttca    18720
gattccccag gggcgatgtg tgtttggagg cagatttttcc ctccctcaca ctttgggaac    18780
tcccagtttt ttgcctgtct catagaattg gcaaggagca tgccacttct ttcaaaggat    18840
ctgtgaattc tttcagtttt cctggtacat tcctgtggtg gttcttggca cacattatta    18900
catgatgtgg gtctccacat gctgtccggt ccttccaagt gggagctgca tgttagccct    18960
gtctcctatc tgccatcttc ctcagacttc taacattaac ttttaaaaag cttggtggga    19020
agagaccagg gccaaagttc tccttcttgg agatgaaagc caagaagcac ttcctttggg    19080
acaagtcaga aaaatcctga ccaaatcaat gtgtgttcct ggcgattctg cccaggcct    19140 atttcctccc catctgagga attgcacaaa cacagcagaa cccttctgct ggcccaggac    19200
atggagaggc tggagtgaag ttgatcagag ctgggatgga tcctggcttc tgtccctgca    19260
cagctgtggg cctctaggat tatgccttgg agactggcat ctggcgtctg gcatctgtcc    19320
aatgggaata gtaattcaat catataggag gatggtgaag gccttagagt gaactccagg    19380
tcaaaggtgg gggaccaagt accatgatcc tgccgaaaag tccagataga cctggaccag    19440 ggcagaacc agggtcagg atgggcataa gtgggcctaa ttggaaggta agtaggaagg    19500
ctgggacacc agggccagga ctagggtgag aggagggagg caccaaggac accaaacgta    19560
aggaggtcat tgacttgcag aggacacatg agtgggagag ggatatttct tccctccctg    19620
atttgatccc atcagtgatt ggcatagtgg gccgtgagtg acggtttccc ccacaccaag    19680
cctgagaact gtgagaactg tggagttttt gcgtgccctt tgggaccctc ttgtgttcta    19740
catagagtag cccctgaccc tgggaaagca gtgtggctta gtgaccactt ccggagtcag    19800
aatgggtggc tgccaatttt tgtaatttca ggggttctga ggaaacccat aagttgccaa    19860
ccaaagagga aaacacttcg tctaccatct tgtccaaatt caggtctttt cagcattagc    19920
aatttatata gatggttctg aaagtgtctt gagtcttcta gaggctccat aaaattgcac    19980
atggccttgg caagcacaga ggtgaagcca tcactcctta ggcatcgatt aggctggtga    20040
catctgaaag tgagacctgg aaggttggag gtgcaggtgg taggtcagga ggcagtaagg    20100
tggctggaga atccatgtgg actctccaaa actaatagcc aggtctcctc ctccagtcaa    20160
ctggtgcggt gcttggaacc agtgaccatc agtcagaagg tcaaagggca tgaggcattg    20220
gaagagagca gatgccaggc aaagtgatct tgtgtaggtc tgttttttggt tttgtttgaa    20280
```

```
ttctgagtac tcagagttac caaaactgca atgtctgagg gcacccttat ctttgacact    20340
aactgcaaat ttaagggat tcctaaatcc gtccttagat tttataattc actagaggaa    20400
ttcacgtaac tcactgaaaa ctgttattgc atgactgtgg tttatacag ggaaaaaaca     20460 caggttaaaa tcagcctaag gaagacacac agggcagagt ctaggagggt ttcaggtgtg    20520
aagcttcgtt gtcctcagga ggctgcgttc tcctgtgtca atgtgggaca aaacacatgg    20580
ggtgttgcca accagggaag ctcacccagt taaggaaaaa ttcctgtgaa tcacattaaa    20640
tcaggaagaa agcctttatt caggattgtt gttacagggg agggagactg agcccagctc    20700
ccaatacagt aaagacagag ggggagtcac agccaacacc agagtgaggg gcagcagatg    20760
gaacaggact gacaggaggc accagagtcg ggggttcatg ctaaactggc ctaacaggat    20820
tttccctaaa ggcaggtcag acactcaccc atcaagggc aggtgaggag agtgatcaga     20880
tagcaagtgt gctcagacag taagaaggga ggaccctccc taaactgact cgggggatt     20940 cttgctgagc cagggttgtg caggcccagc aagcacggga tgggcatgga aggccaaggt    21000
tggtgcctag aggagaagag gctcagaaga gcccaactgg agtctggtca aacagaaagt    21060 cttctcaac ccatgcctta gtgtccagag tgtttgctgg ggcttgacca caggctgcac     21120
tcatggctga cctggagttt ccagcccctc cctgaggtct cacacccttta gtccccagat    21180 cctctggtgg tgagaagaga tacccaatag ccccaaaccc ccatcatcca tcacatttgc    21240
tatactgtcc tgtagccaaa ccaccaggga aacaaagaca ttcctaccag gcagggcatt    21300
ccaggggcct ggagatcact tcgcaggggt aggggacaat gggaagacct ctcctgggat    21360
aaagttaatt cttcactgcg caattgtagt gcagtgaaga ttctattccc agaggccggg    21420
gaaggtttgc aattgctttg gtgcagtggg gcatgggtaa acttgcacct tagctataac    21480
agcagacaga acaaccatag tacaaataca ggtagtcagt tgtgcaactg tgtattggta    21540
gacacaatga cagcacatca ccggctaacc ccacaatatg gggtgactac ctgtacaaca    21600
atgtcaccaa gcccttgggt taagcaatga tacatggctg ggttggtaga ataagtctct    21660
gcatatgggt gcctaccaat ccccatggag atggagatgg ctgtgggcct gtgtcaccca    21720
cccttggcct tatttgccat tcaactggac tggcagatgc atctcagggc atccttaatt    21780
gccacagtat atagttcccc atttagacac gaccccagt aactggaaaa cggtaaaagc     21840
tagagattac cagatatgtg catactgtg gttctacccc ttggccatct ttgcctccaa     21900
agtggcaact gtaaatgcag agctgcaatt cgtgtgctgg ctaaacacac agctgcagcc    21960
ttcaatgata ctcaccatcg tttacactt cccaatcaag aaaccaccca gatcaggcat     22020
gttcctctgc aaaatcgtat gacccaaaat catacaactg ctgcccatgg tggagcttgt    22080
gcattaatta aaacaaaatg ttgtgtatat agccctcatt actctcataa cataacacag    22140
gctctgctga cgttagatac ccagagtcca gccacagagt cttttgtctta tgatcttatc    22200 acctcatggt ttaatcaact cccagacacg tggagaaact ttgtatctag cgtaattgca    22260
attgcgttca taatccttttg ttgaggttag tgttgctgct ggggtgtctg gctgcaatgc   22320
tcttccacaa aactggcccc aggaaaatca cagaaaaaca gtgtgatgag attgtgaggg    22380
ccattcaagg ctatgcaggg gtgtggagag catggtgggc atgtcccgtc agacagcaat    22440
aactgaagca tcccctaaga ataaccctac attccttggt gaattttgc tcagtgttcc     22500 aaggtatgga tcccgggaat ggccaatcca gatgtttaca tcatacttat gaagaactct    22560
gttccttgga tcagaggttg tgcaaggaat caagacctt tgtttgggc taggtggagg      22620
```

```
tttcctggca gaggtgctaa gtggaggttg ctctgggaag aatatcatat aacctgcatg   22680
catttgacaa acaggagggg atttcttgtc ttgcctgctg ctcctgggca acctgtacat   22740
aagctccctg aataaagctt atgtctcacc tgctgtctcc aggtcttttc ttctgtctct   22800
ccaagtctgt gtcctgtcag ctcattagca taggggtcca gcatgacaaa tataaaacgg   22860
tgtttaacat tctttggatt atgtttatat aaatgtgtta ttaatatgtg ttccaaaatt   22920
gtacgagatt ctataggtct aatatgtctt ggcatatgtt atcagaaact attattatta   22980
ttatgttaag tagttgtttg ccacagaaat aaagtaattt ccttgtcgaa tgtgtcttta   23040
ccaatgctgt tctcatactt ttgttatctg caaaaagtgt ttactttaca tctcaaaaaa   23100
cagtttatga tcagctacag attgtgccat cggactaaga aaaaaataaa tcttccagga   23160
ctgtaattca aaagttgatg tggtcatgaa gattgctaac ccaatatcaa gtggaagaag   23220
gttattacat gggaatgaat taatggagaa caaaaataaa ttttttaatga cttttttgttt   23280 aatatacgac tgattctttt gttttgtttt tcttagtcaa gaaaacttct tttttccctttt   23340 gggctccatg tagcttttaa caattgaata agtatactc ttgtgagcaa aatttgaagc   23400 atatttctttt ctcactatct gatttctcca gaatttggaa actatttgtg agtattctta   23460
gttcatggca atagagttat ttgcataagt tcagttggaa tctgttttct ttcataacag   23520
gacacaacta gagacactgg ttattttacc aaggctttga ctggcatggc atatttccac   23580
atgtacgtag gctgctttga gtaatggtgg ctggcttata gagccgatga aagcctcttt   23640
gaaaaatttt cctcaaactt tgcctataca gttcctttac agggttcctg tcctgtggta   23700
agtaaagaat gtcactttct gacaggccca ggaagcccaa gttaccttgg gaccttgagg   23760
agaaaggaac tcacctaata tatataggca tctgcaggca aatataaatc actggctgag   23820
cttgagattt taaaaggcct actctgagat atcttatgaa aaagaaaata ttgtagcaaa   23880
gtcaatttcc aaaaggagcc catatgccaa ataagtattc ttgctgcact ttatacaaat   23940
gatcaggcca agaaccatca gactaaaact tctgttgcaa ataaattagc cctactatga   24000
tttgtctttg gtagaaatac aggactagag agagaaaagg tatgtttcaa aagaaactag   24060
agaatgcctg ttattggatt ctagcttttct ccattgtttt ctagccgtat tgtttgtcca   24120
cagtttatct ggactacata ctgaattctt tcctggccac aagtctccaa actaatatttt   24180 tgcttttctt tttctctcat ttttctgact tggaatcacc agaaatccaa actgtgctttt   24240 tcttaaagtc ctgcaaactg aagcttgaaa actgtgttat agtgaaggaa gagaaagacc   24300
ctctcatatt attttttatat tgtttttgtac tcagtacctg ttttaagaaa aaacaacaag   24360
gaagtaaaac caaagacagg cagcccggcg ccaggcccga aaccaggcct gggcccgcct   24420
ggcctaaacc cattagttaa aaatcaactt atgattcaga agccgatgtt attcatagat   24480
tccttacatt atgtagaaga acattgtgaa actccctgcc ctgttctgtt ccccccctgac   24540 gacctgtgta tgcagcccct gtcacgtacc gcctgcttgc tcaaatcaat catgaccctt   24600
tcgtgtgaaa tctttagtgt tgtgagcccct taaaagggac agaaattgtg cactcaggga   24660
gctcggattt taaggcagta gcttgccgat gctcccagct gaataaagcc cttccttcta   24720
ctactcggtg tctgagaggt tttgtctgca gctcgtcctg ctacaataga attcagacca   24780
aactcgtgac cagagactca tttgcttcta cagtgttttg tccaaaagat gttgaagaac   24840
ggccaggcgc agtggctcac gcctgtaatc ccagcgcttt cggaggccga ggcaggcaga   24900
tcacaacgcc aagagatcga gaccatgctg gccaagatgg tgaaacgctg tctgtactaa   24960
aaatacaaaa attagctggg cttggtggtg cgtgcctgta gtcccagcta cttgggaggc   25020
```

```
tgaggcagga gaatcacttg aacccgggag gtggaggttg cagtgagccg agatcacaac    25080
actgcactcc agcctggcaa cagagcaaga atctgtcaaa aaaaaaaaaa aaaaaaaagt    25140
tgttgaagaa caaggagaaa acgtgaaagg aaaatcaaat cttgggaccc caaaactcac    25200
tggaaacagt taagcttaga aacggagtca ctccaaaacc tgcctttgtt tttgcttcta    25260
agcagatatt tgcgaagaca aaaggcaaca tgttccccag gtagcctcct tcacaaattg    25320
ctcacaagga aactccttgt gggtcccagc agtttttacc ctgaggcaga ctttgtgtaa    25380
tttcattgtg acaatgcaaa ttagcaactt atctttactg gtacatgata aataacaaga    25440
cttctgccca ccctcagaaa aatgcacata tgcctgcttc ctctactcta tgttcatttt    25500
tatcttatat aaaatgtaga cgaactgtgc atgagacgaa tgaataattg actgttcctc    25560 tacccctcc tttcatagac aacctgtgga ttcaaggagg gctaatcaaa gcttcacaag    25620
aatgtgacca ctcacctcat tacctatcct gtctttttc ctttcctcct tccactcctg    25680
cctgatttta cacatttaaa tactggaggc ctcaaaaccc tctgtgaaaa acgagtggac    25740
cccagaacct cctgtgactt gtgtgacttt ttcctgggtg catcctcaac cttggcagag    25800
taaacatcta aactgactga gacgtgtccc agaccctctt tggtttacaa gtcttgcctc    25860
ctccctgagt tgctggatga aagcaacgtc ctctcttctt gcctcagttt cctcatctgc    25920
aaaatcagat cataatcctg gcccattgag gggatgatta taaaactcaa tcaaatggag    25980
aagcatttgc aaatggaatg tattgcaaag tgtattgtgc agtccctgtg taatcaccat    26040
tctcttcctg cctcataagc tggtgtgtgt gtgtgtatgg gtggggtgag gtggacacga    26100
tgcccccaga gatgtttgct caggatgaaa taggccccca tggaagggtc aggttggctt    26160
ctgtggttta gctgcctttg aggcccttct gcctggggca aagcacaaaa gtccaatagc    26220
aatctggttg catgacttcc tagtcatgga agtgtggctg agcagtggtc tctagtccct    26280
ccaccctgtg tgcctcggga gtggaacacg gggcagtggc ctctgctggg gaggatgctg    26340
ggggatctct gaaaggaggc aatgcctgat tttgtcactg aacgatgagc atgatttttc    26400
caggcggtgg aagcaggtgc tcccggcaga agaccccata taagcaaata tctagaagcc    26460
acaaggcatg gccttcaaca agagcaggcc tggtgcggtg gctcatgcca aggtgggagg    26520
atcacttgag gcctggagtt caagagtagc ccagtcaata tagtgaggca ccatctctaa    26580 tataatttt ttaaaaatta gctggtggt tggctgatac ctgtagaacc agctactcag    26640
gaggctgagg tgggggatg gcttaagccc aggggtttga agctgctgtg cgcgatgact    26700
gtggcactgc aattcagtct tggtgacaga ctgagaccct gtctcaaaaa cataaccaaa    26760
ataaccccaa cggcattaca ataaatatac aataagcatc cacaaggcat gtgtgggaga    26820
ctgtgcttat gccgatggca cgggcaggag taaggcaggc atcaggggaa tgtggatgca    26880
cgggaggatg gggagtaatc tgcagggtcc catagtatgt cagtggcagg tctttctcct    26940
tgagaccaca gcagacccc agccctgagg atgcgaggca ggtgggttgg atgagaggga    27000
tctggatgtc tggtctcagg ctgctcctct aagggcagca gcaaggaggg tggggctgga    27060
ctgaaggtgg aggggagcgt gtttgctgtg cttggtcatg agctgctggg aagttgtgac    27120
tttcactttc cctttcgaat tcctcggtat atccttggga ctggaggacc tgtctggtta    27180
ttatacagac gcataactgg aggtgggatc cacacagctc agaacagctg gatcttgctc    27240
agtctctgcc aggggaagat tccttggtaa gttgggggaca gttgacctgc ctccatctta    27300
ttctcacagc ttttgtagat aagctgggag aggttaggtg actggttcag atagacagga    27360
```

-continued

```
aagtagcggc aaagcctgga tttgcaccca ggcttgagtc tgattgcttc ccctctcctg    27420
ctgggctctt aaactataga gggttgggga aacagctcag atgggttcac aaagctccct    27480
gggctcagcc ctggttttga ctgctgagac acgactgagt gaacccagaa ggaaggtttg    27540
tgttgggggt gcccatctct ttgggaaatt tgaaggaacc aaagaaggtg gaggagagga    27600
ggtgacccag atcccagcct gttcttatgg ccaggccaca ccaaggctgg ccccagggtg    27660
ctgctgctga ggcccaatgg gggcaacaga atttttttc aggtacaagg agttcagagg     27720
tcatctcacc caccctgagt ctgagcacca acttgtgcca ggccctgtgg ggaaactgag    27780
gccctgggag cggaatgact tgcccagggt cccgtgtcag gaggctgagc aggtagatca    27840
taggactcca cgtctctggc cctcacctct gtccctctgt tcagacttct ggggtgatgg    27900
agaagaaaca ggctgtgctg tgtccctaat gggaaacgtg gctgagacag gggagtgaga    27960
agggtgcgtt gcagaatggt gcctgtggca tgatgccagc tttgcaatca tgagattcaa    28020
aagccacact gtggaattgt gagtataact acaggagtga gagcttagat ctctgtgttc    28080
atagaaggag aatcaaacct ggaaactttt ggattattaa aatcaaacat ttttgcttca    28140
atattagagt cacaagggca gatgttggcc tcccctctgc cctccaagag ctgtgtgact    28200
ctgggaaatt caccctcccct cccagcctga gtattttccc ctgtaaaaaa cctgatagag   28260
ctgccaaaag tccatgaaat caggggggta atttctgtga aatctgagtc atggtcttat    28320
ttgttcttca ccaaaaagag atgatgaagc ctgtaacccc agtgctgtgg gaggcagagg    28380
cgggaggatg acttgaggcc aggagttcaa gacagcctgg gaaacacagg agatgctgtc    28440
tctatgaaat caaaaattaa caaattagcc cagcatggta gtgtgtacct gtagtcccag    28500
ctactcagaa ggttgaagga ggcggatcac ttgagcccaa cagatctagg ctgcaatgag    28560
ctaggatggt gtcaaagccc tgcagcctgg gtgacagagc aaaactgttt attaaaaact    28620
aaacgaaagg ccgggcgcgg tggctcacgc ctgtaatccc agcactttgg gaggccaaga    28680
caggtggtca cgaggtcagg atatcgagac catcctggct aacatggtga aaccctgtct    28740
ctactaaaaa tacaaaaaaa ttagccgggt gtcgtggcgg gcacctgtag tcccagctac    28800
tcgggaggct gaggcaggag aatggcgtga acccgggagg cagagcttgt agcgagccta    28860
gatcgcccca ctgcactcca gcctgggtga tagagcgaga ctccatttca aaaaaaaat    28920 gaaatgaaaa tggtgatttc tcaggaggag cacactgtct caacccctct tttcctgctc    28980
aaggaggagg ccctgcagcg acatggaggg agctgctttg ctgagagtct ctgtcctctg    29040
catctggtga gcttggctca gagccctgag gcgggaggga gggctccctg tctgggctgc    29100
acaattggac tgggcttggg ctgggccagg gccatctggg cttcttctag gaaccaaagt    29160
cacttcccgg aattgaccaa ccggcagact cgcccaggga ggacccgctg tatcctagtt    29220
gaggctaacg gtcaatatcc ggcctcaata ttcagcagag gctccaggtc agggtctgag    29280
ccaggccaac aatgaccaag gaggatggga tccagggtgc agctcctcac aagtgtcggg    29340
ggaatccgag gcaccagctc tctctaccct cctgctcctc tgctctctcc tggtcctcct    29400
gtgtcctcat ggctcatgag atggtgttga gatggctccc ctggcctagg ggatcacaca    29460
gtgaacaaag caggaagaag gcgaagggat gcccctctcc tgtcacccct gtcccttaca    29520
gcaagaaggg cccagacgcc cctctgcata ctcccctggt gaactgctgc ccaggactgg    29580
gtcccccttt tacccttgct gcatggagtc cccagaagac aaacatctgt gtgtctgaac    29640
cctgagacaa aggcaggaaa gggaagagg gaggcgagtg gcttttgagg aggggctttt    29700
agtatgagag ctggaggatg gaaccccatc aggggggcccg ggaaccactg agctgttaaa    29760
```

```
ataaagtctg caaacaaaga ccagctgctg gaagtgggtg tgccagggag tgcgcagaga    29820
cacacggtga gaaaagaaca atggtaatgc ttggagccgc ccctaactgg gatgggcctg    29880
aaatggtatt gttattattt atagtatcat tattagtcat tttcatctta tttgtaccct    29940
ccctctatct ctcctctcca ccttttccta acattctatc accagtttta tgtcttccat    30000
tagcaacttt gtagctgtaa ataattact tacaactttc ataccctc agttgtaccc       30060 agtatttctt aacttccctc tttaaaaaaa tgataatatt aatcctcctt ctccttcgtt    30120
cagtgcttca catcccaact gctacctttg tgctttaaat tttgtactaa ttggtgttga    30180
taacaagtat atttagttct catatttata tgttgtgtat atgttttggt ttttttttgt    30240
cttaaacaag agactactga gagccagtaa gactgaaaga aagggcatct tcatatactg    30300
ctagtttgag tgtgaattgg tacaatttgc ctgcagtgtg gctctaggta taaagccttt    30360
tgagttgttg atagcctctg acctgctcat tctactccta caaatatctt aaggaaataa    30420
tctcaaatgt gggcaaagtt ttatgcgaag aaggatgttc tttgtagcat aatttatatg    30480
aggaattaga aacaccctga ggtccatcag ctagggaaag acagcagagg ggacagggca    30540
gcaccaggag ggcttggcag ccacagcagg ggctgggctg gcatctggca agatccaggt    30600
ctttgtggga caaagaatct tagagaagca acggggacac aggctgtcca gtgcagcacc    30660
agtgaattca ccaagatgaa gagttgagca cagagtgtga gacaaggatt tgcaatgagg    30720
agtcatttac catgagcgtg tatacatgac tcaatattgt atatttaagg gagtagagca    30780
cagtcattga aaacatgggg ttgaagcaga agtcctggct ctagcactat tgtaaaaaca    30840
ctggcaagtt ccctaacttt tgtggattcc tctgtgtttg aatgggaaag tggtacccat    30900
ctcctggcct gtgtgtgatc atcgaatgag acacatgtaa gaggctctgc acatcgcaga    30960
catgcaatac acactggcta tcaccagcta gttatcacac atgctcccag gccctggtca    31020
ttgtcagaac cttcctcccc atctctattt ctgtgtatag actctgtagt ttctgtaatg    31080
atcagatggc tgcccgtcct ctgattatct tctcctcata ccccaacagg atgagtgcac    31140
ttttccttgg tgtgggagtg agggcagagg aagctggagc gaggtgagtg tctgcaaata    31200
gcagatgatg ggggctcagt gatagacaaa caatctggtt taggttggtc ttggtgtttg    31260
cttccacccc agagagattt gcagagcccc ggctgctcaa gcaagcctcc ctctgtccac    31320
tggtggctca catttgatcc cacaatttgt tttctcctcc tcaagggtgc aacaaaacgt    31380
tccaagtggg acagatactg gagatcctca aagtaagccc ctcggtgact gggctgctgg    31440
caccatggac ccaggtaggc tcacctcctc ttccctgctg gttcctactc gcacttagaa    31500
tggagggtgg cacctccaca gctgagtgag ccccagaaga acccggatgg actaggaggc    31560
caatgagtct gcccaaagca gcagaagagg tcacgtggag tcccccgacc cagggggtctg   31620 ggggtcatct gcatcctgac ctctccttag ggtgacacgg cccaggtgcc cacttcctcc    31680
ctaccctggc acctagcaaa tgactcaagt ggggcaggac atccttgggg aagtggaatc    31740 agcgggggggg ggggggagtg tggggagagc agggtccagg aggagaggag ggctgggaga   31800
ggaggttgac cagcagcccc gacctgtcac ctcccgctct gctccaagct gaccctgggg    31860
tgtttccacc tgaggctggt cccctccctc cagctcttgc cctgccctag cccctttgct    31920
ctgagtggcc ctgtgggaat gtatcgggcc tgattcagct tccagcttaa ctggaccccg    31980
gtctgtcctt tgccacatcc cctctgtgtg acctggcgct ccttacctcc cttcctcgt    32040 accatgagaa taatatttcc ccatgttgtc ttgaggatca aatataacac ggctacctgg    32100
```

```
cctggccagt gcctgccaca caatagggcc tccctaaggg ctggttccca tccctctac    32160
tggtcccctg ttgattccag gtggaagcca ccccgtcccc cccagctgt gttagggcac    32220
ccgccctgcc ctgcccatca caagcacctg cttaccaggg atgactgcct caggcagggg   32280
ctgagttcag tcatctaaaa taccccggt caaagaaaaa tctgaggccc aatagaattt    32340
taaagagtta attgagtaag aaaggattgc tgaattggga aacagcaaac tggaggaggc   32400
ttcgtgctat ggtgaaaaag tgtcggagac aaggtttatc gggtgaatat gaaactgcag   32460
taaggacatt atttgattgg ttgcacttac aaaactgcct gtttgggttt accttgttgg   32520
aaaatccctg gtcacgttgg tgccagtgtg agtttaggga ggtctccgaa tacaggtgag   32580
accggaactt agccttgccc aggttttttga tgctgaagag agaaaaaagt caaagcaaaa  32640
gcaaatcagc ttttagtgca aaacagaagt gcaggctcag gggtgggagt gcaggcggac   32700
tcagaagagc cagtcgggcc cagtggagtt tggggttctt gtctttgctg gtttattaaa   32760
ttaaggtgtg gagtaagcat aaggatttct gggaagaggt ggggatttct tggaattggg   32820
agggcaatgc agttttgtac caaacatggg catacatgga acggctgtgg tgcgggtggg   32880
tgtggggttt agtgagacaa ggagggtatg attgagtgtg aggcaaaacg tgggtcagac   32940
ccagcgccga gttggatctc actggtctta gctgaattgg ccacttcctg tttgtcagga   33000
tcctgtgggc ccatccctc cccctgtccc tacaggtggt ttcagcaact ccttctgtgt    33060
ctgtcatgtg aacctgctgc ctggagttct tgtttcttct gtgacctccc agtatccaca   33120
tctcagcatg gccctctgtc agctggcttt aagttttgtt tgtatctaac agaagtaccc   33180
atctgatatg accccagttg agtttcccat agcttgcagt ttcagggggt tacagctgtt   33240
ctaaaggcct cgtaggtatt gcctgtccag gaatgtttca gggctggttt tgttttaat   33300
tttgctttta tatccaccag ccccaccaca tcaagaaata cacagattta gtgccagagg  33360
ttccttccat ccaaacctgg gtttccttcc tcctttggt gaagaaggaa aagaaaaaa    33420
caagacaatc gctcgcccag ccaagtcagc attgcgttca tttccctaag ccccatttcc   33480
tcaggagggc ttcctcccct tacagagttg ccacggcaac caagtcagct ctgctcagga   33540
gccgccctgg acagcaaact gggctgtgct gagtcctgtc caagacgagg ggagggcagg   33600
gaagattaga agccgagagc actcagccga ccccggaatc cttacgaagg gctgggctgg   33660
gggactgagg aaaaactctc cccccaaaac aagatgatct gtggtttaat aacaggccca   33720
gctgggtcca gaggtgacag tggagagccg tgtaccctga ccagcctg cagaggacag     33780
aggcaacatg gaggtgcctc aaggatcagt gctgaggggtc ccgccccat gccccgtcga   33840
agaaccccct ccactgccca tctgagagtg cccaagacca gcaggaggaa tctcctttgc   33900
atggtagttg tactcaatgc tgtggagttt gagacattat ttttaaactt taaatagccc   33960
cacaggtaag ctataaggga gaatgcagag accacaggca ttttcaaaac ataaggagtt   34020
ttaatgttaa ggagtttaag gagaatgtca aagaaacatt ggccttggag tcaaatcctg   34080
agcttcctgc ttgatggttt tgggcggtga ctctcgctgt ctggatttta ctttcttcat   34140
ctgtgaatta agaatgaggt ggccgggcac tgtggctcac gcctgtaatc ccaacatttg   34200
ggaggccgag gcgggcagat cacaaggtca ggagatcgag acgatcctgt ctaacacgat   34260
gaaaccctgt ctctactaaa aatacaaaaa aaattaccag gcctggtggc aggcgcctgt   34320
agtcccagct actcaggagg ctgaggcagg agaatggcat gaacccagga ggcagagctt   34380
gcagtgagcc aagatcgcac cactgcactc cagcctgggt gagagagcaa gactccatcc   34440
ccccaaaaaa aagaatgagg tctcttgtgt gtgcacggca agaaacaatt ttacatcatg   34500
```

```
cctcagtgca cacacaaata catactggtc cccagttcct tatctgcaat tccatnattc    34560
ccagatccct gcaaaccaca cgttttggtg gcagctgact tcaggagtaa tcctgctctg    34620
tactgacttg agttctttgt agacctacca ttatttttta catttaatgt gaatatttgc    34680
ttgtttcact gttgaaacat gtgtgggtgt gattacaggg agcagtccag cctctgctgg    34740
gaatggtcag gaatatacca tatgcacccc gtgtcctttc taaaatagtg gaaattctga    34800
atgcctaaac acatctggat tccaggaatt tacattaagg gatatatatt tgaaataacc    34860
cacaaaaaca atactcaccc ctgctacgct tggtacactc tgatatttc  aaattgattt    34920 tcttttaaa  atgctgcttt tgaaccaata atttcataac ccaatgatgt gttgatattc    34980
acattttgaa gacactggta taaagtgttt gacccaacag gcatgtggca gatggaagtg    35040
atcactggga tgtttccact tccttggcct ggaaggctca cttcatgttg gtgctgagct    35100
gaaaaggatt cattcctctc caaagcacca tggcactccc ctggtgtttc aatgttctca    35160
ggctgccata gtaaaatatc acaggctggg tgacttcaac atctggcttt tattttctca    35220
cagatccaga ggcaagaagt ccaaggtgaa ggtgccaaaa gggttggagt ctggggagga    35280
ctctcttgct ggcttatgga agctgccttt gcactgtgtg ctcacacagt cttcttgtgt    35340 cccttctgt  tcttacaata ggacactagc cctctaatag aattagagcc ctacccttgt    35400
gatctcattc agtcttaatt gcttccttaa aggccagatc tccaaatgta gtcacctgag    35460
tttaaagctt cagcatatga attttggggg cacacaattc cctctatagc actaatgact    35520
ccataaaaca gtcccacat  cacagctgtc caggaaaatt aacatgtagt catctcttat    35580
gcaatggctg ttatgcactc ccacactttc ctccaacctt atcctttctt ctttccaact    35640
agagagcagt atctttattg aggatgccat taagtatttc aaggaaaaag tgagcacaca    35700
gaatctgcta ctcctgctga ctgataatga ggcctggaac ggattcgtgg ctgctgctga    35760
actgcccagg taagctccat ggggttacct ccattgggca ctccggcgat gccacccagc    35820
tctcccctgg gctagttttc cctgacaggc acacctcctc caggcagccc cctctgctgg    35880
gcttgaggat gaccttcttg gcactccagg aagaatattt cctccatgtc cttcgctggc    35940
agtgagtagc ctcaggctga ggggatagga agcccacagg aacagggtca tttctgccat    36000
ctgctggtga tgggaacttt gccagttact ttctcacttt cagcctttct tcatcaatgg    36060
agttttattg tgagaaaaat gagatcgtgc atgtaaagtg cttagcataa tgactgacac    36120
acagtaggtg cacagttaac gttaacatct tacaagcttg gtggaaacag aaccagggtt    36180
aaggatcttc ttcttgaaga tgggagccca gcaggacttg acctttggga caagtcagaa    36240
aaatcctgac ctaaccaatg tgtgttcctg gggatgctgg ctggagccct ttttctcatc    36300
tgaggaattc cataaacacg gcaggaccct tctgctggtc caggatgccg agaggctgga    36360
gtggagttgc acagcgctgg gtctctttcc agctctgtct gtgtccagtc cctgggctct    36420
gggcttatgt cagagactgg aaactgtcat cagtctaata ggaatagcaa ctcaatgtga    36480
taggagtgtg gtgaaggcct tagaggcaac tccaggtcaa aggtggggaa ccaacaccaa    36540
gatcctgccc aaaggcccag agagaccggg atcagcgtca gagcctggag tcaggatgga    36600
gcaagagtca gccttggttg taggacaagc aggaaggctg gggcaccagg gctgggacta    36660
gggtgtggaa agagaggcac caagggcttg aaacttaagg aggtcatgaa cttgcagagg    36720
acatgtgagt gggagaggga tatttcttcc ctgtctggat gatcccaaca ctcatgggca    36780
tatagggtca tggttgcctg tgtctctcac accacgcctt ggaactggca agttctgggc    36840
```

```
tacccttga gaccttcttc tcttctacac agagaaaccc ctgacattga caagcagtat    36900
gtcttagtga ccattttcat agtagaatta gttgctgcca atttgtgtaa tttcagggat    36960
actgagcaga ctcacaactt cccaaccaag gaggaaaaca cttcctctac catcttgtcc    37020
aaattcaggt cttttcagca ttagcaattt atataggtgg ttctgaaagt gttttgaatc    37080
ttctagaggt tccataaaat tgcaaatggc cttggtgtgc acacaggtga agctgtcact    37140
actaaggcat cagttaggct ggtgacacct gcgagtgaga cctggaaggt tggggtgca    37200 ggtggtaggt caggaggcag taaggtggct ggagcgtcca tgtggagcca gaatgaatag    37260
ccagatctcc cactccagtc agctggggca gtggccagaa ccagtagcct tcagccaggt    37320
gaaagggcat gaggcattgg aagggagcag atgccaggca aagtgaactc ctgtctctcc    37380 gggttttgt ttttgtttga attcaaagta ctcagagata gccagactgc aatgtctgag    37440 ggcacccta cctttgacac cacctgcaaa tttaagggga tttctaaatc catcctttga    37500
ttttgtaatt cactggaagg actcacataa ctcactgaaa actgctattt cacaattgtg    37560
gttgatcaca cggaaagaac acagattaaa atcagcctaa gaaagagaca cacggggcag    37620
agtttgggag ggttttaagt gtgaagcttc attgtcctca ggacgctgtg ttctcctgtg    37680
tgaatgtggg acaaaacaca tgcggtgttg ccaaccaggg aagctcaccc agttaaggaa    37740
aaattcctgt gaatcacatt aaaccagaaa tgaagccttt tttcaggatt gttgttacag    37800
gggagggaga ctgagcccag ctccaaatat agtaaagaca gaggggagt cacagccaac    37860 accagggtgg gggcgggaga tggaacagga ctgataggag acaccagagt gggggggttcc    37920 tgctaaattg gcctaacagg attctcacta aaggcaggtc agacactcac ccatcaatgg    37980
tgggggtgaa gagcataatc agatagcaaa gcgtaatcag acagcaaggg gggaagaccc    38040
tccctaaact gacttgggga gattcttgct gagctgggtg gtgcaggtcc agcaagcagt    38100
gggtggctgt ggaaggccaa ggtcggcgcc tagtggagaa gaggctcaga agagcccagc    38160
tggagttggt caaggagaaa gtccttcttt ctcaacccat gccttagtgt ccagagtatc    38220
tgctggggct ggatcacaag ctgccctcat ggctgacctg gagtctccag cccctccctg    38280
aggtctaacc cctttagtcc ccgggtcctc tgggatcagg aaagacacca aatagcccca    38340
aaccccatca tccatcagat tcctatacgg tcccgtggcc aaatcaccag gcaaagacag    38400
atgttcctac caggcaggac attccagggg cctggagatc acttcccagg agctgaggac    38460
aaagggaagg cctctctttg ggtaaagttc atgcttcact ttcctgccat cctgggaata    38520
aggtctcttt gtctcactct cactgctctt tgttcatctg cagagttttc cctctccaaa    38580
cactttggca gtcacggtgt tgacctgccc ttgaatgagg aggcatcttt atcaaacacc    38640
taccatgaaa gagcatctga gatgccttta agatatttat ttccatatgg aataaatatt    38700
gaggagtatc tatgatgaac aaaatgtgtt tgagtttgaa agataattaa ttccatttgt    38760
aaaatttgtt tctatttgat cgatagtgaa agctctgcaa tttacacagg atagagatca    38820
catggagctc atttcacaga cagggaaact gcatttcttt ttttttttt tttttttgag    38880 ttggagtctt gctctgtcgc ccaagctgga gtgcagtggc gcgatctcgg ctcactgcaa    38940
gctctgcctc ccggttcaag caattctcct gcctcagcct cctgagtagc tgggactaca    39000
ggcgcccacc accacgcccg gctaattttt tgaattttg gtagagacag gtttcaccg    39060 tattagtcag gatggtctca atctcctgac cttgtgatcc accgccttg gcctcccaaa    39120 gtgctgggat tacaggtgtg agccaccaca ccgagccaaa actgcatttc ttaatccttt    39180 aaccttcct tgtgcaggaa tgaggcagat gagctccgta aagctctgga caaccttgca    39240
```

```
agacaaatga tcatgaaaga caaaaactgg cacgataaag gccagcagta cagaaactgg    39300
tttctgaaag agtttcctcg gttgaaaagt gagcttgagg ataacataag aaggctccgt    39360
gcccttgcag atggggttca gaaggtccac aaaggcacca ccatcgccaa tgtggtgtct    39420
ggctctctca gcatttcctc tggcatcctg accctcgtcg gcatgggtct ggcacccttc    39480
acagagggag gcagccttgt actcttggaa cctgggatgg agttgggaat cacagccgct    39540
ttgaccggga ttaccagcag taccatggac tacggaaaga agtggtggac acaagcccaa    39600
gcccacgacc tggtcatcaa aagccttgac aaattgaagg aggtgaggga gttttgggt     39660 gagaacatat ccaactttct ttccttagct ggcaatactt accaactcac acgaggcatt    39720
gggaaggaca tccgtgccct cagacgagcc agagccaatc ttcagtcagt accgcatgcc    39780
tcagcctcac gcccccgggt cactgagcca atctcagctg aaagcggtga acaggtggag    39840
agggttaatg aacccagcat cctggaaatg agcagaggag tcaagctcac ggatgtggcc    39900
cctgtangct tctttcttgt gctggatgta gtctacctcg tgtacgaatc aaagcactta    39960
catgaggggg caaagtcaga gacagctgag gagctgaaga aggtggctca ggagctggag    40020
gagaagctaa acatnctcaa caataattat aagattctgc aggcggacca agaactgtga    40080
ccacagggca gggcagccac caggagagat atgcctggca ggggccagga caaaatgcaa    40140 acttttttt ttttctgaga cagagtcttg ctctgtcgcc aagttggagt gcaatggtgc      40200
gatctcagct cactgcaagc tctgcctccc gtgttcaagc gattctcctg ccttggcctc    40260
ccaagtagct gggactacag gcgcctacca ccatgcccag ctaattttg tatttttaat      40320 agagatgggg tttcaccatg ttggccagga tggtctcgat ctcctgacct cttgatctgc    40380
ccaccttggc ctcccaaagt gctgggatta caggcgtgag ccatcgcttt tgacccaaat    40440
gcaaacattt tattaggggg ataaagaggg tgaggtaaag tttatggaac tgagtgttag    40500
ggactttggc atttccatag ctgagcacag caggggaggg gttaatgcag atggcagtgc    40560
agcaaggaga aggcaggaac attggagcct gcaataaggg aaaaatggga actggagagt    40620
gtggggaatg ggaagaagca gtttacttta gactaaagaa tatattgggg gccgggtgt     40680 agtggctcat gcctgtaatc cgagcacttt gggaggccaa ggcgggcgga tcacgaggtc    40740
aggagatcga gaccatcctg gctaacacag tgaaaccccg tctctactaa aaatacaaaa    40800
aattagccgg gcatggtggc gggcgcctgt agttccagct aactgggcgg ctgaggcagg    40860
agaatggcgt gaacctggga ggtggagctt gcagtgagcc gagatatcgc cactgcactc    40920
cagcctgggt gacagagcga gactccatct caaaaaaaaa aaaaaaaga atatattgac     40980 ggaagaatag agaggaggct tgaaggaacc agcaatgaga aggccaggaa aagaaagagc    41040
tgaaaatgga gaaagcccaa gagttagaac agttggatac aggagaagaa acagcggctc    41100
cactacagac ccagccccag gttcaatgtc ctccgaagaa tgaagtcttt ccctggtgat    41160
ggtcccctgc cctgtctttc cagcatccac tctcccttgt cctcctgggg gcanatctca    41220
gtcaggcagc ggcttcctga tgatggtcat tggggtggtt gtcatgtgat gggtcccctc    41280
caggttacta aagggtgcat gtcccctgct tgaacactga agggcaggtg gtgggccatg    41340
gccatggtcc ccagctgagg agcaggtgtc cctgagaacc caaacttccc agagagtatg    41400
tgagaaccaa ccaatgaaaa cagtcccatc gctcttaccc ggtaagtaaa cagtcagaaa    41460
attagcatga aagcagttta gcattgggag gaagctcaga tctctagagc tgtcttgtcg    41520
ccgcccagga ttgacctgtg tgtaagtccc aataaactca cctactcatc aagctggact    41580
```

-continued

```
tgttcgagtc attctttggt ctctcagctc tttccaagct ttgggggcca tcagtctcaa      41640
gtttttctcg taatggtggt gatggtggtt gtgatggcag cagagtggtg ggggccttgg      41700
caagtggtcg gtgctcttcc agaccagggg acaccgatgg accgatgaag ttccagggga      41760
acttgaagtg ctgtgttgga aagaggttaa tttgggaaga aaggaaaaat gaaaggagat      41820
gccaggaaca ggtcaaggaa ccttgaggtg tgtccaggag ttcaaccccg cttgtggtca      41880
cgagacctcg cctctctgag cctcagtttc ctcatcagct gtagaagggt acctggacaa      41940
ggtgatgtct caggtccacc cagctctccc catcttgtgt cctggagact tgggtccaat      42000
cagcactgac tgatggctgt gcctttgtgg tgccgatgga ggctcccctg ggctctgggt      42060
gcctgacttc ccttcctcat gatccttctt ccagggtctc gggaaacgag gcttccatgg      42120
cccctcctgc ttgctcactg gactctcact ttcccagctg gtcatttccc tgagacctca      42180
aaaccccacc aaccccactg gggcacccac agaaagcttg tacatgtctg gctctggctg      42240
agcacaggtg tggtttccat ctgcgagtca gagcccggga ttgacatggg acgctcgagg      42300
ctgactagtg tcagagggc ctgtgtgcag attgggagaa gattatcgag taatagaggg       42360
gcaaagaggg acatccagac agcaaacacc cccatccagt ctgtcctcac gttttgccca      42420
gactcctgca agaacttcca gaatggtctt ccatgtgcaa ctgcccgtcc ctgcccatgt      42480
cctggatcat tctccacact gcgccaggtt gggctttaac aagatcatgt tttgggtttt      42540
tgggggtttt ttgtttgttt gtttggtctc actctgttgt gaggctggcg tcccgtggca      42600
tgagcatggc tcactgcatc ttggacctcc cggcctcaaa ctacccttcc accttgaccc      42660
cctgagtagc tgggaccatc cgtgtgtgcc acattgccca ggctggtctc aaactcctga      42720
gttcaggtga tctgttcgcc ttggcattcc aatgggctgc aattacagac acgagccacc      42780
gtgcccacct aagaacatag atttgatcga gcacccactt ctgaccattc aatggcttcc      42840
cattactctt agcacaaaga tgtaggccat gatgctgcct aaagtagcct gttgcggcct      42900
ggggtcctgt gaaggaagag ccagaggcaa cgttctggtg cagagggttt ctaggaagtg      42960
attctaggag cagaactgag gatccaggag ggaaggagga aacgttgata caagaagttt      43020
ttgaatgggc catccatatg ggcaatgaga ccttctgagg tgccttcaag gagcgtcctc      43080
agaatctttg tttccaggga ggagacatgg aggcctttat ccactgcttt agctgtgtcc      43140
caggggttct ggtacattgt gtctttgttc tcattggttt caaagaactt cttgatttct      43200
gccttaattt tgttatttac ccagtaatca ttcaggaaca cgttgttcaa tttccatgta      43260
gttgtgcggt tttagtgag tttcttaatc ctgagttcta atttgattgc actgtggtct       43320
gagacactgt ttgttatgat ttccattctt ttgcatttgc tgaggaatgt tttacttcca      43380
attatgtggt cgactttaga ataagtgtta tacggtgctg agaagaaagt atattctgtt      43440
gatttgggac ggagagttct gtagatgtct gttaggtcca ctcagtccag ggctgagttc      43500
aagtcctgaa catccttgtt aattttctgt ctcgttgacc tgtctaatat tgacagtggg      43560
gtgttaaagt ctcccactgc tattgtgtgg gagtctaagt ctctttgtag gtctctaaga      43620
acttgtttta tgaatctgcg tgctcccgta ttgggtgcat atatatttag gatagttagc      43680
tcttcttgtt gcactgatgt ttgttggttt aaaagatctt ttttgatctt tgttggttta      43740
aagtctgttt tatcagagac taggattgca accctgcttt ttttgtttgt ttgtttgttt      43800
gtttgttttg ctttccattt gcttggtaaa tgttcctcca tccctttatt ttcagcctat      43860
gtgtgttttt gcacatgaga tgggtctcct gaatacagta catcaacggg tcttgacttt      43920
atccaatttg ccagtctgtc tgttttaatt ggggcattta gcccatttac atttaaggtt      43980
```

```
catattgtta tgtgtgaatt tgatcctgtc atcatgatgc tagctgatta ttttgcacat   44040
tagttgatgc agtttcttca tggtatcatt ggtctttata ttttggtgtg gttttgcagt   44100
gtctggtact ggttttcct ttccatattt agtgcttcct tcaggagctc atgtaaggcc   44160
ggcctggtgg tgacaaaatc cctcagcatt tgcttgtctg gaaaggattt tatttctcct   44220
ttgcttatga agcttagttt ggctggatat gaaattctgg gttgaaaatt cttttcttta   44280
agaatgttga atattggtcc ccactctctt ccagcttata tagggtttct gcagagagat   44340
ccactgttag tctgatgggc ttcccttcgt aggtaacgtg atctttctct ctggctgccc   44400 ttaacattt ttccttcgtt tcaaccttgg agaatctgat gattatgtgt cttggggttg   44460
ctcttcttga agagtatctt agtggtgttc tctgtatttc ctgaatttga atgttggcct   44520
ggcttgctgt tggggaagt tctcctggat aatatcctaa agtgtgtttt ccagcttgtt   44580
tccgttctcc ccatcacttt caggtacacc aatcaattgt aggtttaatc ttttcacata   44640
gtcccatatt tcttggaggc tttatttgtt ccattgtcat tctttttct ctaattttgt   44700 cttcacacat tgtttcagta agttgatctt caatctttga tattccgctt gatcaatttg   44760
gctattgata gttgtgtatc cttcacgaag ttctcatgct gtgttttca gctccatcag   44820 gtcatttacg ttcttctcta aactggttat tctagttagc agctcctgta acctttcatc   44880
aaggttctta gcttccttgc attgggttac aacatgctcc tttagctcag aggagtttct   44940
cattacccat cttctgaagc ctacttctgt caattcgtca aattcattct ccatccagtt   45000
ttgtgccctt gctggagagg agttgcaatc atttggagaa gagacattct ggtctttgga   45060
attttcagcg tttttgtgct ggttttcct tatcttcatg aatttatctt tgatctttga   45120
ggatgatgac cttcggatgg gcttttgggg gaggngaggt ccttttagtt gatcttgatg   45180
ttattgcttt ctgtttgtta gttttcatc taataatcag gccctctgc tgcaggtctg   45240 ctgcagtttg ctggaggttc actccagacc tttttgcct gggtatcacc agcagaggct   45300
acagaacagc aaagatagct gcctgctcct tcctctggaa gcttcgttcc agaggggcac   45360
tgacttgata tcagccagag ctctcctgta tgaggtgtct ccctcaggag gcacgggagt   45420
cagggaccca cttgaggagg cagtctgtcc cttagtagtg cttgagcgct gtgctgggaa   45480
atgcgctgct ctcttcagag ccagcaggca ggaacgttta agtccactga agttgcgccc   45540
acagctgccc cttcccctag gtgccctctc tgtccgggga gatgggagtt ttatctataa   45600
gcccctgact ggggctgctg cctttctttc agagatgccc tgccagtgag gaggaatcta   45660
gagaggcagt ctggccacag ccgctttgct gtgctgtggt gagttccgcc cagtccgaac   45720
tccccaccct ccttagcact gtcagggaaa agctacctac tcaagcctca gtaatggcgg   45780
atgcccctct ctctaccaag ctcagtggcc ccaggtcaac ttcaggctgc tgtgctggag   45840
cgagaatttc aagccagtgt tcttagcttt gctgggctcc gtgggagtgg gacctgctga   45900
gcaagaccac ttggctccct ggcttcagcc ctctttccag gggagtgaac ggttctgtct   45960 tgctgggtt ccaggcgcca ctgggtaca aaaaaaaat tcctgcagct agctcagtgt   46020
ctttcccaaa cagccaccca gttttgtgct tgaaacccag ggccctggtg gtgtaggcac   46080
atgagggaat ctcctggtct gtggattgca aaaactggga aatgcatagt atctggactg   46140
gatagcacag tccctcatgg tttcccttgg ctgggggagg gaggccccccg gctccttgca   46200 cttcctgggt gaggcaacac cccacccctga ttctgctcgc cctccgtggg ctgtaccccac   46260 tgcctaacca gtcccaatga gatgaactgg gtacctccgt tggaaatgca gaaatcactc   46320
```

```
gccttctgtg ttgatcttgc tgggagctgc agtctggagc tgttcctatt cagccatctt    46380
gccagatctc ccctctatct tcttttttt tttttttttt ttgagacaga gtcttgctct    46440
gtctcccagg ctggagtgca gtagcacaat ctcggctcac tgcaagctcc gcctcccgag    46500
ttcacgccat tctcctgcct cagcctcctg agtagcggac tacaggctcc tgcttttttg    46560
ttttgttttt tgtattttta gtagagacag ggtttcacca tgttagccag gatggtctcg    46620
atctcatgac ctcatgatcc gcccgcctca gcctcccata gtgctgggat tacaggcgtg    46680
agccaccacg tctggccgat ctcaccctat cttaagctat ttccagaaac agaatgacta    46740
ggtcagaggg tattaacatc gaaaaatgtt tccatacctc gaaccacatc gttatgcaaa    46800
taaattgtat caatttacac tcacaccagc tttacaggag ggtgttcatt ccttcagtct    46860
taagaattct cagtattctt tctctttaaa aagaaaaaca gatctttaca cggagaaaag    46920
tttttcaagt tcggcttgtg attatcctgc ctgcaaagat gagggaaaag agcgaaagtt    46980
gatcatgttt aggcattact ttaagaagac aaaagagcat ttttcaacca cccttctga     47040 gaccagacta aaatcacagt caaggcactt ataggtataa tagcagctga tatgcttgg     47100 ggctgggtcc ctgcccaaat ctcacatcaa actgtaatcc ccagcattga tggtgatgcc    47160
tgctggaagg caactgggtt atgggagtgg atttcccctt tggtgctatt ctcttgatag    47220
tgagttccct tcaccttctg ccatgattgg aagttccctg aggcctcccc agaagctgat    47280
accaccatgc ttcctgtaca gcccgcagaa ctgtgagcca attaagcccc ttttctttat    47340
aaattaccca gtctcaggta tttcttttca gtagtgtgag aatggactaa tacagcaact    47400
aatgctaata gtggcgaaca atgtgtggac tttactttgc accactaact gctctaagat    47460
gttagaaaaa actcaccgta ctctttcaag aacctctgaa gtgtgtatca tttgtaccac    47520
cattaacaga taaggaaact gaaacagatg ttcaatgact tggccaaggt cagaaatcta    47580
ctgatggcta aagactcggt tccgacccag tcatatggat tccagaactc acacattgcc    47640 ttggtacccct ctctgctgac aaaaaacttg aatgagacca acaggagatc agagatttca    47700
acagctattt agaagacaga actgactgaa gaaatgacaa ccgaataaag atgggtgaag    47760
gcagctgcga tccacagcaa tatggagagg acatccagcc aagaagaatc acctgctagg    47820
cagagcctca gagagaggag aagttcacca gccccatgac ccatatagga ttcaaggcag    47880
cctcgagtct acaccaatga aaaaatcaga gagttcatga ctcaatcaaa aagccccaga    47940
aataatatcc ttgtattctg cactttaggg gggttcccat ccaatcaccc cacaggtaag    48000
cctgccagtg gacttgtctt cctcctacat aggaatggat ctaggatcag atatatgaga    48060
aagacaaaat aaggaaaaga gaccaagact aacaaatgca aaatgagtcc agaagaaatg    48120
aataattttg aaaatggaca ataattttga aaaaatcaaa ctcatgtcct tggagagatt    48180
taaactcacg ctggccgggt gcagtgactc acacctgtaa tcccagcact ttgggaggcc    48240
gaggcaggca gatcacctga gtcgggagt ttgagaccag ccttaccaac atggagaaac     48300
ccctgtctct actaaaaata caaaattagc tgggcatggt ggcgcatgcc tgtaatccca    48360
gctactcggg aggctgagac aggagaatcg cttaaacctg ggaggcggag gttacggtga    48420
cctgagttcg tgccattgca ctccagcctg gcaacaaga gtgaaactct gtttcaaaat     48480
aaaataaaat tgtatgcttg agaacaagat gtactgaaaa gaaggggggaa acaatagaac   48540 aaaaaaaaat tcttgggaat taaatgattg acaaaataaa caactcaaga gagggttgaa   48600
aaagtctaga aaagcttcca gaaaataaac tagaaagatg acaggagaaa tggagctaaa    48660
gcggaattga aatgttacca tacatcatga cttcctggaa agctacttga gaaagagcta    48720
```

```
cagagggagt gggaaggacg tgcgtgtgtg tgcacgtgtg tgcacccatg gtgagtgggt   48780
ggggataacc aagagagaaa aagacatggg atccaggaaa caagcaactc aacccagtga   48840
gaagggaatc caaggatcac ggctgagcat gcagcaggcc taaagaacaa ccagtccagg   48900
atggaataag aagggaaggg ttctgtgggg acttcacaga gtacctcata tgattcacaa   48960
tttgagggaa gctgaggaaa tcatgaaggc aaacagtgca aggggggga aaacaaaggc    49020 aattagaaac atcaggaaaa actaaagctg tgccacaaag catgtgcagc catattgtac   49080
aactcaactc tatagtaaac agtatttaaa acatcacaaa aatgtaaaca cgcttgtttg    49140
atttttaact ttgagcacaa aacagaacat ttaaatatga gaaccaaata aacttgttgc   49200
caatcagtac caaaattaaa gtacaatggt agtgcttggg aagggaggca ctgaaaagga   49260
agattaatat cctcgtttta taaaatgggg agtcaagaaa cactggccat agtgagggcg   49320
taagaaaaac attgcaagta aattgtttac aaagtttcta atggggatta taaaactagc   49380
gatataatat tagaagaagg tgggagggg agttagaagt gtaaagataa cttaataata    49440
ataaataaat aataagtaat gaataaaaat attaataata aaaatagtaa taaaaaaatt   49500
atatcctaat aggaagcaaa taaatagtga tgtctaaatt tcaaaatgga gaaaataaaa   49560
aatgcaatag cttatattta ttgaccatct gctttgcacc aggaaccttc taaatgcttt   49620
gcaggcatta acttattttt agttctcaca acaactgtta gaaagatact attatcacct   49680
gcatgcttca gatgaggaaa ctgaagctca gagaagttaa gctagtgaca gcacctaact   49740
agtgacaccc ggaattcaaa ctcaggcttc ctatctccag agcatgcact ctcactattt    49800
catgtcccag cataagaaaa ttatttaaat atatttattt actccctaaa gaaaagcta    49860 gggccgggcg tggtggctca cacctgtaat cccagcactt tgggaggctg aggtgggtgg   49920
atcacctgag gtcaggagtt caagaccagc ctgggcaaca tggtgaaacc ccgtctctac   49980
taaaagtaca aaaattagct gggcacagtg gcatgtgcct gtaatcccag ttactcggga   50040
ggctgaggca ggagaatcgc ttaagccagg gaggtggagg ttgcagtgag ccaagatcgc   50100
gccactgcac tccagcctgg gtgacagagg gagactccgt ctcaaaaaaa aaaaaaaaa    50160 gaaaaaagaa aaagctaaaa ttgggactaa ttgctcttaa tttgggtaag tggagccgtc   50220
tgtactaatt gattgattga ttgggaaggg gtaagtagag ccctctgtac taattgattg   50280
gtcttaacca tctgctgcac tcacttatta ctttattttt ttaatttaag aggacagaat   50340
tcagtttata gtagttagta actgctaacc tcaatagcaa gttaggttct ggtgtcacct   50400
tccttgaagg ttatggagca atgtgaacat gtgccagtga gaataagcc tgcctctgat    50460 atggaagtgc tgggaaggga agcatgtagt ccctttaaat gatatggatc ccacctctgg   50520
gaggcctgta atcccagcac ctgtaatccc agcactttgg gaggccaagg cggatagagc   50580
acaaggtcag gagttcgaga ccggcctggc caatatggtg aaaccccgtc tctactaaaa   50640
atacaaaaat tagctgggca tcgtggtggg tgcctgtagt cccagctact cgggaggctg   50700
aggcaggaga attgcttgaa cccgggaggc agaggttgcc gtgagccatg attaccacc    50760 tgcaccccag cctggagaca gagtgagact ttgtctcaaa gaaaaaaaaa gaaaagaagt   50820
gggggcctca cacacagttt cctggataac aggaactatt gtaagagatc ccaccaaacc   50880
acaaccatgc agaatgaatc acagccctgc acaaaggcca cctctatgag gacatctgcc   50940
caacaactgt ctgtttaacc ttgagctaag gtgaccttg ttattaattc ttgtacctag   51000
ggatcattat ttaaaataac ttacataatt ctccccattt tggctttaaa aacctctgct   51060
```

```
<210> SEQ ID NO 4
<211> LENGTH: 20
<212> TYPE: DNA
<213> ORGANISM: Artificial sequence
<220> FEATURE:
<223> OTHER INFORMATION: Single strand DNA oligonucleotide

<400> SEQUENCE: 4
acaagcccaa gcccacgacc                                               20

<210> SEQ ID NO 5
<211> LENGTH: 20
<212> TYPE: DNA
<213> ORGANISM: Artificial sequence
<220> FEATURE:
<223> OTHER INFORMATION: Single strand DNA oligonucleotide

<400> SEQUENCE: 5
cctggcccct gccaggcata                                               20

<210> SEQ ID NO 6
<211> LENGTH: 52
<212> TYPE: DNA
<213> ORGANISM: Homo sapiens
<220> FEATURE:
<221> NAME/KEY: misc_feature
<222> LOCATION: (27)..(27)
<223> OTHER INFORMATION: N can be A or G

<400> SEQUENCE: 6
tcaagctcac ggatgtggcc cctgtangct tctttcttgt gctggatgta gt           52

<210> SEQ ID NO 7
<211> LENGTH: 52
<212> TYPE: DNA
<213> ORGANISM: Homo sapiens
<220> FEATURE:
<221> NAME/KEY: misc_feature
<222> LOCATION: (27)..(27)
<223> OTHER INFORMATION: N can be G or T

<400> SEQUENCE: 7
caggagctgg aggagaagct aaacatnctc aacaataatt ataagattct gc           52

<210> SEQ ID NO 8
<211> LENGTH: 52
<212> TYPE: DNA
<213> ORGANISM: Homo sapiens
<220> FEATURE:
<221> NAME/KEY: misc_feature
<222> LOCATION: (27)..(27)
<223> OTHER INFORMATION: N can be A or G

<400> SEQUENCE: 8
ccccagttcc ttatctgcaa ttccatnatt cccagatccc tgcaaccac ac            52

<210> SEQ ID NO 9
<211> LENGTH: 52
<212> TYPE: DNA
<213> ORGANISM: Homo sapiens
<220> FEATURE:
<221> NAME/KEY: misc_feature
<222> LOCATION: (27)..(27)
<223> OTHER INFORMATION: N can be A or G

<400> SEQUENCE: 9
accttcggat gggctttggg gggaggngag gtccttttag ttgatcttga tg           52
```

```
<210> SEQ ID NO 10
<211> LENGTH: 52
<212> TYPE: DNA
<213> ORGANISM: Homo sapiens
<220> FEATURE:
<221> NAME/KEY: misc_feature
<222> LOCATION: (27)..(27)
<223> OTHER INFORMATION: N can be C or T

<400> SEQUENCE: 10
cactctccct tgtcctcctg ggggcanatc tcagtcaggc agcggcttcc tg          52
```